(12) United States Patent
Westerman et al.

(10) Patent No.: US 10,239,941 B2
(45) Date of Patent: *Mar. 26, 2019

(54) ANTI-HEPCIDIN ANTIBODIES AND USES THEREOF

(71) Applicant: Intrinsic Lifesciences LLC, La Jolla, CA (US)

(72) Inventors: Mark Westerman, San Diego, CA (US); Vaughn Ostland, San Diego, CA (US); Huiling Han, San Diego, CA (US); Patrick Gutschow, Oceanside, CA (US); Keith Westerman, San Diego, CA (US); Gordana Olbina, La Jolla, CA (US)

(73) Assignee: Intrinsic Lifesciences LLC, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,164

(22) Filed: Aug. 31, 2017

(65) Prior Publication Data

US 2018/0057586 A1 Mar. 1, 2018

Related U.S. Application Data

(60) Continuation of application No. 15/485,141, filed on Apr. 11, 2017, now Pat. No. 9,803,011, which is a division of application No. 14/771,135, filed as application No. PCT/US2014/026804 on Mar. 13, 2014, now Pat. No. 9,657,098.

(60) Provisional application No. 61/791,953, filed on Mar. 15, 2013.

(51) Int. Cl.
| | | |
|---|---|---|
| A61K 39/395 | (2006.01) | |
| A61P 7/06 | (2006.01) | |
| C07K 16/26 | (2006.01) | |
| C07K 14/575 | (2006.01) | |
| A61K 39/00 | (2006.01) | |

(52) U.S. Cl.
CPC .......... *C07K 16/26* (2013.01); *A61K 39/3955* (2013.01); *A61K 2039/505* (2013.01); *C07K 14/575* (2013.01); *C07K 2317/24* (2013.01); *C07K 2317/33* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davis et al. |
| 4,301,144 A | 11/1981 | Iwashita et al. |
| 4,472,509 A | 9/1984 | Gansow et al. |
| 4,495,285 A | 1/1985 | Shimizu et al. |
| 4,496,689 A | 1/1985 | Mitra |
| 4,609,546 A | 9/1986 | Hiratani |
| 4,640,835 A | 2/1987 | Shimizu et al. |
| 4,670,417 A | 6/1987 | Iwasaki et al. |
| 4,676,980 A | 6/1987 | Segal et al. |
| 4,703,008 A | 10/1987 | Lin |
| 4,766,106 A | 8/1988 | Katre et al. |
| 4,791,192 A | 12/1988 | Nakagawa et al. |
| 4,816,567 A | 3/1989 | Cabilly et al. |
| 4,938,948 A | 7/1990 | Ring et al. |
| 5,021,236 A | 6/1991 | Gries et al. |
| 5,391,377 A | 2/1995 | Barnwell |
| 5,441,868 A | 8/1995 | Lin |
| 5,547,933 A | 8/1996 | Lin |
| 5,618,698 A | 4/1997 | Lin |
| 5,621,080 A | 4/1997 | Lin |
| 5,756,349 A | 5/1998 | Lin |
| 5,767,078 A | 6/1998 | Johnson et al. |
| 5,773,569 A | 6/1998 | Wrighton et al. |
| 5,830,851 A | 11/1998 | Wrighton et al. |
| 5,856,298 A | 1/1999 | Strickland |
| 5,955,422 A | 9/1999 | Lin |
| 5,986,047 A | 11/1999 | Wrighton et al. |
| 6,030,086 A | 2/2000 | Thomas |
| 6,096,289 A | 8/2000 | Goldenberg |
| 6,096,871 A | 8/2000 | Presta et al. |
| 6,171,586 B1 | 1/2001 | Lam et al. |
| 6,210,670 B1 | 4/2001 | Berg |
| 6,310,078 B1 | 10/2001 | Connolly et al. |
| 6,350,861 B1 | 2/2002 | Co et al. |
| 6,391,633 B1 | 5/2002 | Stern et al. |
| 6,583,272 B1 | 6/2003 | Bailon |
| 6,586,398 B1 | 7/2003 | Kinstler et al. |
| 6,599,498 B1 | 7/2003 | Groman et al. |
| 6,737,056 B1 | 5/2004 | Presta |
| 6,750,369 B2 | 6/2004 | Connolly et al. |
| 6,900,292 B2 | 5/2005 | Sun et al. |
| 6,960,571 B2 | 11/2005 | Helenek et al. |
| 7,030,226 B2 | 4/2006 | Sun et al. |

(Continued)

FOREIGN PATENT DOCUMENTS

| | | |
|---|---|---|
| CA | 2506668 A1 | 7/2004 |
| CN | 101076730 A | 11/2007 |

(Continued)

OTHER PUBLICATIONS

Saldanha, Jose. Molecular Engineering I: Humanization. Chapter 6 in: Handbook of Therapeutic Antibodies. Weinham:Wiley-VCH, p. 119-144, 2007.

(Continued)

*Primary Examiner* — Zachary C Howard
(74) *Attorney, Agent, or Firm* — Wilson Sonsini Goodrich & Rosati

(57) ABSTRACT

The present application relates to antibodies that specifically bind to hepcidin and methods of using the antibodies. Another aspect relates to antibodies which bind hepcidin and regulate iron homeostasis. Another aspect relates to the use of humanized antibodies which bind hepcidin for the treatment of a disease or condition associated with hepcidin.

28 Claims, 30 Drawing Sheets

Specification includes a Sequence Listing.

(56) References Cited

U.S. PATENT DOCUMENTS

| | | |
|---|---|---|
| 7,084,245 B2 | 8/2006 | Holmes et al. |
| 7,091,321 B2 | 8/2006 | Gillies et al. |
| 7,112,412 B1 | 9/2006 | Bander |
| 7,115,716 B2 | 10/2006 | Watkins |
| 7,217,689 B1 | 5/2007 | Elliott et al. |
| 7,217,798 B2 | 5/2007 | Hinton et al. |
| 7,320,894 B2 | 1/2008 | Geacintov et al. |
| 7,411,048 B2 | 8/2008 | Geacintov et al. |
| 7,649,081 B2 | 1/2010 | Kulaksiz et al. |
| 7,723,063 B2 | 5/2010 | Lauth et al. |
| 7,745,162 B2 | 6/2010 | Lauth et al. |
| 7,749,713 B2 | 7/2010 | Kulaksiz et al. |
| 7,754,702 B2 | 7/2010 | Helenek et al. |
| 7,998,691 B2 | 8/2011 | Kulaksiz et al. |
| 8,003,338 B2 | 8/2011 | Kulaksiz et al. |
| 8,017,737 B2 | 9/2011 | Kulaksiz et al. |
| 8,263,352 B2 | 9/2012 | Kulaksiz et al. |
| 8,304,197 B2 | 11/2012 | Kulaksiz et al. |
| 8,304,258 B2 | 11/2012 | Kulaksiz et al. |
| 8,487,081 B2 | 7/2013 | Vaulont et al. |
| 9,657,098 B2 | 5/2017 | Westerman et al. |
| 9,803,011 B2 | 10/2017 | Westerman et al. |
| 2002/0155998 A1 | 10/2002 | Young et al. |
| 2003/0003048 A1 | 1/2003 | Li et al. |
| 2003/0077753 A1 | 4/2003 | Tischer |
| 2003/0082749 A1 | 5/2003 | Sun et al. |
| 2003/0113316 A1 | 6/2003 | Kaisheva et al. |
| 2003/0118592 A1 | 6/2003 | Ledbetter et al. |
| 2003/0133939 A1 | 7/2003 | Ledbetter et al. |
| 2003/0143202 A1 | 7/2003 | Binley et al. |
| 2003/0215444 A1 | 11/2003 | Elliott et al. |
| 2004/0005643 A1 | 1/2004 | De et al. |
| 2004/0009902 A1 | 1/2004 | Boime et al. |
| 2004/0071694 A1 | 4/2004 | Devries et al. |
| 2004/0091961 A1 | 5/2004 | Evans et al. |
| 2004/0096990 A1 | 5/2004 | Geacintov et al. |
| 2004/0143857 A1 | 7/2004 | Young et al. |
| 2004/0157293 A1 | 8/2004 | Evans et al. |
| 2004/0175379 A1 | 9/2004 | Devries et al. |
| 2004/0175756 A1 | 9/2004 | Kolkman et al. |
| 2004/0175824 A1 | 9/2004 | Sun et al. |
| 2004/0197325 A1 | 10/2004 | Law et al. |
| 2004/0229318 A1 | 11/2004 | Heavner |
| 2004/0241651 A1 | 12/2004 | Olek et al. |
| 2004/0248815 A1 | 12/2004 | Connolly et al. |
| 2004/0266690 A1 | 12/2004 | Pool |
| 2005/0019914 A1 | 1/2005 | Staerk et al. |
| 2005/0020487 A1 | 1/2005 | Klaus et al. |
| 2005/0026834 A1 | 2/2005 | Cox et al. |
| 2005/0037421 A1 | 2/2005 | Honda et al. |
| 2005/0048512 A1 | 3/2005 | Kolkman et al. |
| 2005/0053973 A1 | 3/2005 | Kolkman et al. |
| 2005/0089932 A1 | 4/2005 | Kolkman et al. |
| 2005/0096461 A1 | 5/2005 | Cox, III |
| 2005/0107297 A1 | 5/2005 | Holmes et al. |
| 2005/0107591 A1 | 5/2005 | Cox, III |
| 2005/0124045 A1 | 6/2005 | Sun et al. |
| 2005/0124564 A1 | 6/2005 | Binley et al. |
| 2005/0137329 A1 | 6/2005 | Holmes et al. |
| 2005/0142642 A1 | 6/2005 | Sun et al. |
| 2005/0143292 A1 | 6/2005 | Defrees et al. |
| 2005/0153879 A1 | 7/2005 | Svetina et al. |
| 2005/0158822 A1 | 7/2005 | Pecker |
| 2005/0158832 A1 | 7/2005 | Young et al. |
| 2005/0164301 A1 | 7/2005 | Kolkman et al. |
| 2005/0170457 A1 | 8/2005 | Pool et al. |
| 2005/0181359 A1 | 8/2005 | Optelten et al. |
| 2005/0181482 A1 | 8/2005 | Meade et al. |
| 2005/0192211 A1 | 9/2005 | Gillies et al. |
| 2005/0202538 A1 | 9/2005 | Gillies et al. |
| 2005/0221384 A1 | 10/2005 | Kolkman et al. |
| 2005/0227289 A1 | 10/2005 | Reilly et al. |
| 2005/0238646 A1 | 10/2005 | Ledbetter et al. |
| 2005/0244409 A1 | 11/2005 | Erickson-Miller et al. |
| 2005/0267027 A1 | 12/2005 | Lounsbury et al. |
| 2006/0040858 A1 | 2/2006 | Holmes et al. |
| 2006/0088906 A1 | 4/2006 | Defrees et al. |
| 2006/0111279 A1 | 5/2006 | Defrees et al. |
| 2006/0134116 A1 | 6/2006 | Rancourt et al. |
| 2006/0147379 A1 | 7/2006 | Bornhop et al. |
| 2006/0233794 A1 | 10/2006 | Law et al. |
| 2007/0082380 A1 | 4/2007 | Pardridge et al. |
| 2007/0224186 A1 | 9/2007 | Kulaksiz et al. |
| 2009/0032449 A1 | 2/2009 | Mueth et al. |
| 2009/0215095 A1 | 8/2009 | Lauth et al. |
| 2010/0111852 A1 | 5/2010 | Yoshida |
| 2010/0136015 A1 | 6/2010 | Lin et al. |
| 2010/0146650 A1 | 6/2010 | Goetsch et al. |
| 2010/0266644 A1 | 10/2010 | Helenek et al. |
| 2010/0285027 A1 | 11/2010 | Vaulont et al. |
| 2011/0059080 A1 | 3/2011 | Cornfeld et al. |
| 2011/0135663 A1 | 6/2011 | Zhang |
| 2011/0150888 A1 | 6/2011 | Foltz et al. |
| 2011/0293630 A1 | 12/2011 | Stitt et al. |
| 2012/0003696 A1 | 1/2012 | Kulaksiz et al. |
| 2012/0040894 A1 | 2/2012 | Ganz et al. |
| 2012/0082666 A1 | 4/2012 | Chen et al. |
| 2012/0114672 A1 | 5/2012 | Rohlff et al. |
| 2012/0177639 A1 | 7/2012 | Baurin et al. |
| 2012/0202229 A1 | 8/2012 | Lauth et al. |
| 2013/0130287 A1 | 5/2013 | Westerman et al. |
| 2014/0127229 A1 | 5/2014 | Luo et al. |
| 2015/0202224 A1 | 7/2015 | Bregman et al. |
| 2016/0017032 A1 | 1/2016 | Westerman et al. |
| 2016/0166649 A1 | 6/2016 | Nicolas et al. |
| 2017/0247448 A1 | 8/2017 | Westerman |
| 2017/0283495 A1 | 10/2017 | Westerman et al. |

FOREIGN PATENT DOCUMENTS

| | | |
|---|---|---|
| CN | 102112489 A | 6/2011 |
| CN | 104769426 A | 7/2015 |
| CN | 105263514 A | 1/2016 |
| EP | 0315456 A1 | 5/1989 |
| EP | 0404097 A2 | 12/1990 |
| EP | 1578254 B1 | 3/2013 |
| EP | 2109624 B1 | 7/2014 |
| EP | 2877848 A1 | 6/2015 |
| EP | 2968503 A2 | 1/2016 |
| EP | 3197915 A1 | 8/2017 |
| HK | 1114419 A1 | 1/2014 |
| JP | 2006517198 A | 7/2006 |
| JP | 2008533471 A | 8/2008 |
| JP | 2010517529 A | 5/2010 |
| JP | 2010539969 A | 12/2010 |
| JP | 2011502482 A | 1/2011 |
| JP | 2011519279 A | 7/2011 |
| JP | 2011530514 A | 12/2011 |
| RU | 2005119179 A | 1/2006 |
| RU | 02359268 | 6/2009 |
| WO | WO-8705330 A1 | 9/1987 |
| WO | WO-9105867 A1 | 5/1991 |
| WO | WO-9311161 A1 | 6/1993 |
| WO | WO-9505465 A1 | 2/1995 |
| WO | WO-9627011 A1 | 9/1996 |
| WO | WO-9966054 A3 | 4/2000 |
| WO | WO-0024893 A3 | 9/2000 |
| WO | WO-0061637 A1 | 10/2000 |
| WO | WO-0136489 A3 | 11/2001 |
| WO | WO-0214356 A2 | 2/2002 |
| WO | WO-0220034 A1 | 3/2002 |
| WO | WO-0181405 A3 | 5/2002 |
| WO | WO-02085940 A2 | 10/2002 |
| WO | WO-0249673 A3 | 1/2003 |
| WO | WO-0219963 A3 | 2/2003 |
| WO | WO-03041600 A1 | 5/2003 |
| WO | WO-03029291 A3 | 7/2003 |
| WO | WO-03055526 A2 | 7/2003 |
| WO | WO-03084477 A2 | 10/2003 |
| WO | WO-02085940 A3 | 11/2003 |
| WO | WO-03094858 A2 | 11/2003 |
| WO | WO-2004002424 A2 | 1/2004 |
| WO | WO-2004009627 A1 | 1/2004 |

(56) References Cited

FOREIGN PATENT DOCUMENTS

| WO | WO-2004018667 A1 | 3/2004 |
|---|---|---|
| WO | WO-2004024761 A1 | 3/2004 |
| WO | WO-2004058044 | 7/2004 |
| WO | WO-2004058044 A2 | 7/2004 |
| WO | WO-2004002417 A3 | 11/2004 |
| WO | WO-2004106373 A1 | 12/2004 |
| WO | WO-2004101611 A3 | 1/2005 |
| WO | WO-2005001136 A1 | 1/2005 |
| WO | WO-2005025606 A1 | 3/2005 |
| WO | WO-2005063808 A1 | 7/2005 |
| WO | WO-2005063809 A1 | 7/2005 |
| WO | WO-2004043382 A3 | 8/2005 |
| WO | WO-2005021579 A3 | 8/2005 |
| WO | WO-2005070451 A1 | 8/2005 |
| WO | WO-2004101606 A3 | 9/2005 |
| WO | WO-2005084711 A1 | 9/2005 |
| WO | WO-2005051327 A3 | 11/2005 |
| WO | WO-2006002646 A2 | 1/2006 |
| WO | WO-2004101600 A3 | 2/2006 |
| WO | WO-2004033651 A3 | 3/2006 |
| WO | WO-2005103076 A3 | 3/2006 |
| WO | WO-2006029094 A2 | 3/2006 |
| WO | WO-2004035603 A3 | 4/2006 |
| WO | WO-2005032460 A3 | 4/2006 |
| WO | WO-2005081687 A3 | 4/2006 |
| WO | WO-2006050959 A2 | 5/2006 |
| WO | WO-2005001025 A3 | 6/2006 |
| WO | WO-2005100403 A3 | 7/2006 |
| WO | WO-2007081744 A2 | 7/2007 |
| WO | WO-2005092369 A3 | 11/2007 |
| WO | WO-2008089795 A1 | 7/2008 |
| WO | WO-2008097461 A2 | 8/2008 |
| WO | WO-2009139822 A1 | 11/2009 |
| WO | WO-2010017070 A1 | 2/2010 |
| WO | WO-2010065815 A2 | 6/2010 |
| WO | WO-2011057744 A1 | 5/2011 |
| WO | WO-2014058516 A1 | 4/2014 |
| WO | WO-2014152006 A2 | 9/2014 |
| WO | WO-2016049036 A1 | 3/2016 |
| WO | WO-2018165186 A1 | 9/2018 |

OTHER PUBLICATIONS

Alleyne et al., Individualized treatment for iron deficiency anemia in adults, Am J Med, 121(11):943-948 2008.
Altschul et al., Gapped BLAST and PSI-BLAST: A new generation of protein database search programs. Nuc. Acids Res. 25: 3389-3402 (1997).
Altschul, S. F. et al., Basic local alignment search tool. J. Molec. Biol. 215: 403-410 (1990).
Samanen et al., Chemical approaches to improve the oral bioavailability of peptidergic molecules. J. Pharm. Pharmacol. 48:119-135 (1996).
Anker et al., Ferric carboxymaltose in patients with heart failure and iron deficiency. N Engl J Med 361:2436, 2009.
Aplin and Wriston, Preparation, properties, and applications of carbohydrate conjugates of proteins and lipid. CRC Crit. Rev. Biochem., pp. 259-306 (1981). .
Argarana et al., Molecular cloning and nucleotide sequence of the streptavidin gene. Nucleic Acids Res. 14(4):1871-82 (1986).
Ashby et al., Plasma hepcidin levels are elevated but responsive to erythropoietin therapy in renal disease. Kidney Int 75:976-81, 2009.
Aspuru et al., Optimal management of iron deficiency anemia due to poor dietary intake, Int J Gen Med, 4:741-750, 2011.
Auerbach and Adamson. How we diagnose and treat iron deficiency anemia. Am J Hematol 91:31, 2016.
Beshara et al. (2003) Pharmacokinetics abd red cell utilization of 52Fe/59Fe-labelled iron polymaltose in anaemic patients using positron emission tomography. Br J Haematol 120(5): 853-859, 2003.
Better et al., *Escherichia coli* secretion of an active chimeric antibody fragment. Science 240: 1041-1043, 1988.
Biocca et al. Expression and targeting of intracellular antibodies in mammalian cells. EMBO J 9:101-108 (1990).
Bregman et al. Hepcidin levels predict nonresponsiveness to oral iron therapy in patients with iron deficiency anemia. Am J Hematol 88:97, 2013.
Brennan et al., Preparation of bispecific antibodies by chemical recombination of monoclonal immunoglobulin fragments. Science 229:81, 1985.
Breymann et al., Comparative efficacy and safety of intravenous ferric carboxymaltose in the treatment of postpartum iron deficiency anemia. Int J Gynaecol Obstet 101:67, 2008.
Camaschella C. Iron deficiency: new insights into diagnosis and treatment. Hematology Am Soc Hematol Educ Program. 2015:8-13, 2015.
Caron et al., Engineered humanized dimeric forms of IgG are more effective antibodies. J. Exp Med. 176: 1191-1195, 1992.
Carpenter et al., Interactions of stabilizing additives with proteins during freeze-thawing and freeze-drying. In: Developments in Biological Standardization, 74:225-239 (1991).
Carrillo and Lipman, The Multiple sequence alignment problem in biology. SIAM J. Applied Math., 48(5): 1073 (1988).
Carter et al., High level *Escherichia coli* expression and production of a bivalent humanized antibody fragment. Bio/Technology 10:163-167 (1992).
Centers for Disease Control and Prevention (CDC). Recommendations to prevent and control iron deficiency in the United States. MMWR Recomm Rep 47:1-29, 1998.
Champe et al., Monoclonal antibodies that block the activity of Leukocyte function-associated Antigen 1 recognize three discrete epitopes in the inserted domain of CD11a. J. Biol. Chem. 270: 1388-1394 (1995).
Chen, Formation concerns of protein drugs. Drug Development and Industrial Pharmacy, vol. 18, Nos. 11 and 12, pp. 1311-1354 (1992).
Chothia and Lesk, Canonical structures for the hypervariable regions of immunoglobulins. J. Mol. Biol., 196: 901-917 (1987).
Clackson et al., Making antibody fragments using phage display libraries. Nature 352:624-628 (1991).
Clark, Iron deficiency anemia. Nutr Clin Pract 23:128-41, 2008.
Colby et al., Potent inhibition of huntingtin aggregation and cytotoxicity by a disulfide bond-free single-domain intracellular antibody. Proc Natl Acad Sci USA. 101:17616-21 (2004).
Cooke et al., A fully human anti-hepcidin antibody modulates iron metabolism in both mice and nonhuman primates Blood, 122:3054-3061 (2013).
Cotes and Bangham, Bio-assay of erythropoietin in mice made polycyth/emic by exposure to air at a reduced pressure. Nature 191:1065 (1961).
Coyne, Hepcidin: clinical utility as a diagnostic tool and therapeutic target. Kidney Int 80:240-4, 2011.
Crary SE et al. Intravenous iron sucrose for children with iron deficiency failing to respond to oral iron therapy. Pediatr Blood Cancer. 56(4):615-9, 2011.
Creighton, Proteins: Structures and Molecular Properties, W.H. Freeman & Co., San Francisco, pp. 79-86 (1983).
Cuijpers et al., Iron deficiency anaemia due to a matriptase-2-mutation. Nederlands Tijdschrift Voor Geneeskunde, 154:A1038 (2010).
Der-Balian et al., Fluorescein labeling of Fab' while preserving single thiol. Anal. Biochem. 173:59-63 (1988).
Devereux, J., et al., A comprehensive set of sequence analysis programs for the V A X. Nucleic Acids Research 12(1): 387 (1984).
Dobeli, et al., Recombinant fusion proteins for the industrial production of disulfide bridge containing peptides: Purification, oxidation without concatamer formation, and selective cleavage. Protein Expr. Purif. 12:404-414 (1998).
Edge et al., Deglycosylation of glycoproteins by trifluoromethanesulfonic acid. Anal. Biochem., 118: 131-137 (1981).
Edge et al., Total synthesis of a human leukocyte interferon gene. Nature, 292:756 (1981).
Sehgal D and Vijay IK, A method for the high efficiency of water-soluble carbodiimide-mediated amidation, Anal Biochem. 218(1):87-91 (1994).

(56) References Cited

OTHER PUBLICATIONS

Elhai, J. and Wolk, C. P., Conjugal transfer of DNA to cyanobacteria. In: Methods in Enzymology, vol. 167, 747-754,1988.
European Patent Application No. 13845830.2 Extended European Search Report dated Feb. 24, 2016.
European Patent Application No. 14771150.1 extended European Search report dated Jan. 18, 2017.
European Patent Application No. 14771150.1 partial supplementary European search report dated Oct. 21, 2016.
Fasano et al., Modifications of the iron-neuromelanin system in Parkinson's disease. J. Neurochem. 96:909-916 (2006).
Fix, Oral controlled release technology for peptides: Status and future prospects. Pharm Res. 13:1760-1764 (1996).
Fleming and Ponka, Iron overload in human disease. N Engl J Med 366:348-59, 2012.
Francis et al., PEGylation of cytokines and other therapeutic proteins and peptides: the importance of biological optimisation of coupling techniques. International Journal of Hematology 68:1-18, 1998.
Fredericks et al., Identification of potent human anti-IL-IR1 antagonist antibodies. Protein Engineering, Design & Selection, 17:95-106 (2004).
Freireich et al., The effect of inflammation on the utilization of erythrocyte and transferrin bound radioiron for red cell production. Blood 12:972-83 (1957).
Ganz and Nemeth, Iron imports. IV. Hepcidin and regulation of body iron metabolism. Am J Physiol Gastrointest Liver Physiol 290:G199-203 (2006).
Ganz and Nemeth, The hepcidin-ferroportin system as a therapeutic target in anemias and iron overload disorders. Hematology Am Soc Hematol. Education Program, 2011:538-542 (2011).
Ganz et al. Hepcidin and disorders of iron metabolism. Annu Rev Med 62:347-360 (2011).
Ganz et al., Immunoassay for human serum hepcidin. Blood, 112:4292-4297 (2008).
Geisser et al. Structure/histotoxicity relationship of parenteral iron preparations. Arzneimittelforschung 42: 1439-1452, 1992.
Gen Bank Accession No. BF583451, Jan. 2011.
Gen Bank Accession No. JN573653, Jan. 2012.
Gen Bank Accession No. MMU55552, Sep. 2001.
Gentry et al., Structural and biochemical characterization of CIB1 delineates a new family of EF-hand-containing proteins. J Biol Chem., 280(9): 8407-8415 (2005).
Gilles MA, Hudson AQ and Borders CL Jr, Stability of water-soluble carbodiimides in aqueous solution, Anal Biochem. 184(2):244-248 (1990).
Glazer and Stryer, Phycofluor probes. Trends Biochem. Sci. 9:423-7 (1984).
Goodnough et al., Detection, evaluation, and management of iron-restricted erythropoiesis. Blood 116:4754-61, 2010.
Goodnough, Iron deficiency syndromes and iron-restricted erythropoiesis. Transfusion. 52:1584-1592, 2012.
Green, Avidin. In Advances in Protein Chemistry. Academic Press, New York. 29, 85-133 (1975).
Green et al., The Use of bifunctional biotinyl compounds to determine the arrangement of subunits in Avidin. Biochem J. 125:781-791, 1971.
Green, NM., A spectrophotometric assay for avidin and biotin based on binding of dyes by avidin. Biochem. J. 94: 23c-24c. (1965).
Gruber et al., Efficient tumor cell lysis mediated by a bispecific single chain antibody expressed in *Escherichia coli*. J. Immunol. 152: 5368, (1994).
Guggenbuhl et al., Bone mineral density in men with genetic hemochromatosis and HFE gene mutation. Osteoporos. Int. 16:1809-1814 (2005).
Hakimuddin, et al. A chemical method for the deglycosylation of proteins. Arch. Biochem. Biophys. 259(1):52-57, 1987.
Shalaby et al., Development of humanized bispecific antibodies reactive with cytotoxic lymphocytes and tumor cells overexpressing the HER2 protooncogene. J. Exp. Med. 175:217-225 (1992).

Hardy, et al. Demonstartion of B-cell maturation in X-linked immunodeficient mice by simultaneous three-colour immunofluorescence. Nature 306:270-2 (1983).
Hardy RR et al. Murine B cell differentiation linegaes. J. Exp. Med. 159:1169-88 (1984).
Heeley, et al., Mutations flanking the polyglutamine repeat in the modulaory domain of rat glucocorticoid receptor lead to an increase in affinity for hormone. Endocr. Res. 28:217-229 (2002).
Heng et al., Making cell-permeable antibodies (Transbody) through fusion of protein transduction domains (PTD) with single chain variable fragment (scFv) antibodies: Potential advantages over antibodies expressed within the intracellular environment (Intrabody). Med Hypotheses. 64:1105-8 (2005).
Henry et al., Intravenous ferric gluconate significantly improves response to Epoetin Alfa versus oral iron or no iron in anemic patients with cancer receiving chemotherapy the Oncologist, 12:231-242 (2007).
Shields et al., Lack of fucose on human IgG1 N-linked oligosaccharide improves binding to human FcyRIII and antibody-dependent cellular toxicity. J Biol Chem. 277(30):26733-40 (2002).
Shinkawa et al., The absence of fucose but not in the presence of Galactose or biseting N-Acetylglucosamine of human IgG1 complex-type oligosaccharides shows the critical role of enhancing antibody-dependent cellular cytotoxicity. J Biol Chem. 278(5):3466-73 (2003).
Hollinger et al., Diabodies: Small bivalent and bispecific antibody fragments. Proc. Natl. Acad. Sci. USA 90:6444 6448 (1993).
Shopes, A genetically engineered human IgG mutant with enhanced cytolytic activity. J. Immunol. 148: 2918-2922 (1992).
Huston et al. Protein engineering of antibody binding sites: recovery of specific activity in an anti-digoxin single-chain Fv analogue produced in *Escherichia coli*. PNAS USA 85:5879-5883 (1988).
Jay et al., Chemical synthesis of a biologically active gene for human immune interferon-7. J. Biol. Chem., 259:6311-6317 (1984).
Jeong et al., Avimers hold their own. Nat. Biotechnol. 23(12):1493-1494 (2005).
Jones et al., Replacing the complementarity-determining regions in a human antibody with those from a mouse. Nature 321: 522-525 (1986).
Kabat et al., Sequences of Proteins of Immunological Interest, 5th Ed. Public Health Service, National Institutes of Health, Bethesda, Md. pp. 647-669, 1991.
Kaur et al., Does cellular iron dysregulation play a causative role in Parkinson's disease? Ageing Res. Rev., 3:327-343 (2004).
Kipriyanov et al., Single-chain antibody streptavidin fusions: Tetrameric bifunctional scFv-complexes with biotin binding activity and enhanced affinity to antigen. Hum Antibodies Hybridomas 6(3): 93-101 (1995).
Kohler et al., Continuous cultures of fused cells secreting antibody of predefined soecificity. Nature 256:495-97 (1975).
Kostelny et al., Formation of a bispecific antibody by the use of leucine zippers. J. Immunol. 148(5):1547-1553 (1992).
Kroll, A Multifunctional prokaryotic protein expression system: Overproduction, affinity purification and selective detection. DNA Cell. Biol. 12(5):441-453 (1993).
Kronick, MN and Grossman, PD, Immunoassay techniques with fluorescent phycobiliprotein conjugates. Clin. Chem. 29(9):1582-6 (1983).
Kronick,, The use of phycobiliproteins as fluorescent labels in immunoassay. J. Immuno. Meth. 92:1-13 (1986).
Kulnigg et al., A novel intravenous iron formulation for treatment of anemia in inflammatory bowel disease: the ferric carboxymaltose (FERINJECT) randomized controlled trial. Am J Gastroenterol 103:1182, 2008.
Lahn et al., Aerosolized anti-T-Cell-Receptor antibodies are effective against airway inflammation and hyperreactivity. Int. Arch. Allergy Immuno., 134: 49-55 (2004).
Landry et al. Pharmacokinetic study of ferumoxytol: a new iron replacement therapy in normal subjects and hemodialysis patients. Am J Nephrol 25(4), 400-410, 2005. (Abstract only).
Lanier, LL and Loken, MR, Human lymphocyte subpopulations identified by using three-color immunofluorescence and flow cytometry analysis: Correlation of Leu-2, Leu-3, Leu-7, Leu-8 and Leu-11 cell surface antigen expression. J. Immunol., 132(1):151-156 (1984).

(56) References Cited

OTHER PUBLICATIONS

Leatherbarrow et al., Effector functions of a monoclonal aglycosylated mouse IgG2a: Binding and activation of complement component C1 and interaction with human monocyte Fc receptor. Mol. Immunol. 22(4):407-415 (1985).

Liljeblad, et al., Analysis of agalacto-IgG in rheumatoid arthritis using surface plasmon resonance. Glyco. J. 17:323-329 (2000).

Macdougall et al., FIND-CKD: a randomized trial of intravenous ferric carboxymaltose versus oral iron in patients with chronic kidney disease and iron deficiency anaemia. Nephrol Dial Transplant 29:2075, 2014.

Mantadakis E . Advances in Pediatric Intravenous Iron Therapy. Pediatr Blood Cancer. 63(1):11-6, 2016.

Mantadakis et al., Intravenous iron sucrose for children with iron deficiency anemia: a single institution study. World J. Pediatrics, Online First, 5 pages, Mar. 2015.

Marks et al., By-passing immunization: Human antibodies from V-gene libraries displayed on phage. J. Mol. Biol. 222:581-597 (1991).

Mast et al., Clinical utility of the soluble transferrin receptor and comparison with serum ferritin in several populations. Clin Chem 44(1):45-51 (1998).

Mhashilkar et al., Inhibition of HIV-1 tat-mediated LTR transactivation and HIV-1 infection by anti-Tat single chain intrabodies. EMBO J 14:1542-51, (1995).

Moretti et al. Oral iron supplements increase hepcidin and decrease iron absorption from daily or twice-daily doses in iron-depleted young women. Blood, 126(17):1981-9, 2015.

Muraoka and Shulman, Structural requirements of the IgM assembly and cytolytic activity. Effects of mutations in the oligosaccharide acceptor site at Asn402. J. Immunol. 142(2):695-70 (1989).

Muyldermans et al., Sequence and structure of VH domain from naturally occurring camel heavy chain immunoglobulins lacking light chains. Protein Engineering 7(9):1129-1135, 1994.

Nakajima N and Ikade Y, Mechanism of amide formation by carbodiimide for bioconjugation in aqueous media, Bioconjugate Chem. 6(1):123-130 (1995).

Nambair et al., Total synthesis and cloning of a gene coding for the ribonuclease S protein. Science, 223(4642):1299-1301 (1984).

National Kidney Foundation. K/DOQI Clinical Practice Guidelines for Anemia of Chronic Kidney Disease, 2000. Am J Kidney Dis. 37(supp 1):S182-S238 (2001).

Nemeth et al. Hepcidin regulates cellular iron efflux by binding to ferroportin and inducing its internalization. Science 306:2090-2093 (2004).

Nemeth et al., The N-terminus of hepcidin is essential for its interaction with ferroportin: Structure-function study. Blood, 107(1):328-333, 2006.

Neri et al., High-affinity antigen binding by chelating recombinant antibodies (CRAbs). J Mol Biol. 246:367-73, (1995).

Nilsson K and Mosbach K. p-Toluenesulfonyl chloride as an activating agent of agarose for the preparation of immobilized affinity ligands and proteins. Eur. J. Biochem. 112: 397-402 (1980).

Noren et al., A General method for site-specific incorporation of unnatural amino acids into rpoteins. Science, 244(4901):182-188 (1989).

Sojar and Bahl, A Chemical method for the deglycosylation of proteins. Arch. Biochem. Biophys. 259(1): 52-57 (1987).

Olafsen, et al., Characterization of engineered anti-p185HER-2 (scFv-CH3)2 antibody fragments (minibodies) for tumor targeting. Protein Eng Des Sel. 17(4):315-23 (2004).

Onken et al., A multicenter, randomized, active-controlled study to investigate the efficacy and safety of intravenous ferric carboxymaltose in patients with iron deficiency anemia. Transfusion 54:306, 2014.

Osbourn et al., Directed selection of MIP-alpha neutralizing CCR5 antibodies from a phage display human antibody library. Nat. Biotechnol. 16:778 (1998).

Sox and Hood, Attachment of Carbohydrate to the variable region of myeloma immunoglobulin light chains. Proc. Natl. Acad. Sci. USA 66(3):975-982 (1970).

Pahler et al., Characterization and crystallization of core streptavidin. J Biol Chem 262(29):13933-13937 (1987).

Papanikolaou et al. Hepcidin in iron overload disorders. Blood 105:4103-4105 (2005).

Parks, et al. Three color immunofluorescence analysis of mouse B-Lymphocyte subpopulations. Cytometry 5:159-68 (1984).

Pasricha et al. Serum hepcidin as a diagnostic test of iron deficiency in premenopausal female blood donors. Haematologica 96(8):1099-1105, 2011.

PCT Patent Application No. PCT/US2013/052299 International Preliminary Report on Patentability dated Jan. 27, 2015.

PCT Patent Application No. PCT/US2013/052299 International Search Report dated Feb. 3, 2014.

PCT Patent Application No. PCT/US2013/052299 Written Opinion completed Jan. 15, 2014.

PCT Patent Application No. PCT/US2015/051469 International Search Report and Written Opinion dated Jan. 11, 2016.

PCT Patent Application No. PCT/US2016/063009 International Search Report and Written Opinion dated Feb. 7, 2017.

PCT Patent Application No. PCT/US2014/026804 International Preliminary Report on Patentability dated Sep. 15, 2015.

PCT Patent Application No. PCT/US2014/026804 International Search Report dated Oct. 3, 2014.

PCT Patent Application No. PCT/US2015/051469 International Preliminary Report on Patentabiloty dated Mar. 28, 2017.

Pietrangelo, Antonello. Hepcidin in human iron disorders: Therapeutic implications. Journal of Hepatology, 54(1):173-181, 2011.

Spinowitz et al. The safety and efficacy of ferumoxytol therapy in anemic chronic kidney disease patients. Kidney Intl 68:1801-1807, 2005.

Plückthun, A., Antibody engineering: Advances from the use of *Escherichia Coli* expression systems. Bio/Technology 9: 545-551 (1991).

Pluckthun, Chapter 11, Antibodies from *Escherichia coli* . in: The Handbook of Experimental Pharmacology, vol. 113 entitled The Pharmacology of Monoclonal Antibodies, Rosenburg and Moore eds. Springer-Verlag, New York, pp. 269-315 (1994).

Poli et al., Hepcidin antagonists for potential treatments of disorders with hepcidin excess. Frontiers in Pharmacology, 86(5):1-13, 2014.

Pospiilova et al., Significance of hepcidin level assessment in the diagnosis of selected types of anaemia in childhood. Transfuze A Hematologie Dnes, Czech Medical Association, J.E. Purkyne, 18(2):58-65, 2012.

Powers et al., Expression of single-chain Fv-Fc fusions in Pichia pastoris. Journal of Immunological Methods, 251:123-135 (2001).

Presta, Antibody Engineering. Curr. Op. Struct. Biol. 2: 593-596 (1992).

Qunibi et al., A randomized controlled trial comparing intravenous ferric carboxymaltose with oral iron for treatment of iron deficiency anaemia of non-dialysis-dependent chronic kidney disease patients. Nephrol Dial Transplant 26:1599-607, 2011.

Reff, M.E., High-level production of recombinent immunoglobulins in mammalian cells. Current Opinion in Bio. 4: 573-576 (1993).

Reichmann et al., Reshaping human antibodies for therapy. Nature 332(24): 323-329 (1988).

Reiter et al , Engineering antibody Fv fragments for cancer detection and therapy: Disulfide-stabilized Fv fragments. Nature Biotechnology 14:1239-1245 (1996).

Sanad et al., Obesity modulate serum hepcidin and treatment outcome of iron deficiency anemia in children: A case control study Italian Journal of Pediatrics, 37:34 (2011).

Sasu et al., Antihepcidin antibody treatment modulates iron metabolism and is effective in a mouse model of inflammation-induced anemia. Blood, 115(6):3616-3624, 2010.

Schrier SL. So you know how to treat iron deficiency anemia. Blood, 126:1971, 2015.

Semrin et al., Impaired intestinal iron absorption in Chron's Disease correlates with disease activity and markers of inflammation. Inflamm Bowel Disease, 12(12):1101-1106 (2006).

Silverman et al., Corrigendum: Multivalent avimer proteins evolved by exon shuffling of a family of human receptor domains. Nature Biotechnology, 24(2):220, 2006.

(56) References Cited

OTHER PUBLICATIONS

Silverman et al., Multivalent avimer proteins evolved by exon shuffling of a family of human receptor domains. Nat. Biotechnol. 23 (12):1556-1561 (2005).
Skerra et al. Assembly of a functional Immunoglobulin Fv fragment in *Escherichia coli*. Science 240(4855)1038-1041 (1988).
Steinmetz et al., Clinical experience with ferric carboxymaltose in the treatment of cancer- and chemotherapy-associated anaemia. Ann Oncol 24:475, 2013.
Tao and Morrison, Studies of Aglycosylated chimeric mouse-human IgG, J. Immunol. 143(8):2595-2601 (1989).
Taylor and Wall, Selective removal of alpha heavy-chain glycosylation sites causes immunoglobulin A degradation and reduced secretion. Mol. Cell. Biol. 8(10):4197-4203 (1988).
Thotakura et al., Enzymatic deglycosylation of glycoproteins. Chapter 28 in Meth. Enzymol. 138: 350 (1987).
Trill et al., Production of monoclonal antibodies in COS and CHO cells. Curr. Opinion Biotech 6: 553-560, 1995.
Studier. Protein production by auto-induction in high-density shaking ciltures. Protein Expr Purif. 41(1):207-234, 2005.
Umana et al., Engineered glycoforms of an antineuroblastoma IgG1 with optimized antibody-dependent cellular cytotoxic activity. Nat Biotechnol. 17:176-180, 1999.
U.S. Appl. No. 14/417,369 Office Action dated Jul. 31, 2017.
U.S. Appl. No. 14/417,369 Restriction Requirement dated Mar. 22, 2017.
U.S. Appl. No. 14/771,135 Office Action dated Jan. 9, 2017.
U.S. Appl. No. 14/771,135 Office Action dated Sep. 7, 2016.
U.S. Appl. No. 14/771,135 Restriction Requirement dated Feb. 26, 2016.
U.S. Appl. No. 15/485,141 Office Action dated Aug. 9, 2017.
Van Wyck et al. Making sense: A scientific approach to intravenous iron therapy. J Am Soc Nephrol 15:S91-S92, 2004.
Van Wyck et al. A randomized, controlled trial comparing IV iron sucrose to oral iron in anemic patients with nondialysis-dependent CKD. Kidney International, 68:2846-2856, 2005.
Van Wyck et al. Intravenous ferric carboxymaltose compared with oral iron in the treatment of postpartum anemia: a randomized controlled trial. Obstet Gynecol 110:267, 2007.
Van Wyck et al., Large-dose intravenous ferric carboxymaltose injection for iron deficiency anemia in heavy uterine bleeding: a randomized, controlled trial. Transfusion 49:2719, 2009.
Weinstein et al., Inappropriate expression of hepcidin is associated with iron refractory anemia: implications for the anemia of chronic disease Blood, 100(10):3776 (2002).
Weiss and Goodnough, Anemia of chronic disease. N Engl J Med 352:1011-23, 2005.
Wheeler et al., Intrabody-based strategies for inhibition of vascular endothelial growth factor receptor-2: effects on apoptosis, cell growth, and angiogenesis. The FASEB J., 17:1733-5 (2003).
Williams and Polli, The Lyophilization of pharmaceuticals: A Literature Review. Journal of Parenteral Science and Technology, 38(2):48-59 (1984).
Williams, et al., Dissection of the extracellular human interferon y receptor alpha-Chain into two immunoglobulin-like domains. Production in an *Escherichia coli* thioredoxin gene fusion expression system and recognition by neutralizing antibodies. Biochemistry 34:1787-1797 (1995).

Wish et al., Assessing Iron Status: Beyond Serum Ferritin and Transferring Saturation, Clin J Am Soc Nephrol, 1:S4-S8, 2006.
Szajani B et al, Effects of carbodiimide structure on the immobilization of enzymes, Appl Biochem Biotechnol. 30(2):225-231 (1991).
Zapata et al. Engineering linear F(ab')2 fragments for efficient production in *Escherichia coli* and enhanced antiproliferative activity. Protein Eng. 8(10):1057-1062 (1995).
Zaritsky et al., Hepcidin—a potential novel biomarker for iron status in chronic kidney disease. Clin J Am Soc Nephrol 4:1051-6, 2009.
Szczech et al., Comparison of high dose carboxymaltose to oral or IV iron in subjects with iron deficiency anemia not suitable for oral iron. Amer Soc Nephrol 22:435A, 2011.
Zhu et al., Evaluation and treatment of Iron deficiency Anemia: A Gastroenterological Perspective, 55:548-559, 2010.
Arezes et al., Hepcidin-induced hypoferremia is a critical host defense mechanism against the siderophilic bacterium vibrio vulnificus. Cell Host Microb., 17(1):47-57, 2015. (Author manuscript, 23 pages).
Casals-Pascual et al., Hepcidin demonstrates a biphasic association with anemia in acute Plasmodium falciparum malaria. Haematologica 97(11):1695-1698, 2012.
European Patent Application No. 14771150.1 Communication dated Sep. 14, 2017.
Ganz and Nemeth, Iron sequestration and anemia of inflammation. Seminars in Hematology, 46(4):387-393, Oct. 2009.
Handbook of Therapeutic Antibodies. Stephan Duebel, editor. Chapter 6, p. 119-144, 2007. XP007913671.
Michels et al., Hepcidin and host defense against infectious diseases. PLOS Pathogens, 11(8):e1004998, 14 pages, Aug. 20, 2015.
Preza et al., Minihepcidins are rationally designed small peptides that mimic hepcidin activity in mice and may be useful for the treatment of iron overload. The Journal of Clinical Investigation, 121(12):4880-4888, 2011.
Kroot et al. Hepcidin in human iron disorders: diagnostic implications. Clin Chem 57(12):1650-1669 (2011).
Lyseng-Williamson et al. Ferric Carboxymaltose: A Review of its Use in Iron-Deficiency Anaemia. Drugs 69(6):739-756 (2009).
PCT/US2018/021189 International Search Report and Written Opinion dated Jun. 8, 2018.
U.S. Appl. No. 14/417,369 Office Action dated May 30, 2018.
Young et al. Hepcidin for Clinicians. Clin J Am Soc Nephrol. 4(8):1384-1387 (2009).
Biosafety in Microbiological and Biomedical Laboratories, 5th Ed. (2009). HHS Publication No. (CDC) 21-1112.
Camaschella. Iron-deficiency anemia. N Engl J Med. 372(19):1832-1843 (2015).
European Patent Application No. 16869122.8 Extended European Search Report dated Aug. 14, 2018.
Galesloot et al. Serum hepcidin: reference ranges and biochemical correlates in the general population. Blood 117(25):e218-e225 (2011).
Ganz. Systemic iron homeostasis. Physiol Rev. 93(4):1721-1741 (2013).
Kautz et al. Erythroferrone contributes to recovery from anemia of inflammation. Blood 124:2569-2574 (2014).
U.S. Appl. No. 15/511,596 Office Action dated Sep. 17, 2018.
Young et al., Serum hepcidin is significantly associated with iron absorption from food and supplemental sources in healthy young women. Am J Clin Nutr. 533-538 (2009).

FIGURE 1

| MAb | Antigen Sequence | SEQ ID | Hapten | Carrier Protein |
|---|---|---|---|---|
| H32 | H-DTHFPICIFCCGCCHRSKCGMCCKT | SEQ ID NO: 19 | None | KLH |
| 583 | DNP-DTHFPIC(KLH-SMCC)-IF | SEQ ID NO: 27 | DNP | KLH |
| 1B1 | H-DTHFPICIFCCGCCHRSKCGMCCKT | SEQ ID NO: 19 | None | KLH |

FIGURE 2

|   | 1 | 2 | 3 | 4 | 5 | 6 | 7 | 8 | 9 | 10 | 11 | 12 |
|---|---|---|---|---|---|---|---|---|---|---|---|---|
| A | 0.0316 | 0.0397 | 0.0621 | 0.0748 | 0.0294 | 1.4366 | 0.983 | 0.1202 | 0.2161 | 0.0863 | 0.0276 | 0.2953 |
| B | 0.1691 | 0.8033 | 0.151 | 0.1495 | 0.1171 | 1.7579 | 0.1477 | 0.4895 | 0.656 | 0.1086 | 0.1306 | 1.0178 |
| C | 0.1414 | 0.0256 | 0.1288 | 0.1836 | 0.6374 | 0.3972 | 3.0077 | 0.4609 | 0.9864 | 1.7273 | 0.1515 | 0.7289 |
| D | 0.0414 | 0.8768 | 0.1091 | 0.7626 | 0.0691 | 0.9005 | 1.1272 | 0.3896 | 4 | 0.0592 | 0.4963 | 0.0303 |
| E | 0.7574 | 0.858 | 0.1177 | 0.1094 | 0.2217 | 0.5791 | 1.2748 | 0.0647 | 4 | 0.1971 | 0.6121 | 0.4396 |
| F | 0.6264 | 0.1013 | 0.9305 | 0.4412 | 0.0614 | 0.029 | 1.1897 | 0.5904 | 4 | 1.5156 | 0.0505 | 1.4848 |
| G | 0.1239 | 0.5561 | 0.2636 | 0.7668 | 0.0616 | 0.1464 | 1.0216 | 2.8072 | 2.4815 | 0.0387 | 0.0674 | 4 |
| H | 0.6497 | 0.1992 | 1.4523 | 0.4341 | 0.6312 | 0.4159 | 0.1403 | 0.8043 | 1.3596 | 0.6215 | 0.8331 | 0.0851 |

FIGURE 3

|   | 1 | 2 | 3 | 4 | 5 | 6 | 7 | 8 | 9 | 10 | 11 | 12 |
|---|---|---|---|---|---|---|---|---|---|---|---|---|
| A | 0.0144 | 0.0156 | 0.0115 | 0.0129 | 0.0179 | 0.4297 | 0.0855 | 0.0176 | 0.0435 | 0.0136 | 0.0122 | 0.138 |
| B | 0.0186 | 0.06 | 0.0119 | 0.0136 | 0.0118 | 0.0226 | 0.0227 | 0.1397 | 0.1478 | 0.0145 | 0.0114 | 0.0195 |
| C | 0.0182 | 0.013 | 0.0141 | 0.0271 | 0.0565 | 0.12 | 0.1068 | 0.0529 | 0.3228 | 0.4153 | 0.059 | 0.2724 |
| D | 0.0237 | 0.3614 | 0.0139 | 0.0637 | 0.0247 | 0.3583 | 0.2698 | 0.0188 | 4 | 0.015 | 0.0473 | 0.0208 |
| E | 0.2106 | 0.4298 | 0.0143 | 0.0134 | 0.1068 | 0.1188 | 0.231 | 0.0127 | 1.5338 | 0.0174 | 0.0422 | 0.193 |
| F | 0.1849 | 0.0166 | 0.4537 | 0.1855 | 0.0133 | 0.0134 | 0.8792 | 0.0152 | 0.6409 | 0.2137 | 0.02 | 0.2073 |
| G | 0.0163 | 0.167 | 0.0166 | 0.3013 | 0.013 | 0.0234 | 0.0131 | 0.4921 | 0.0364 | 0.0146 | 0.0233 | 0.3628 |
| H | 0.0199 | 0.0222 | 0.0378 | 0.0725 | 0.0192 | 0.0492 | 0.0205 | 0.1917 | 0.013 | 0.0216 | 0.227 | 0.0177 |

FIGURE 4

|  | Tracer Only | | Tracer + Hepcidin-25 | |
|---|---|---|---|---|
| 4A4 | 0.1964 | 0.1482 | 0.0578 | 0.0803 |
| 4B1 | 1.0983 | 1.1602 | 0.0606 | 0.0499 |
| 4B2 | 0.1345 | 0.1242 | 0.028 | 0.0589 |
| 4D1 | 0.0487 | 0.0646 | 0.0337 | 0.0508 |
| 5A3 | 3.403 | 3.458 | 0.069 | 0.083 |
| 5A4 | 2.4705 | 2.5002 | 0.0806 | 0.0664 |
| Positive | 0.418 | 0.4116 | 0.0886 | 0.0992 |
| Negative | 0.073 | 0.0507 | 0.0623 | 0.0817 |

FIGURE 5

| Characteristic | MAb 583 | MAb 1B1 | MAb H32 |
|---|---|---|---|
| Antigen | SEQ ID NO: 27 | SEQ ID NO: 19 | SEQ ID NO: 19 |
| Hapten | DNP | None | None |
| Carrier Protein | KLH | KLH | KLH |
| # Immunizations | 4 | 5 | 2 |
| Serum titer | 6400 | 6400 | 400 |
| # Mice for Fusion | 2 | 2 | 3 |
| Tissue for Fusion (Spleen, Lymph Node) | S, LN | S, LN | LN |
| Day of fusion | 87 | 106 | 11 |
| Total Hybridomas Evaluated | 1555/1728 = 90% | 2201/2304 = 95.5% | 768/960 = 80% |
| % Positive Hybridomas on Neutravidin | 12 | 17 | 7.4 |
| % Positive Hybridomas on anti-mouse Fc | 13.7 | 8 | not done |
| % IgG isotype | 12 | 25 | 50 |
| Number of Functional IgG MAbs | 1 | 1 | 1 |
| % Functional MAbs Discovered | 0.06 | 0.05 | 0.01 |

FIGURE 6

| Antigen | | # Hybridomas | # Functional MAbs | % Success |
|---|---|---|---|---|
| Hepcidin-25-KLH | | 960 | 1 (H32) | 0.1 |
| Hepcidin-25-Blue Carrier Protein | | 877 | 0 | 0 |
| Hepcidin-5-KLH | | 1600 | 0 | 0 |
| Hepcidin-5-KLH | | 850 | 0 | 0 |
| DNP-Hepcidin-25-KLH | | 1502 | 0 | 0 |
| DNP-Hepcidin-9-KLH | | 1555 | 1 (583) | 0.06 |
| Hepcidin-25-KLH | | 2201 | 1 (1B1) | 0.05 |
| Hepcidin-20-KLH | | 2300 | 0 | 0 |
| | Total | 11,845 | 3 | 0.025 |

1. Molecular Mass Markers (kDa, Invitrogen, #LC5925
2. Hepcidin-25
3. Hepcidin-22
4. Hepcidin-20
5. Protegrin
6. Molecular Mass Markers 1. Molecular Mass Markers (kDa, Invitrogen, # LC5925)
2. Hepcidin-25
3. Hepcidin-20
4. K18-Biotin hepcidin-25
5. K24-Biotin hepcidin-25
6. NT-Biotin hepcidin-25

FIGURE 13

|  | Ka (1/Ms) | Kd (1/s) | Rmax (RU) | RI (RU) | Conc. of analyte(nm) |
|---|---|---|---|---|---|
| 5 μg/ml 583 to NT-biotin-Hepcidin-25 | 1.33e6 | 2.43e-5 | 0.0306 | 127 | 33.5 |
| 5 μg/ml 583 to K18-biotin-Hepcidin-25 | 1.88e6 | 1.4e-5 | 4.1e-3 | 187 | 33.5 |

|  | KA (1/M) | KD (M) | Req (RU) | Kobs (1/s) | Chi2 |
|---|---|---|---|---|---|
|  |  |  |  |  | 1.24 |
| 5 μg/ml 583 to NT-biotin-Hepcidin-25 | 5.47e10 | 1.83e-11 | 0.0305 | 0.0445 |  |
| 5 μg/ml 583 to K18-biotin-Hepcidin-25 | 1.34e11 | 7.45e-12 | 4.1e-3 | 0.063 |  |

FIGURE 28

| One Way Analysis of Variance | | Friday, April 20, 2012, 4:31:06 PM | | | |
|---|---|---|---|---|---|
| Normality Test (Shapiro-Wilk) | | Passed | (P = 0.216) | | |
| Equal Variance Test: | | Passed | (P = 0.360) | | |
| | | | | | |
| Group Name | N | Missing | Mean | Std Dev | SEM |
| PBS + 50µg hepcidin-25 | 8 | 0 | 23.263 | 8.504 | 3.007 |
| Mab583 (1 dose) | 8 | 0 | 29.811 | 5.596 | 1.979 |
| Mab 583 (2 doses) | 8 | 0 | 40.540 | 16.733 | 5.916 |
| Sham Mab | 8 | 0 | 34.507 | 10.569 | 3.737 |
| PBS + no hepcidin | 8 | 0 | 43.001 | 11.812 | 4.176 |
| | | | | | |
| Source of Variation | DF | SS | MS | F | P |
| Between Groups | 4 | 2053.126 | 513.282 | 4.043 | 0.008 |
| Residual | 35 | 4443.971 | 126.971 | | |
| Total | 39 | 6497.098 | | | |

The differences in the mean values among the treatment groups are greater than would be expected by chance; there is a statistically significant difference (P = 0.008).
Power of performed test with alpha = 0.050: 0.748
Multiple Comparisons versus Control Group (Holm-Sidak method):
Overall significance level = 0.05
Comparisons for factor:

| Comparison | Diff of Means | t | Unadjusted P | Critical Level | Significant? |
|---|---|---|---|---|---|
| PBS+hepcidin-25 vs. PBS+no hepcidin | 19.739 | 3.503 | 0.001 | 0.013 | Yes |
| PBS+hepcidin-25 vs. Mab 583 (2 doses) | 17.277 | 3.067 | 0.004 | 0.017 | Yes |
| PBS+hepcidin-25 vs. Sham Mab | 11.244 | 1.996 | 0.054 | 0.025 | No |
| PBS+hepcidin-25 vs. Mab583 (1 dose) | 6.548 | 1.162 | 0.253 | 0.050 | No |

ANTI-HEPCIDIN ANTIBODIES AND USES THEREOF

CROSS REFERENCE

This application is a continuation of U.S. application Ser. No. 15/485,141, filed Apr. 11, 2017, which is a divisional of U.S. application Ser. No. 14/771,135, filed Aug. 27, 2015, now U.S. Pat. No. 9,657,098, which is a U.S. National Stage Entry of PCT/US2014/026804 filed Mar. 13, 2014, which claims the benefit of U.S. Provisional Application No. 61/791,953, filed Mar. 15, 2013, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 31, 2017, is named 44546-702.301_SL.txt and is 38,155 bytes in size.

BACKGROUND OF THE INVENTION

Iron is an essential trace element required for growth and development of living organisms. In mammals, iron content is regulated by controlling iron absorption, iron recycling, and release of iron from the cells in which it is stored. Iron is predominantly absorbed in the duodenum and upper jejunum by enterocytes. Iron is recycled from degraded red cells by reticuloendothelial macrophages in bone marrow, hepatic Kupffer cells and spleen. Iron release is controlled by ferroportin, a major iron export protein located on the cell surface of enterocytes, macrophages and hepatocytes, the main cells capable of releasing iron into plasma. Hepcidin binds to ferroportin and decreases its functional activity by causing it to be internalized from the cell surface and degraded. (Nemeth et al., *Science,* 306:2090-3, 2004).

SUMMARY OF THE INVENTION

Provided herein are antibodies and antigen-binding fragments thereof that bind to hepcidin (Hep) or a hepcidin peptide. In one aspect, provided herein is an antibody, or antigen-binding fragment thereof, that specifically binds to the N-terminus of hepcidin or a hepcidin peptide and neutralizes the activity of hepcidin in vitro and/or in vivo.

In one aspect, provided herein is an antibody, or antigen-binding fragment thereof, that specifically binds to hepcidin or a hepcidin peptide, comprising a heavy chain variable region and a light chain variable region,
wherein said heavy chain variable region comprises:
(i) a CDR1 having an amino acid sequence of any one of SEQ ID NOS: 55-57,
(ii) a CDR2 having an amino acid sequence of any one of SEQ ID NOS: 58-60, and
(iii) a CDR3 having an amino acid sequence of any one of SEQ ID NOS: 61-63;
and said light chain variable region comprises:
(i) a CDR1 having an amino acid sequence of any one of SEQ ID NOS: 64-66,
(ii) a CDR2 having an amino acid sequence of any one of SEQ ID NOS: 67-69, and
(iii) a CDR3 having an amino acid sequence of any one of SEQ ID NOS: 70-72.

In one aspect, provided herein is an antibody, or antigen-binding fragment thereof, that specifically binds to hepcidin or a hepcidin peptide, comprising a heavy chain variable region and a light chain variable region,
wherein said heavy chain variable region comprises:
(i) a CDR1 having an amino acid sequence encoded by any one of SEQ ID NOS: 1-3,
(ii) a CDR2 having an amino acid sequence encoded by any one of SEQ ID NOS: 4-6, and
(iii) a CDR3 having an amino acid sequence encoded by any one of SEQ ID NOS: 7-9;
and said light chain variable region comprises:
(i) a CDR1 having an amino acid sequence encoded by any one of SEQ ID NOS: 10-12,
(ii) a CDR2 having an amino acid sequence encoded by any one of SEQ ID NOS: 13-15, and
(iii) a CDR3 having an amino acid sequence encoded by any one of SEQ ID NOS: 16-18.

In one aspect, an antibody, or antigen-binding fragment thereof, provided herein comprises IgG1 or an IgG4 variable heavy chain and variable light chain.

In one aspect, provided herein is an antibody, or antigen-binding fragment thereof, that specifically binds to hepcidin or a hepcidin peptide, that is prepared by injecting a rodent (i.e., mouse, rat or rabbit) with a peptide having an amino acid sequence of any one of SEQ ID NOS: 19-27. In another embodiment, the peptide is conjugated to a carrier (e.g., keyhole limpet hemocyanin (KLH)) or administered with an adjuvant (complete Freund's adjuvant (CFA) or incomplete Freund's adjuvant (IFA)). In another embodiment the peptide is conjugated to a hapten (e.g., dinitrophenol [DNP]) and a carrier.

A hepcidin peptide to which an antibody, or antigen-binding fragment thereof, binds may have, in some instances, an amino acid sequence of SEQ ID NO: 19.

Provided herein is an antibody, or antigen-binding fragment thereof, that specifically binds to an epitope comprising amino acid sequence of any one of Hep-5, Hep-9, Hep-20, Hep 22 and Hep25.

In one embodiment, the antibody, or antigen-binding fragment thereof, specifically binds to an epitope comprising an amino acid sequence of Hep-20 (SEQ ID NO: 22), Hep 22 (SEQ ID NO: 23) and Hep25 (SEQ ID NO: 19).

In one embodiment, the antibody, or antigen-binding fragment thereof, specifically binds to an epitope comprising Hep-5 (SEQ ID NO: 25) or Hep-9 (SEQ ID NO: 24). In another embodiment, provided herein is an antibody, or antigen-binding fragment thereof, that specifically binds to an epitope comprising amino acid residues 1-9 of hepcidin. In another embodiment, the antibody, or antigen-binding fragment thereof, specifically binds to 2, 3, 4, 5, 6, 7, 8, or 9 amino acid residues of an epitope comprising amino acid residues 1-9 of hepcidin.

In another embodiment, the antibody, or antigen-binding fragment thereof, is monoclonal antibody comprising a heavy chain CDR1 encoded by SEQ ID NO: 55, a heavy CDR2 encoded by SEQ ID NO: 58, a heavy chain CDR3 encoded by SEQ ID NO: 61, a light chain CDR1 encoded by SEQ ID NO: 64, a light CDR2 encoded by SEQ ID NO: 67, and a light chain CDR3 encoded by SEQ ID NO: 70.

In another embodiment, the antibody, or antigen-binding fragment thereof, is monoclonal antibody comprising a heavy chain CDR1 encoded by SEQ ID NO: 56, a heavy CDR2 encoded by SEQ ID NO: 59, a heavy chain CDR3 encoded by SEQ ID NO: 61, a light chain CDR1 encoded by SEQ ID NO: 65, a light CDR2 encoded by SEQ ID NO: 68, and a light chain CDR3 encoded by SEQ ID NO: 71.

In another embodiment, the antibody, or antigen-binding fragment thereof, is monoclonal antibody comprising a heavy chain CDR1 encoded by SEQ ID NO: 57, a heavy CDR2 encoded by SEQ ID NO: 60, a heavy chain CDR3 encoded by SEQ ID NO: 63, a light chain CDR1 encoded by SEQ ID NO: 66, a light CDR2 encoded by SEQ ID NO: 69, and a light chain CDR3 encoded by SEQ ID NO: 72.

The antibody may be, for example, a monoclonal antibody, a chimeric antibody, a human antibody, or a humanized antibody. In one embodiment, a humanized variable heavy chain comprises an amino acid sequence set forth as SEQ ID NO: 40. In another embodiment, a humanized variable light chain comprises an amino acid sequence set forth as SEQ ID NO: 38.

In one aspect, provided herein is an antibody, or antigen-binding fragment thereof, comprises a heavy chain variable region framework region; and a light chain variable region framework region as set forth in the Sequence Listing below where the CDRs identified in any one of SEQ ID NOS: 1-18 are inserted into the framework region utilizing Kabat numbering.

The antigen-binding fragment may be, for example, a Fab fragment, a Fab' fragment, a F(ab')2 fragment, an Fv fragment, an scFv fragment, a single chain binding polypeptide, a Fd fragment, a variable heavy chain, a variable light chain or a dAb fragment. An antigen-binding fragment may be, for example, an AVIMER, a diabody, or a heavy chain dimer. A heavy chain dimer may be, for example, a camelid or a shark heavy chain construct.

An antibody, or antigen-binding fragment thereof, described herein may have a dissociation constant (Kd) of about 1 to about 10 pM, from about 10 to about 20 pM, from about 1 to about 29 pM, from about 30 to about 40 pM, from about 10 to about 100 pM, or from about 20 to about 500 pM.

An antibody, or antigen-binding fragment thereof, described herein may have a dissociation constant (Kd) of less than about 500 pM, less than about 400 pM, less than about 300 pM, less than about 200 pM, less than about 100 pM, less than about 75 pM, less than about 50 pM, less than about 30 pM, less than about 25 pM, less than about 20 pM, less than about 18 pM, less than about 15 pM, less than about 10 pM, less than about 7.5 pM, less than about 5 pM, less than about 2.5 pM, or less than about 1 pM.

An antibody, or antigen-binding fragment thereof, described herein may have an affinity for hepcidin or a hepcidin peptide of from about $10^{-9}$ to about $10^{-14}$, from about $10^{-10}$ to about $10^{-14}$, from about $10^{-11}$ to about $10^{-14}$, from about $10^{-12}$ to about $10^{-14}$, from about $10^{-13}$ to about $10^{-14}$, from about $10^{-10}$ to about $10^{-11}$, from about $10^{-11}$ to about $10^{-12}$, from about $10^{-12}$ to about $10^{-13}$, or $10^{-13}$ to about $10^{-14}$.

Provided herein is a composition, comprising an antibody, or antigen-binding fragment, described herein, and an acceptable carrier or excipient.

Also provided herein is an isolated nucleic acid molecule comprising a nucleotide sequence that encodes an antibody, or antigen-binding fragment thereof, described herein. Also provided herein is an expression vector comprising the nucleic acid molecule, operably linked to a regulatory control sequence. Also provided herein is a host cell comprising a vector or a nucleic acid molecule provided herein. Also provided herein is a method of using the host cell to produce an antibody, comprising culturing the host cell under suitable conditions such that the nucleic acid is expressed to produce the antibody.

Provided herein are therapeutic methods utilizing an antibody or antigen-binding fragment thereof, described herein. In one aspect, provided herein is a method of treating a disorder of iron homeostasis in a subject in need thereof, comprising administering to said subject a composition described herein. In another aspect, provided herein is a method of modulating hepcidin activity in a subject in need thereof, comprising administering to said subject a composition described herein. In yet another aspect, provided herein is a method for treating a disorder of iron homeostasis in a subject in need thereof, comprising administering to said subject a composition described herein. In yet another aspect, provided herein is a method of treating hemochromatosis in a subject in need thereof, comprising administering to said subject a composition described herein. In yet another aspect, provided herein is a method of treating a subject with pathologically or inappropriately elevated levels of hepcidin (inappropriately elevated relative to body and plasma iron stores), comprising administering to said subject a pharmaceutical composition described herein. In yet another aspect, provided herein is a method of treating anemia in a subject in need thereof, comprising administering to said subject a composition described herein. In yet another aspect, provided herein is a method of treating or reducing inflammation in a subject in need thereof, comprising administering to said subject a composition described herein. In one embodiment, inflammation to be treated or reduced is chronic inflammation. In yet another aspect, provided herein is a method of treating an inflammatory disease in a subject in need thereof, comprising administering to said subject a composition described herein. In yet another aspect, provided herein is a method of treating an infection in a subject in need thereof, comprising administering to said subject a composition described herein. An infection may be, for example, a bacterial, fungal, or viral infection. In yet another aspect, provided herein is a method of treating Iron refractory iron deficiency anemia (IRIDA). In yet another aspect, provided herein is a method of treating Anemia of Inflammation (AI) and Anemia of Chronic Disease (ACD). In yet another aspect, provided herein is a method of treating chronic kidney disease (CKD). In yet another aspect, provided herein is a method of treating cancer and Chemotherapy Induced Anemia (CCIA) which are associated with elevated hepcidin. In yet another aspect, provided herein is a method of treating neuro-inflammatory diseases which are associated with elevated hepcidin.

Any of such methods may, in some instances, further comprise administering to said subject one or more erythropoiesis stimulators. Erythropoiesis stimulators include, but are not limited to, erythropoietin, an erythropoietin variant, an erythropoiesis stimulating agent (ESA; such as, for example, Epoetin alfa [e.g., Procrit®, Epogen®, etc.], Epoetin beta [e.g., NeoRecormon, etc.], Darbepoetin alfa [e.g., Aranesp®, etc.], Methoxy polyethylene glycol-epoetin beta [e.g., Mircera®, etc.], etc.), a hypoxia inducible factor (HIF) prolyl hydroxylase inhibitor, a bone marrow derived erythroid factor (e.g. erythroferrone), a mini-hepcidin peptide (see, e.g., U.S. Publication No. 20120040894, by Ganz et al., which is incorporated herein by reference), an antisense inhibitor of hepcidin (see, e.g., U.S. Publication No. 20100136015, by Lin and Babitt., which is incorporated herein by reference), a siRNA inhibitor of hepcidin (Id.), miRNA inhibitor of hepcidin(Id.), an anti-BMP-2 antibody (Id.), an anti-BMP-4 antibody (Id.), an anti-BMP-6 antibody (Id.), a small molecule inhibitor (Id.), an anti-IL-6 antibody (see, e.g., U.S. Publication No. 20110059080, by Cornfeld et al., which is incorporated herein by reference), an anti-TNF-alpha antibody, methotrexate, an anti-inflammatory agent (e.g., a steroid [e.g., a corticosteroid, etc.]; a non-steroidal inflammatory drug [NSAID; e.g., aspirin, ibuprofen, naproxen, a cyclooxygenase (COX) enzyme inhibitor, etc.], a hormone (e.g. testosterone), or an immune selective anti-inflammatory derivative [ImSAID; e.g., tripeptide FEG (Phe-Glu-Gly) and its D-isomer feG]), hemojuvelin, an antibody that binds erythropoietin, and combinations thereof. In one embodiment, the antibody, or antigen-binding fragment thereof, that specifically binds hepcidin and the erythropoiesis stimulator are administered concurrently or sequentially.

Administration of a composition herein may be by any suitable means including, but not limited to, injection. In one embodiment, injection may be, for example, intravenous, subcutaneous, intramuscular injection, or spinal injection into the cerebrospinal fluid (CSF).

Provided herein is a container means comprising a composition described herein. The container means may be any suitable container which may house a liquid or lyophilized composition including, but not limited to, a vial, syringe, bottle, an in intravenous (IV) bag or ampoule. A syringe may be able to hold any volume of liquid suitable for injection into a subject including, but not limited to, 0.5 cc, 1 cc, 2 cc, 5 cc, 10 cc or more.

Provided herein are kits, comprising a composition or compositions described herein. In one aspect, provided herein is a kit for treating a disorder associated with elevated hepcidin levels or a disorder of iron homeostasis, comprising an antibody, or an antigen-binding fragment thereof, as described herein and an erythropoiesis stimulator. It would be understood, in some instances, that hepcidin can be in the normal range but inappropriately elevated relative to iron stores.

In another aspect, provided herein is a kit for treating a disorder associated with elevated hepcidin levels or a disorder of iron homeostasis, comprising an antibody, or an antigen-binding fragment thereof, as described herein, and a label attached to or packaged with the container, the label describing use of the antibody, or an antigen-binding fragment thereof, with an erythropoiesis stimulator.

In another aspect, provided herein is a kit for treating a disorder associated with elevated hepcidin levels, comprising an erythropoiesis stimulator and a label attached to or packaged with the container, the label describing use of the erythropoiesis stimulator with an antibody, or an antigen-binding fragment thereof, as described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1. Examples of hepcidin peptide antigen sequences used to immunize BALB/c mice for hybridoma production and discovery of MAbs H32, 583, and 1B1.

FIG. 2. Example of a first round screen of isolated hybridomas using neutravidin coated plates coated with K18-biotin hepcidin-25 and detected by anti-mouse IgG (H+L) conjugated HRP. Displayed are optical densities (OD) at 450 nm following HRP development and stop solution addition. Note positive signals (>2.0 OD) in Column 9 rows D-F. Positive and negative control wells are G12 and H12, respectively.

FIG. 3. Example of a second round screen of isolated hybridomas from first round screens determined to be positive (FIG. 2) using rabbit anti-mouse Fc coated plates to capture mouse IgG from hybridoma supernatants. Bound mouse IgGs are then screened for binding to K18-biotin hepcidin-25 using streptavidin conjugated HRP. Displayed are optical densities (OD) at 450 nm following HRP development and stop solution added. Note positive signals (>2.0 OD) in Column 9 row D. Positive and negative control wells are G12 and H12, respectively.

FIG. 4. Screening for functional activity of hybridomas positive for anti-hepcidin binding. Wells were coated with anti-mouse Fc antibodies and blocked. In duplicate wells, each indicated hybridoma supernatant was added to binding buffer containing 1 ng NT-biotin hepcidin-25 tracer, with or without 100 ng synthetic hepcidin-25. Binding of the NT-biotin hepcidin-25 was detected with SA-HRP as OD at 450 nm after addition of stop solution to the wells. Antibody 5A3 (as did 4B1 and 5A4) showed excellent binding in buffer without hepcidin-25 and was completed blocked by hepcidin-25 in the binding buffer indicating hybridoma 5A3 contained an antibody that bound to both NT-biotin hepcidin-25 and synthetic hepcidin-25 in solution. The clone ultimately derived from hybridoma 5A3 was later renamed MAb 583; thus, data for MAb 583 is shown in the 5A3 wells. Clones 4B1 and 5A4 although apparently positive in this screen both failed to produce functional anti-hepcidin antibodies when tested after further expansion, functionality, and isotype screening.

FIG. 5. Characteristics of MAbs 583, 1B1, and H32, including antigens, serum titers of immunized BALB/c mice, injection sites, injection frequency, tissue(s) used for hybridoma production, and success rates through each round of screening leading to these isolated, functional anti-hepcidin monoclonal antibodies.

FIG. 6. Overall success rates for functional anti-hepcidin-25 MAbs across 8 MAb development campaigns. A total of 11,845 hybridomas were screened for the discovery of MAbs H32, 583, and 1B1.

FIG. 13. Binding affinity results from Biacore experiments shown in FIG. 12. The data show higher affinity and picomolar association (KA) and lower dissociation constants (KD) for MAb 583 for K18-biotin hepcidin-25 than NT-biotin hepcidin-25 than when assessed at 24 µg/ml.

FIG. 28. Descriptive statistics (mean, standard deviation, SEM) and results from one way ANOVA of serum iron concentrations of five groups of male C57BL/6 mice from the in vivo study of MAb 583 shown in FIG. 27. Multiple Comparisons versus Control Group (Holm-Sidak method) with an overall significance level of P=0.05 gave comparison-dependent unadjusted P values ranging from 0.001 to 0.253.

DETAILED DESCRIPTION OF THE INVENTION

Figure 7:
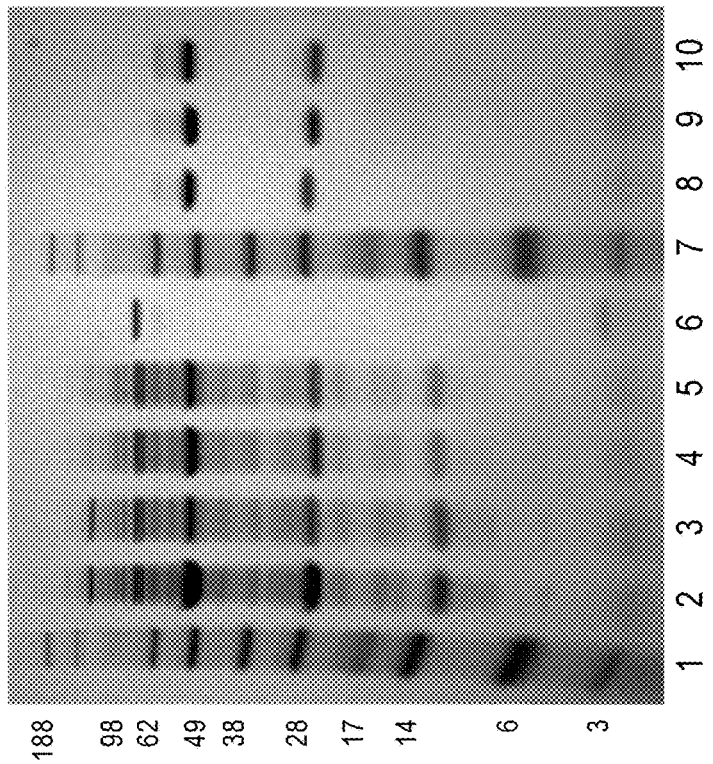
FIG. 7 Reducing SDS-PAGE analysis of purification of MAb 583 on a Protein A column. Crude preparations of diluted hybridoma supernatants, flow-through fractions collected during column washing, and highly purified MAb 583 (Purification Lot 003) and 1B1 (Purification Lot 003) analyzed by Coomassie staining. Lane descriptions are provided to the right of the blot.

In accordance with the present application, there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984), each of which is specifically incorporated herein by reference in its entirety.

Antibody Terminology

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described below. Complementarity determining region (CDR) grafted antibodies and other humanized antibodies (including CDR modifications and framework region modifications) are also contemplated by this term.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. For example, synthetic gene sequences can include amino acid, or polynucleotide, sequences that have been changed, for example, by the replacement, deletion, or addition, of one or more, amino acids, or nucleotides, thereby providing an antibody amino acid sequence, or a polynucleotide coding sequence that is different from the source sequence. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3 and FR4), largely adopting a (3-sheet configuration interspersed with three CDRs which form loops connecting and, in some cases, part of the (3-sheet structure. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669).

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3) according to Kabat et al., Sequences of Proteins of Immunological Interest, 5th Ed. Public Health Service, National Institutes of Health, Bethesda, Md. (1991)). It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2) and 91-96 (CDRL3), and in the heavy chain variable domain, the CDRs typically correspond to approximately residues 26-32 (CDRH1), 53-55 (CDRH2) and 96-101 (CDRH3) according to Chothia and Lesk, J. Mol. Biol., 196: 901-917 (1987)).

As used herein, "framework region" or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al., Sequences of Proteins of Immunological Interest, 5th Ed. Public Health Service, National Institutes of Health, Bethesda, Md. (1991)). As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, J. Mol. Biol., 196: 901-917 (1987)).

The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three dimensional structure of the antibody variable domain can be derived from a crystal structure or protein modeling.

Constant domains (Fc) of antibodies are not involved directly in binding an antibody to an antigen but, rather, exhibit various effector functions, such as participation of the antibody in antibody-dependent cellular toxicity via interactions with, for example, Fc receptors (FcR). Fc domains can also increase bioavailability of an antibody in circulation following administration to a subject.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are "one-half" antibodies comprising a single heavy chain and a single light chain. Other forms of single chain antibodies, such as diabodies are also encompassed herein.

"F(ab')$_2$" and "Fab" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of $V_L$ and $C_L$ (light chain constant region), and a heavy chain fragment composed of $V_H$ and $C_{H\gamma1}$ (γ1) region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent or covalent association (disulfide linked Fv's have been described in the art, Reiter et al. (1996) Nature Biotechnology 14:1239-1245). It is in this configuration that the three CDRs of each variable domain interact to define an antigen-binding site on the surface of the $V_H$-$V_L$ dimer. Collectively, a combination of one or more of the CDRs from each of the $V_H$ and $V_L$ chains confer antigen-binding specificity to the antibody. For example, it would be understood that, for example, the CDRH3 and CDRL3 could be sufficient to confer antigen-binding specificity to an antibody when transferred to $V_H$ and $V_L$ chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$), are coded for by separate genes, they can be joined using recombinant methods by a synthetic linker that enables them to be made as a single protein chain in which the $V_L$ and $V_H$ regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

"Single-chain Fv" or "sFv" antibody fragments comprise the $V_H$ and $V_L$ domains of an antibody, wherein these domains are present in a single polypeptide chain. In some embodiments, the Fv polypeptide further comprises a polypeptide linker between the $V_H$ and $V_L$ domains which enables the sFv to form the desired structure for antigen binding. For a review of sFvs, see, e.g., Pluckthun in The Pharmacology of Monoclonal Antibodies, Vol. 113, Rosenburg and Moore eds. Springer-Verlag, New York, pp. 269-315 (1994).

The term "AVIMER™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, Nat. Biotechnol. 23:1493-1494; Silverman et al., 2006, Nat. Biotechnol. 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and these domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "AVIMERs™" from avidity multimers.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129). This is in contrast to CDR3 regions of antibodies of many other species. For example, the CDR3 of mouse $V_H$ has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Humanized" forms of non-human (e.g., murine) antibodies include chimeric antibodies which contain minimal sequence derived from a non-human Ig. For the most part, humanized antibodies are human IgGs (recipient antibody) in which one or more of the CDRs of the recipient are replaced by CDRs from a non-human species antibody (donor antibody) such as mouse, rat, rabbit or non-human primate having the desired specificity, affinity and binding function. In some instances, one or more FR amino acid residues of the human Ig are replaced by corresponding non-human amino acid residues. Furthermore, humanized antibodies can contain residues which are not found in the recipient antibody or in the donor antibody. These modifications can be made to refine antibody performance, if needed. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally can also include at least a portion of an immunoglobulin constant region (Fc), typically that of a human immunoglobulin. For details, see Jones et al., Nature 321: 522-525 (1986); Reichmann et al., Nature 332: 323-329 (1988); and Presta, Curr. Op. Struct. Biol. 2: 593-596 (1992).

A humanized antibody also includes antibodies in which part, or all of the CDRs of the heavy and light chain are derived from a non-human monoclonal antibody, substantially all the remaining portions of the variable regions are derived from human variable region (both heavy and light chain), and the constant regions are derived from a human constant region. In one embodiment, the CDR1, CDR2 and CDR3 regions of the heavy and light chains are derived from a non-human antibody. In yet another embodiment, at least one CDR (e.g., a CDR3) of the heavy and light chains is derived from a non-human antibody. Various combinations of CDR1, CDR2, and CDR3 can be derived from a non-human antibody and are contemplated herein. In one non-limiting example, one or more of the CDR1, CDR2 and CDR3 regions of each of the heavy and light chains are derived from the sequences provided herein.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies can be made by the hybridoma method first described by Kohler et al., Nature 256:495 (1975), or can be made by recombinant DNA methods (see, e.g., U.S. Pat. No. 4,816,567). In certain embodiments, the monoclonal antibodies can be isolated from phage antibody libraries using the techniques described in Clackson et al., Nature 352:624-628 (1991) and Marks et al., J. Mol. Biol. 222:581-597 (1991), for example.

Antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column such as described in more detail below.

Exemplary antibodies for use in the compositions and methods described herein are intact immunoglobulin molecules, such as, for example, a humanized antibody or those portions of a humanized Ig molecule that contain the antigen binding site (i.e., paratope) or a single heavy chain and a single light chain, including those portions known in the art as Fab, Fab', F(ab)', F(ab')$_2$, Fd, scFv, a variable heavy domain, a variable light domain, a variable NAR domain, bi-specific scFv, a bi-specific Fab$_2$, a tri-specific Fab$_3$ and a single chain binding polypeptides and others also referred to as antigen-binding fragments. When constructing an immunoglobulin molecule or fragments thereof, variable regions or portions thereof may be fused to, connected to, or otherwise joined to one or more constant regions or portions thereof to produce any of the antibodies or fragments thereof described herein. This may be accomplished in a variety of ways known in the art, including but not limited to, molecular cloning techniques or direct synthesis of the nucleic acids encoding the molecules. Exemplary non-limiting methods of constructing these molecules can also be found in the examples described herein.

Methods for making bispecific or other emultispecific antibodies are known in the art and include chemical cross-linking, use of leucine zippers (Kostelny et al., *J. Immunol.* 148:1547-1553, 1992); diabody technology (Hollinger et al., *Proc. Natl. Acad. Sci.* USA 90:6444-48, 1993); scFv dimers [Gruber et al., *J Immunol.* 152: 5368, 1994], linear antibodies (Zapata et al., *Protein Eng.* 8:1057-62, 1995); and chelating recombinant antibodies (Neri et al., *J Mol Biol.* 246:367-73, 1995).

"Linear antibodies" comprise a pair of tandem Fd segments ($V_H$-$C_H$1-$V_H$-$C_H$1) which form a pair of antigen binding regions. Linear antibodies can be bispecific or monospecific (Zapata et al. Protein Eng. 8:1057-62 (1995)).

Additionally, the anti-hepcidin antibodies disclosed herein can also be constructed to fold into multivalent forms, which may improve binding affinity, specificity and/or increased half-life in blood. Multivalent forms of anti-hepcidin antibodies can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., *Hum Antibodies Hybridomas* 6(3): 93-101 (1995), the disclosure of which is incorporated herein by reference in its entirety).

According to another approach for making bispecific antibodies, the interface between a pair of antibody molecules can be engineered to maximize the percentage of heterodimers which are recovered from recombinant cell culture. One interface comprises at least a part of the $C_H$3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011 published Sep. 6, 1996.

Techniques for generating bispecific or multispecific antibodies from antibody fragments are conventionally known in the art. For example, bispecific or trispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., *Science* 240: 1041-1043 (1988) disclose secretion of functional antibody fragments from bacteria (see, e.g., Better et al., Skerra et al. *Science* 240: 1038-1041 (1988)). For example, Fab'-SH fragments can be directly recovered from *E. coli* and chemically coupled to form bispecific antibodies (Carter et al., *Bio/Technology* 10:163-167 (1992); Shalaby et al., *J. Exp. Med.* 175:217-225 (1992)).

Various techniques for making and isolating bispecific or multispecific antibody fragments directly from recombinant cell culture have are conventionally known in the art. For example, bispecific antibodies have been produced using leucine zippers, e.g., GCN4. (See generally Kostelny et al., *J. Immunol.* 148(5):1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

As used herein, a "minibody" refers to a scFv fused to $CH_3$ via a peptide linker (hingeless) or via an IgG hinge has been described in Olafsen, et al., *Protein Eng Des Sel.* April 2004; 17(4):315-23.

As used herein, a "maxibody" refers to a bivalent scFv covalently attached to the Fc region of an immunoglobulin, see, for example, Fredericks et al., Protein Engineering, Design & Selection, 17:95-106 (2004) and Powers et al., *Journal of Immunological Methods,* 251:123-135 (2001).

As used herein, an "intrabody" refers to a single chain antibody which demonstrates intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al., (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

Additionally contemplated herein are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO 03/041600, U.S. Patent publication 20030133939 and US Patent Publication 20030118592, which are hereby incorporated by reference.

Humanization of antibodies and antigen-binding fragments thereof, can be accomplished via a variety of methods known in the art and described herein. Similarly, production of humanized antibodies can also be accomplished via methods known in the art and described herein.

In one exemplary embodiment, the application contemplates a single chain binding polypeptide having a heavy chain variable region, and/or a light chain variable region which binds an epitope described herein and has, optionally, an immunoglobulin Fc region. Such a molecule is a single chain variable fragment (scFv) optionally having effector function or increased half-life through the presence of the immunoglobulin Fc region. Methods of preparing single chain binding polypeptides are known in the art (e.g., U.S. Patent Application No. 2005/0238646).

The terms "germline gene segments" or "germline sequences" refer to the genes from the germline (the haploid gametes and those diploid cells from which they are formed). The germline DNA contains multiple gene segments that encode a single Ig heavy or light chain. These gene segments are carried in the germ cells but cannot be transcribed and translated into heavy and light chains until they are arranged into functional genes. During B-cell differentiation in the bone marrow, these gene segments are randomly shuffled by a dynamic genetic system capable of generating more than $10^8$ specificities. Most of these gene segments are published and collected by the germline database.

Binding affinity and/or avidity of antibodies or antigen-binding fragments thereof may be improved by modifying framework regions. Methods for modifications of framework regions are known in the art and are contemplated herein. Selection of one or more relevant framework amino acid positions to altered depends on a variety of criteria. One criterion for selecting relevant framework amino acids to change can be the relative differences in amino acid framework residues between the donor and acceptor molecules. Selection of relevant framework positions to alter using this approach has the advantage of avoiding any subjective bias in residue determination or any bias in CDR binding affinity contribution by the residue.

As used herein, "immunoreactive" refers to antibodies or antigen-binding fragments thereof that are specific to a sequence of amino acid residues ("binding site" or "epitope"), yet if are cross-reactive to other peptides/proteins, are not toxic at the levels at which they are formulated for administration to human use. The term "binding" refers to a direct association between two molecules, due to, for example, covalent, electrostatic, hydrophobic, and ionic and/or hydrogen-bond interactions under physiological conditions, and including interactions such as salt bridges and water bridges and any other conventional binding means. The term "preferentially binds" means that the binding agent binds to the binding site with greater affinity than it binds unrelated amino acid sequences. Preferably such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the binding agent for unrelated amino acid sequences. The terms "immunoreactive" and "preferentially binds" are used interchangeably herein.

As used herein, the term "affinity" refers to the equilibrium constant for the reversible binding of two agents and is expressed as Kd. In one embodiment, the antibodies, or antigen-binding fragments thereof exhibit desirable characteristics such as binding affinity as measured by $K_D$ (equilibrium dissociation constant) for hepcidin in the range of $1 \times 10^{-6}$ M or less, or ranging down to $10^{-16}$ M or lower, (e.g., about $10^{-7}$, $10^{-8}$, $10^{-9}$, $10^{-10}$, $10^{-11}$, $10^{-12}$, $10^{-13}$, $10^{-14}$, $10^{-15}$, $10^{-16}$ M or less). The equilibrium dissociation constant can be determined in solution equilibrium assay using BIAcore and/or KinExA. As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen binding can involve, for example, a CDR3 or a CDR3 pair or, in some cases, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody can recognize one or more amino acid sequences; therefore an epitope can define more than one distinct amino acid sequence. Epitopes recognized by antibodies can be determined by peptide mapping and sequence analysis techniques well known to one of skill in the art. Binding interactions are manifested as intermolecular contacts with one or more amino acid residues of a CDR.

The term "specific" refers to a situation in which an antibody will not show any significant binding to molecules other than the antigen containing the epitope recognized by the antibody. The term is also applicable where for example, an antigen binding domain is specific for a particular epitope which is carried by a number of antigens, in which case the antibody or antigen-binding fragment thereof carrying the antigen binding domain will be able to bind to the various antigens carrying the epitope. The terms "preferentially binds" or "specifically binds" mean that the antibodies or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody or fragment thereof for unrelated amino acid sequences. The terms "immunoreactive," "binds," "preferentially binds" and "specifically binds" are used interchangeably herein. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

Antibodies may be screened for binding affinity by methods known in the art including, but not limited to, gel-shift assays, Western blots, radiolabeled competition assay, co-fractionation by chromatography, co-precipitation, cross linking, ELISA, and the like, which are described in, for example, Current Protocols in Molecular Biology (1999) John Wiley & Sons, NY, which is incorporated herein by reference in its entirety.

Antibodies which bind to the desired epitope on the target antigen may be screened in a routine cross-blocking assay such as described in Antibodies, A Laboratory Manual, Cold Spring Harbor Laboratory, Ed Harlow and David Lane (1988), can be performed. Routine competitive binding assays may also be used, in which an unknown antibody is characterized by its ability to inhibit binding of target to a target-specific antibody of the invention. Intact antigen, fragments thereof such as the extracellular domain, or linear epitopes can be used. Epitope mapping is described in Champe et al., J. Biol. Chem. 270: 1388-1394 (1995). Antibodies that inhibit or neutralize human hepcidin activity may be identified by contacting hepcidin with an antibody, comparing hepcidin activity in the presence and absence of the test antibody, and determining whether the presence of the antibody decreases activity of the hepcidin. The biological activity of a particular antibody, or combination of antibodies, may be evaluated in vivo using a suitable animal model, including any of those described herein.

In one embodiment, provided herein are high throughput screening (HTS) assays to identify antibodies that interact with or inhibit biological activity of target hepcidin. HTS assays permit screening of large numbers of compounds in an efficient manner.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:

(i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic non-polar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art as described above.

A "conserved residue" is an amino acid that is relatively invariant across a range of similar proteins. Often conserved residues will vary only by being replaced with a similar amino acid, as described above for "conservative amino acid substitution."

The letter "x" or "xaa" as used in amino acid sequences herein is intended to indicate that any of the twenty standard amino acids may be placed at this position unless specifically noted otherwise.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid (nucleotide, oligonucleotide) and amino acid (protein) sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST amino acid searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (see, www.ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

"Isolated" (used interchangeably with "substantially pure" or "purified") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"Inducing a host immune response" means that a subject experiences alleviation or reduction of signs or symptoms of illness, and specifically includes, without limitation, prolongation of survival.

Humanized immunoglobulins, including humanized antibodies, have been constructed by means of genetic engineering. Most humanized immunoglobulins that have been previously described have comprised a framework that is identical to the framework of a particular human immunoglobulin chain (i.e., an acceptor or recipient), and three CDRs from a non-human (i.e., donor) immunoglobulin chain. As described herein, humanization can also include criteria by which a limited number of amino acids in the framework of a humanized immunoglobulin chain are identified and chosen to be the same as the amino acids at those positions in the donor rather than in the acceptor, in order to increase the affinity of an antibody comprising the humanized immunoglobulin chain.

When increased affinity of a humanized antibody is desired, residues within the CDRs of a converted antibody may be additionally substituted with other amino acids. Typically, no more than four amino acid residues in a CDR are changed, and most typically no more than two residues in the CDR will be changed, except for heavy chain CDR2, where as many as 10 residues may be changed. Changes in affinity can be measured by conventional methods such as those described herein (e.g., Biacore).

Methods of "superhumanizing" antibodies are described in more detail in U.S. Pat. No. 6,881,557 which is hereby incorporated by reference in its entirety.

Humanized antibodies and antigen-binding fragments can be constructed and produced using conventional techniques known in the art. In addition, recombinantly prepared antibodies can often be produced in large quantities, particularly when utilizing high level expression vectors.

Antibodies can be sequenced using conventional techniques known in the art. In one aspect, the amino acid sequences of one or more of the CDRs is inserted into a synthetic sequence of, for example, a human antibody (or antigen-binding fragment thereof) framework to create a human antibody that could limit adverse side reactions of treating a human subject with a non-human antibody. The amino acid sequences of one or more of the CDRs can also be inserted into a synthetic sequence of, for example, into a binding protein such as an AVIMER™ to create a construct for administration to an human subject. Such techniques can be modified depending on the species of animal to be treated. For example, for veterinary uses, an antibody, antigen-binding fragment or binding protein can be synthesized for administration of a non-human (e.g., a primate, a cow, a horse, etc.).

In another aspect, using art-recognized techniques such as those provided and incorporated herein, nucleotides encoding amino acid sequences of one or more of the CDRs can inserted, for example, by recombinant techniques in restriction endonuclease sites of an existing polynucleotide that encodes an antibody, antigen-binding fragment or binding protein.

For expression, an expression system is one which utilizes the GS system (Lonza) using a glutamine synthetase gene as the selectable marker. Briefly, a transfection is performed in CHO cells by electroporation (250V) using the GS system (Lonza) using the glutamine synthetase gene as the selectable marker. Wild type CHO cells are grown in DMEM (Sigma) containing 10% dialyzed Fetal Calf Serum (FCS) with 2 mM glutamine. $6 \times 10^7$ CHO cells are transfected with 300 µg of linearized DNA by electroporation. After electroporation the cells are resuspended in DMEM with glutamine and plated out into 36×96-well plates (50 µl/well), and incubated at 37° C. in 5% $CO_2$. The following day, 150 µl/well of selective medium (DMEM without glutamine) is added. After approximately 3 weeks the colonies are screened by ELISA (see below) using an irrelevant antibody as a negative control. All colonies producing >20 µg/ml are expanded into 24-well plates and then into duplicate T25 flasks.

For high level production, the most widely used mammalian expression system is one which utilizes the gene amplification procedure offered by dehydrofolate reductase deficient ("dhfr-") Chinese hamster ovary cells. The system is well known to the skilled artisan. The system is based upon the dehydrofolate reductase "dhfr" gene, which encodes the DHFR enzyme, which catalyzes conversion of dehydrofolate to tetrahydrofolate. In order to achieve high production, dhfr-CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level and the stability of the cells being employed are taken into account. In long term culture, recombinant CHO cell populations lose homogeneity with respect to their specific antibody productivity during amplification, even though they derive from a single, parental clone.

The present application provides an isolated polynucleotide (nucleic acid) encoding an antibody or antigen-binding fragment as described herein, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody or antigen-binding fragments thereof described herein as provided itself forms an aspect of the present application, as does a method of production of the antibody or antigen-binding fragments thereof described herein which method comprises expression from encoding nucleic acid therefrom. Expression can conveniently be achieved by culturing under appropriate conditions recombinant host cells containing the nucleic acid. Following production by expression, an antibody or antigen-binding fragment can be isolated and/or purified using any suitable technique, then used as appropriate.

Specific antibodies, antigen-binding fragments, and encoding nucleic acid molecules and vectors described herein can be provided isolated and/or purified, e.g., from their natural environment, in substantially pure or homogeneous form. In the case of nucleic acid, free or substantially free of nucleic acid or genes origin other than the sequence encoding a polypeptide with the required function. Nucleic acid can comprise DNA or RNA and can be wholly or partially synthetic. Methods of purification are well known in the art.

Systems for cloning and expression of a polypeptide in a variety of different host cells are well known. Suitable host cells include, but are not limited to, bacteria cells, mammalian cells, yeast cells and baculovirus systems. Mammalian cell lines available in the art for expression of a heterologous polypeptide include Chinese hamster ovary cells, HeLa cells, baby hamster kidney cells, NS0 mouse myeloma cells and many others. A common bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of the antibodies and antigen-binding fragments described herein, see for recent reviews, for example Raff, M. E. (1993) Curr. Opinion Biotech. 4: 573-576; Trill J. J. et al. (1995) Curr. Opinion Biotech 6: 553-560, each of which is which is incorporated herein by reference in its entirety.

Suitable vectors can be chosen or constructed, containing appropriate regulatory sequences, including promoter sequences, terminator sequences, polyadenylation sequences, enhancer sequences, marker genes and other sequences as appropriate. Vectors can be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The methods disclosures of Sambrook et al. and Ausubel et al. are incorporated herein by reference in their entirety and are well known in the art.

Thus, a further aspect provides a host cell containing nucleic acid as disclosed herein. A still further aspect provides a method comprising introducing such nucleic acid into a host cell. The introduction can employ any available technique. For eukaryotic cells, suitable techniques can include, for example, calcium phosphate transfection, DEAE Dextran, electroporation, liposome-mediated transfection and transduction using retrovirus or other virus, e.g., vaccinia or, for insect cells, baculovirus. For bacterial cells, suitable techniques can include, for example, calcium chloride transformation, electroporation and transfection using bacteriophage.

The introduction can be followed by causing or allowing expression from the nucleic acid, e.g. by culturing host cells under conditions for expression of the gene.

In one embodiment, the nucleic acid is integrated into the genome (e.g. chromosome) of the host cell. Integration can be promoted by inclusion of sequences which promote recombination with the genome, in accordance with standard techniques. Ig enhances can be initialized as needed to maximize expression.

The present application also provides a method which comprises using a construct as stated above in an expression system in order to express the antibodies or antigen-binding fragments thereof as above.

The present application also relates to isolated nucleic acids, such as recombinant DNA molecules or cloned genes, or degenerate variants thereof, mutants, analogs, or fragments thereof, which encode an antibody or antigen-binding sequence described herein.

In one aspect, the present application provides a nucleic acid which codes for an antibody or antigen-binding fragment thereof as described herein.

In a further embodiment, the full DNA sequence of the recombinant DNA molecule or cloned gene of an antibody or antigen-binding fragment described herein can be operatively linked to an expression control sequence which can be introduced into an appropriate host. The application accordingly extends to unicellular hosts transformed with the cloned gene or recombinant DNA molecule comprising a DNA sequence encoding the $V_H$ and/or $V_L$, or portions thereof, of the antibody.

Another feature is the expression of the DNA sequences disclosed herein. As is well known in the art, DNA sequences can be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

Polynucleotides and vectors can be provided in an isolated and/or a purified form (e.g., free or substantially free of polynucleotides of origin other than the polynucleotide encoding a polypeptide with the required function). As used herein, "substantially pure," and "substantially free" refer to a solution or suspension containing less than, for example, about 20% or less extraneous material, about 10% or less extraneous material, about 5% or less extraneous material, about 4% or less extraneous material, about 3% or less extraneous material, about 2% or less extraneous material, or about 1% or less extraneous material.

A wide variety of host/expression vector combinations can be employed in expressing the DNA sequences of this invention. Useful expression vectors, for example, can consist of segments of chromosomal, non-chromosomal and synthetic DNA sequences. Suitable vectors include, but are not limited to, derivatives of SV40 and known bacterial plasmids, e.g., *E. coli* plasmids col E1, Pcr1, Pbr322, Pmb9 and their derivatives, plasmids such as RP4; phage DNAs, e.g., the numerous derivatives of phage k, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Also provided herein is a recombinant host cell which comprises one or more polynucleotide constructs. A polynucleotide encoding an antibody or antigen-binding fragment as provided herein forms an aspect of the present application, as does a method of production of the antibody or antigen-binding fragment which method comprises expression from the polynucleotide. Expression can be achieved, for example, by culturing under appropriate conditions recombinant host cells containing the polynucleotide. An antibody or antigen-binding fragment can then be isolated and/or purified using any suitable technique, and used as appropriate.

Any of a wide variety of expression control sequences—sequences that control the expression of a DNA sequence operatively linked to it—can be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast alpha-mating factors, and other sequences known to control the expression of genes of prokaryotic or eukaryotic cells or their viruses, and various combinations thereof.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary (CHO) cells, HeLa cells, baby hamster kidney cells, NS0 mouse myeloma cells and many others. A common, bacterial host can be, for example, E. coli.

The expression of antibodies or antigen-binding fragments in prokaryotic cells, such as E. coli, is well established in the art. For a review, see for example Plückthun, A. Bio/Technology 9: 545-551 (1991). Expression in eukaryotic cells in culture is also available to those skilled in the art (Raff, M. E. (1993) Curr. Opinion Biotech. 4: 573-576; Trill J. J. et al. (1995) Curr. Opinion Biotech 6: 553-560).

A wide variety of unicellular host cells are also useful in expressing the DNA sequences. These hosts include well-known eukaryotic and prokaryotic hosts, such as strains of E. coli, Pseudomonas, Bacillus, Streptomyces, fungi such as yeasts, and animal cells, such as CHO, YB/20, NS0, SP2/0, R1.1, B-W and L-M cells, African Green Monkey kidney cells (e.g., COS 1, COS 7, BSC1 BSC40, and BMT10), insect cells (e.g., Sf9), and human cells and plant cells in tissue culture.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present application also provides constructs in the form of plasmids, vectors, transcription or expression cassettes as described elsewhere herein which comprise at least one polynucleotide as above. Suitable vectors can be chosen or constructed, containing appropriate regulatory sequences, including promoter sequences, terminator sequences, polyadenylation sequences, enhancer sequences, selectable markers and other sequences as appropriate. Vectors can be plasmids, viral e.g., phage, phagemid, etc., as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The methods and disclosures of Sambrook et al. and Ausubel et al. are incorporated herein by reference.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

A further aspect provides a host cell containing one or more polynucleotides as disclosed herein. Yet a further aspect provides a method of introducing such one or more polynucleotides into a host cell, any available technique. For eukaryotic cells, suitable techniques can include, for example, calcium phosphate transfection, DEAEDextran, electroporation, liposome-mediated transfection and transduction using retrovirus or other virus (e.g. vaccinia) or, for insect cells, baculovirus. For bacterial cells, suitable techniques can include, for example calcium chloride transformation, electroporation and transfection using bacteriophages.

The introduction can be followed by causing or allowing expression from the one or more polynucleotides, e.g. by culturing host cells under conditions for expression of one or more polypeptides from one or more polynucleotides. Inducible systems can be used and expression induced by addition of an activator.

In one embodiment, the polynucleotides can be integrated into the genome (e.g., chromosome) of the host cell. Integration can be promoted by inclusion of sequences which promote recombination with the genome, in accordance with standard techniques. In another embodiment, the nucleic acid is maintained on an episomal vector in the host cell.

Methods are provided herein which include using a construct as stated above in an expression system in order to express a specific polypeptide.

Considering these and other factors, a person skilled in the art will be able to construct a variety of vector/expression control sequence/host combinations that will express the DNA sequences on fermentation or in large scale animal culture.

A polynucleotide encoding an antibody, antigen-binding fragment, or a binding protein can be prepared recombinantly/synthetically in addition to, or rather than, cloned. The polynucleotide can be designed with the appropriate codons for the antibody, antigen-binding fragment, or a binding protein. In general, one will select preferred codons for an intended host if the sequence will be used for expression. The complete polynucleotide can be assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259: 6311 (1984), each of which is which is incorporated herein by reference in its entirety.

A general method for site-specific incorporation of unnatural amino acids into proteins is described in Noren et al., Science, 244:182-188 (April 1989). This method can be used to create analogs with unnatural amino acids.

As mentioned above, a DNA sequence encoding an antibody or antigen-binding fragment thereof can be prepared synthetically rather than cloned. The DNA sequence can be designed with the appropriate codons for the antibody or antigen-binding fragment amino acid sequence. In general, one will select preferred codons for the intended host if the sequence will be used for expression. The complete sequence is assembled from overlapping oligonucleotides prepared by standard methods and assembled into a complete coding sequence.

Antibodies, or antigen-binding fragments thereof, can be modified using techniques known in the art for various purposes such as, for example, by addition of polyethylene glycol (PEG). PEG modification (PEGylation) can lead to one or more of improved circulation time, improved solubility, improved resistance to proteolysis, reduced antigenicity and immunogenicity, improved bioavailability, reduced toxicity, improved stability, and easier formulation (for a review see, Francis et al., International Journal of Hematology 68:1-18, 1998).

In the case of an antigen-binding fragment which does not contain an Fc portion, an Fc portion can be added to (e.g., recombinantly) the fragment, for example, to increase half-life of the antigen-binding fragment in circulation in blood when administered to a subject. Choice of an appropriate Fc region and methods of to incorporate such fragments are known in the art. Incorporating a Fc region of an IgG into a polypeptide of interest so as to increase its circulatory half-life, but so as not to lose its biological activity can be accomplished using conventional techniques known in the art such as, for example, described in U.S. Pat. No. 6,096, 871, which is hereby incorporated by reference in its entirety. Fc portions of antibodies can be further modified to increase half-life of the antigen-binding fragment in circulation in blood when administered to a subject. Modifications can be determined using conventional means in the art such as, for example, described in U.S. Pat. No. 7,217,798, which is hereby incorporated by reference in its entirety.

Other methods of improving the half-life of antibody-based fusion proteins in circulation are also known such as, for example, described in U.S. Pat. Nos. 7,091,321 and 6,737,056, each of which is hereby incorporated by reference. Additionally, antibodies and antigen-binding fragments thereof may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). Similarly, antibodies or antigen-binding fragments thereof that can bind an epitope can be attached at their C-terminal end to all or part of an immunoglobulin heavy chain derived from any antibody isotype, e.g., IgG, IgA, IgE, IgD and IgM and any of the isotype sub-classes, particularly IgG1, IgG2b, IgG2a, IgG3 and IgG4.

Additionally, the antibodies or antigen-binding fragments described herein can also be modified so that they are able to cross the blood-brain barrier. Such modification of the antibodies or antigen-binding fragments described herein allows for the treatment of brain diseases such as glioblastoma multiforme (GBM). Exemplary modifications to allow proteins such as antibodies or antigen-binding fragments to cross the blood-brain barrier are described in US Patent Application Publication 2007/0082380 which is hereby incorporated by reference in its entirety.

Glycosylation of immunoglobulins has been shown to have significant effects on their effector functions, structural stability, and rate of secretion from antibody-producing cells (Leatherbarrow et al., Mol. Immunol. 22:407 (1985)). The carbohydrate groups responsible for these properties are generally attached to the constant (C) regions of the antibodies. For example, glycosylation of IgG at asparagine 297 in the $C_H 2$ domain is required for full capacity of IgG to activate the classical pathway of complement-dependent cytolysis (Tao and Morrison, J. Immunol. 143:2595 (1989)). Glycosylation of IgM at asparagine 402 in the $C_H 3$ domain is necessary for proper assembly and cytolytic activity of the antibody (Muraoka and Shulman, J. Immunol. 142:695 (1989)). Removal of glycosylation sites as positions 162 and 419 in the $C_H 1$ and $C_H 3$ domains of an IgA antibody led to intracellular degradation and at least 90% inhibition of secretion (Taylor and Wall, Mol. Cell. Biol. 8:4197 (1988)). Additionally, antibodies and antigen-binding fragments thereof may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). These "defucosylated" antibodies and antigen-binding fragments may be produced through a variety of systems utilizing molecular cloning techniques known in the art, including but not limited to, transgenic animals, transgenic plants, or cell-lines that have been genetically engineered so that they no longer contain the enzymes and biochemical pathways necessary for the inclusion of a fucose in the complex N-glycoside-linked sugar chains (also known as fucosyltransferase knock-out animals, plants, or cells). Non-limiting examples of cells that can be engineered to be fucosyltransferase knock-out cells include CHO cells, SP2/0 cells, NS0 cells, and YB2/0 cells.

Glycosylation of immunoglobulins in the variable (V) region has also been observed. Sox and Hood reported that about 20% of human antibodies are glycosylated in the V region (Proc. Natl. Acad. Sci. USA 66:975 (1970)). Glycosylation of the V domain is believed to arise from fortuitous occurrences of the N-linked glycosylation signal Asn-Xaa- Ser/Thr in the V region sequence and has not been recognized in the art as playing a role in immunoglobulin function.

Glycosylation at a variable domain framework residue can alter the binding interaction of the antibody with antigen. The present invention includes criteria by which a limited number of amino acids in the framework or CDRs of a humanized immunoglobulin chain are chosen to be mutated (e.g., by substitution, deletion, or addition of residues) in order to increase the affinity of an antibody.

Cysteine residue(s) may be removed or introduced in the Fc region of an antibody or Fc-containing polypeptide, thereby eliminating or increasing interchain disulfide bond formation in this region. A homodimeric specific binding agent or antibody generated using such methods may exhibit improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992).

It has been shown that sequences within the CDR can cause an antibody to bind to MHC Class II and trigger an unwanted helper T-cell response. A conservative substitution may allow the antibody to retain binding activity, yet reduce its ability to trigger an unwanted T-cell response. In one embodiment, one or more of the N-terminal 20 amino acids of the heavy or light chain may be removed.

In some embodiments, antibody molecules may be produced with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the $CH_2$ domain. Non-fucosylated antibodies bind this receptor with increased affinity and trigger FcγRIII-mediated effector functions more efficiently than native, fucosylated antibodies. Some host cell strains, e.g. Lec13 or rat hybridoma YB2/0 cell line naturally produce antibodies with lower fucosylation levels. Shields et al., J Biol Chem. Jul. 26, 2002; 277(30):26733-40; Shinkawa et al., J Biol Chem. Jan. 31, 2003; 278(5):3466-73. An increase in the level of bisected carbohydrate, e.g. through recombinantly producing antibody in cells that overexpress GnTIII enzyme, has also been determined to increase ADCC activity. Umana et al., Nat Biotechnol. February 1999; 17(2):176-80. It has been predicted that the absence of only one of the two fucose residues may be sufficient to increase ADCC activity. (Ferrara et al., J Biol Chem. Dec. 5, 2005).

Covalent modifications of an antibody are also included herein. They may be made by chemical synthesis or by enzymatic or chemical cleavage of the antibody, if applicable. Other types of covalent modifications may be introduced by reacting targeted amino acid residues with an organic derivatizing agent that is capable of reacting with selected side chains or the N- or C-terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with diethylpyrocarbonate at pH 5.5-7.0 because this agent is relatively specific for the histidyl side chain. Para-bromophenacyl bromide also is useful; the reaction may be performed in 0.1 M sodium cacodylate at pH 6.0.

Lysinyl and amino-terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, 0-methylisourea, 2,4-pentanedione, and transaminase-catalyzed reaction with glyoxylate.

Arginyl residues may be modified by reaction with one or several conventional reagents, such as phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane may be used to form O-acetyl tyrosyl species and 3-nitro derivatives, respectively. Tyrosyl residues are iodinated using $^{125}I$ or 131I to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues may be deamidated to the corresponding glutamyl and aspartyl residues, respectively. These residues are deamidated under neutral or basic conditions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W. H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the specific binding agent or antibody. These procedures are advantageous in that they do not require production of the polypeptide or antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC Crit. Rev. Biochem., pp. 259-306 (1981).

Removal of any carbohydrate moieties present on the polypeptide or antibody may be accomplished chemically or enzymatically. Chemical deglycosylation involves exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on an antibody can be achieved by the use of a variety of endo- and exo-glycosidases as described by Thotakura et al. *Meth. Enzymol.* 138: 350 (1987).

Another type of covalent modification of hepcidin activity comprises linking an antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Affinity for binding a pre-determined polypeptide antigen can, generally, be modulated by introducing one or more mutations into the V region framework, typically in areas adjacent to one or more CDRs and/or in one or more framework regions. Typically, such mutations involve the introduction of conservative amino acid substitutions that either destroy or create the glycosylation site sequences but do not substantially affect the hydropathic structural properties of the polypeptide. Typically, mutations that introduce a proline residue are avoided. Glycosylation of antibodies and antigen-binding fragments thereof is further described in U.S. Pat. No. 6,350,861, which is incorporated by reference herein with respect to glycosylation.

Anti-Hepcidin Antibodies

Provided herein are humanized antibodies, and antigen-binding fragments thereof that bind hepcidin.

Hepcidin is involved in regulating iron homeostasis. Hepcidin binds to ferroportin and decreases its functional activity by causing it to be internalized from the cell surface and degraded.

High levels of human hepcidin may result in reduced iron levels, and vice versa. Mutations in the hepcidin gene which result in lack of hepcidin activity are associated with juvenile hemochromatosis, a severe iron overload disease. Studies in mice have demonstrated a role of hepcidin in control of normal iron homeostasis.

Hepcidin may also be involved in iron sequestration during inflammation. Hepcidin gene expression has been observed to be robustly up-regulated after inflammatory stimuli, such as infections, which induce the acute phase response of the innate immune systems of vertebrates. Hepcidin gene expression may be up-regulated by lipopolysaccharide (LPS), turpentine, Freund's complete adjuvant, incomplete adjuvant, adenoviral infections and the inflammatory cytokine interleukin-6 (IL-6). A strong correlation between hepcidin expression and anemia of inflammation was also found in patients with chronic inflammatory diseases, including bacterial, fungal, and viral infections.

Human hepcidin is a 25 amino acid peptide with antimicrobial and iron-regulating activity. It has also been referred to as LEAP-1 (liver-expressed antimicrobial peptide). A hepcidin cDNA encoding an 83 amino acid pre-propeptide in mice and an 84 amino acid pre-propeptide in rat and human were subsequently identified in a search for liver specific genes that were regulated by iron. The 24 residue N-terminal signal peptide is first cleaved to produce pro-hepcidin, which is then further processed to produce mature hepcidin, found in both blood and urine. In human urine, the predominant form contains 25 amino acids, although shorter 22 and 20 amino acid peptides are also present at undetectable or very low concentrations in certain diseases.

Monoclonal antibodies (MAbs) have been raised against hepcidin which modulate hepcidin activity and thereby regulate iron homeostasis. Hereinafter, a reference to the terms "antibody" and "antibodies" are to be considered inclusive of any of the antigen-binding fragments described herein and the terms are to be interchangeable where applicable.

These antibodies, and antigen-binding fragments thereof, are useful for the diagnosis and treatment of various conditions and diseases as well as for purification and detection of hepcidin.

Binding of an antibody or antigen-binding fragment to hepcidin can partially (e.g., 5%, 10%, 20%, 30%, 40%, 50%, 60%, 70%, 80%, 90%, 95%, 98%, 99% or any number therein) or completely modulate hepcidin. The activity of an antibody or antigen-binding fragment can be determined using an in vitro assay and/or in vivo using art-recognized assays such as those described herein or otherwise known in the art.

In one aspect, the antigen-binding fragment of any one of the antibodies described above is a Fab, a Fab', a Fd, a F(ab')$_2$, a Fv, a scFv, a single chain binding polypeptide (e.g., a scFv with Fc portion) or any other functional fragment thereof as described herein.

Antibodies, or antigen-binding fragments thereof, described herein can be further modified to alter the specific properties of the antibody while retaining the desired functionality, if needed. For example, in one embodiment, the compound can be modified to alter a pharmacokinetic property of the compound, such as in vivo stability, solubility, bioavailability or half-life.

Antibodies, or antigen-binding fragments thereof, can be formulated for any suitable route of administration to a subject including, but not limited to injection. Injection includes, for example, subcutaneous, peritoneal, or intravenous injection. Administration may be in one, two, three, four, five, six, seven, or more injection sites. In one embodiment, administration is via six injection sites.

Antibodies, antigen-binding fragments, and binding proteins which bind hepcidin generated using such methods can be tested for one or more of their binding affinity, avidity, and modulating capabilities. Useful antibodies, and antigen-binding fragments, can be administered to a subject to prevent, inhibit, manage or treat a condition disease or disorder as described in more detail below.

Conventional methods may be utilized to identify antibodies or antigen-binding fragments thereof that bind to hepcidin. Antibodies and antigen-binding fragments can be evaluated for one or more of binding affinity, association rates, disassociation rates and avidity. In one aspect, antibodies can be evaluated for their ability to modulate the activity of hepcidin or a polypeptide in which the hepcidin binding sequence (epitope) is present. Measurement binding affinity, association rates, disassociation rates and avidity can be accomplished using art-recognized assays including (Surface Plasmon Resonance), but not limited to, an enzyme-linked-immunosorbent assay (ELISA), Scatchard Analysis, BIACORE analysis, etc., as well as other assays commonly used and known to those of ordinary skill in the art.

Measurement of binding of antibodies to hepcidin and/or the ability of the antibodies and antigen-binding fragments thereof, may be determined using, for example, an enzyme-linked-immunosorbent assay (ELISA), a competitive binding assay, an ELISPOT assay, or any other useful assay known in the art. These assays are commonly used and well-known to those of ordinary skill in the art.

In one non-limiting embodiment, an ELISA assay can be used to measure the binding capability of specific antibodies or antigen-binding fragments that bind to hepcidin.

Assays, such as an ELISA, also can be used to identify antibodies or antigen-binding fragments thereof which exhibit increased specificity for hepcidin in comparison to other antibodies or antigen-binding fragments thereof. Assays, such as an ELISA, also can be used to identify antibodies or antigen-binding fragments thereof with bind to epitopes across one or more polypeptides and across one or more species of hepcidin. The specificity assay can be conducted by running parallel ELISAs in which a test antibodies or antigen-binding fragments thereof is screened concurrently in separate assay chambers for the ability to bind one or more epitopes on different species of the polypeptide containing the hepcidin epitopes to identify antibodies or antigen-binding fragments thereof that bind to hepcidin. Another technique for measuring apparent binding affinity familiar to those of skill in the art is a surface plasmon resonance technique (analyzed on a BIACORE 2000 system) (Liljeblad, et al., *Glyco. J.* 2000, 17:323-329). Standard measurements and traditional binding assays are described by Heeley, R. P., *Endocr. Res.* 2002, 28:217-229.

Antibodies and antigen binding fragments thereof can be tested for a variety of functions using a variety of in vitro and in vivo methods including, but not limited to those known in the art and those described herein.

Provided herein are antibodies and antigen-binding fragments thereof that bind to hepcidin. In one aspect, provided herein is an antibody, or antigen-binding fragment thereof, that specifically binds to hepcidin, comprising a heavy chain variable region and a light chain variable region, wherein said heavy chain variable region comprises:
(i) a CDR1 having an amino acid sequence of any one of SEQ ID NOS: 55-57,
(ii) a CDR2 having an amino acid sequence of any one of SEQ ID NOS: 58-60, and
(iii) a CDR3 having an amino acid sequence of any one of SEQ ID NOS: 61-63; and said light chain variable region comprises:
(i) a CDR1 having an amino acid sequence of any one of SEQ ID NOS: 64-66,
(ii) a CDR2 having an amino acid sequence of any one of SEQ ID NOS: 67-69, and
(iii) a CDR3 having an amino acid sequence of any one of SEQ ID NOS: 70-72.

In one aspect, provided herein is an antibody, or antigen-binding fragment thereof, that specifically binds to hepcidin or a hepcidin peptide, comprising a heavy chain variable region and a light chain variable region, wherein said heavy chain variable region comprises:
(i) a CDR1 having an amino acid sequence encoded by any one of SEQ ID NOS: 1-3,
(ii) a CDR2 having an amino acid sequence encoded by any one of SEQ ID NOS: 4-6, and
(iii) a CDR3 having an amino acid sequence encoded by any one of SEQ ID NOS: 7-9;
and said light chain variable region comprises:
(i) a CDR1 having an amino acid sequence encoded by any one of SEQ ID NOS: 10-12,
(ii) a CDR2 having an amino acid sequence encoded by any one of SEQ ID NOS: 13-15, and
(iii) a CDR3 having an amino acid sequence encoded by any one of SEQ ID NOS: 16-18. In one aspect, provided herein is an antibody, or antigen-binding fragment thereof, comprises a heavy chain variable region framework region; and a light chain variable region framework region as set forth in the Sequence Listing below where the CDRs identified in any one of SEQ ID NOS: 1-18 or 55-72 are inserted into the framework region utilizing Kabat numbering.

In one aspect, provided herein is an antibody, or antigen-binding fragment thereof, that specifically binds to hepcidin, prepared by injecting a rodent (i.e., mouse, rat or rabbit) with a peptide having an amino acid sequence of any one of SEQ ID NOS: 19-27. In another embodiment, the peptide is conjugated to a carrier (e.g., keyhole limpet hemocyanin (KLH)) or an adjuvant (complete Freund's adjuvant (CFA) or incomplete Freund's adjuvant (IFA)). In one embodiment, the antibody, or antigen-binding fragment thereof, that specifically binds to amino acid residues 1-9 of hepcidin. In another embodiment, provided herein is an antibody, or antigen-binding fragment thereof, that specifically binds to amino acid residues 1-7 of hepcidin.

A hepcidin peptide to which an antibody, or antigen-binding fragment thereof, binds may have an amino acid sequence of SEQ ID NO: 19.

Provided herein is an antibody, or antigen-binding fragment thereof, that specifically binds to an epitope comprising amino acid sequence of any one of Hep-5, Hep-9, Hep-20, Hep 22 and Hep-25 where the sequences of the peptides are provided in the sequence listing.

In one embodiment, the antibody, or antigen-binding fragment thereof, specifically binds to an epitope comprising an amino acid sequence of Hep-20 (SEQ ID NO: 22), Hep-22 (SEQ ID NO: 23) and Hep-25 (SEQ ID NO: 19).

In one embodiment, the antibody, or antigen-binding fragment thereof, specifically binds to an epitope comprising Hep-5 (SEQ ID NO: 25) or Hep-9 (SEQ ID NO: 24). In another embodiment, provided herein is an antibody, or antigen-binding fragment thereof, that specifically binds to an epitope comprising amino acid residues 1-9 of hepcidin. In another embodiment, the antibody, or antigen-binding fragment thereof, specifically binds to 2, 3, 4, 5, 6, 7, 8, or 9 amino acid residues of an epitope comprising amino acid residues 1-9 of hepcidin.

In another embodiment, the antibody, or antigen-binding fragment thereof, is monoclonal antibody comprising a heavy chain CDR1 encoded by SEQ ID NO: 55, a heavy CDR2 encoded by SEQ ID NO: 58, a heavy chain CDR3 encoded by SEQ ID NO: 61, a light chain CDR1 encoded by SEQ ID NO: 64, a light CDR2 encoded by SEQ ID NO: 67, and a light chain CDR3 encoded by SEQ ID NO: 70.

In another embodiment, the antibody, or antigen-binding fragment thereof, is monoclonal antibody comprising a heavy chain CDR1 encoded by SEQ ID NO: 56, a heavy CDR2 encoded by SEQ ID NO: 59, a heavy chain CDR3 encoded by SEQ ID NO: 61, a light chain CDR1 encoded by SEQ ID NO: 65, a light CDR2 encoded by SEQ ID NO: 68, and a light chain CDR3 encoded by SEQ ID NO: 71.

In another embodiment, the antibody, or antigen-binding fragment thereof, is monoclonal antibody comprising a heavy chain CDR1 encoded by SEQ ID NO: 57, a heavy CDR2 encoded by SEQ ID NO: 60, a heavy chain CDR3 encoded by SEQ ID NO: 63, a light chain CDR1 encoded by SEQ ID NO: 66, a light CDR2 encoded by SEQ ID NO: 69, and a light chain CDR3 encoded by SEQ ID NO: 72.

The antibody may be, for example, a monoclonal antibody, a chimeric antibody, a human antibody, or a humanized antibody. In one embodiment, a humanized variable heavy chain comprises an amino acid sequence set forth as SEQ ID NO: 40. In another embodiment, a humanized variable light chain comprises an amino acid sequence set forth as SEQ ID NO: 38.

In one aspect, provided herein is an antibody, or antigen-binding fragment thereof, comprises a heavy chain variable region framework region; and a light chain variable region framework region as set forth in the Sequence Listing below where the CDRs identified in any one of SEQ ID NOS: 1-18 of 55-72 are inserted into the framework region utilizing Kabat numbering.

The antigen-binding fragment may be, for example, a Fab fragment, a Fab' fragment, a F(ab')$_2$ fragment, an Fv fragment, an scFv fragment, a single chain binding polypeptide, a Fd fragment, a variable heavy chain, a variable light chain, a dAb fragment or any other type of fragment described herein. An antigen-binding fragment may be, for example, an AVIMER, a diabody, or a heavy chain dimer. A heavy chain dimer may be, for example, a camelid or a shark heavy chain construct.

An antibody, or antigen-binding fragment thereof, described herein may have a dissociation constant (Kd) of about 1 to about 10 pM, from about 10 to about 20 pM, from about 1 to about 29 pM, from about 30 to about 40 pM, from about 10 to about 100 pM, or from about 20 to about 500 pM.

An antibody, or antigen-binding fragment thereof, described herein may have a dissociation constant (Kd) of less than about 500 pM, less than about 400 pM, less than about 300 pM, less than about 200 pM, less than about 100 pM, less than about 75 pM, less than about 50 pM, less than about 30 pM, less than about 25 pM, less than about 20 pM, less than about 18 pM, less than about 15 pM, less than about 10 pM, less than about 75. pM, less than about 5 pM, less than about 2.5 pM, or less than about 1 pM.

An antibody, or antigen-binding fragment thereof, described herein may have an affinity for hepcidin or a hepcidin peptide of from about $10^{-9}$ to about $10^{-14}$, from about $10^{-10}$ to about $10^{-14}$, from about $10^{-11}$ to about $10^{-14}$, from about $10^{-12}$ to about $10^{-14}$, from about $10^{-13}$ to about $10^{-14}$, from about $10^{-10}$ to about $10^{-11}$, from about $10^{-11}$ to about $10^{-12}$, from about $10^{-12}$ to about $10^{-13}$, or $10^{-13}$ to about $10^{-14}$.

Provided herein is a composition, comprising an antibody, or antigen-binding fragment, and an acceptable carrier or excipient. Compositions are described in more detail below.

Also provided herein is an isolated nucleic acid molecule comprising a nucleotide sequence that encodes an antibody, or antigen-binding fragment thereof, described herein. Also provided herein is an expression vector comprising the nucleic acid molecule, operably linked to a regulatory control sequence. Also provided herein is a host cell comprising a vector or a nucleic acid molecule provided herein. Also provided herein is a method of using the host cell to produce an antibody, comprising culturing the host cell under suitable conditions such that the nucleic acid is expressed to produce the antibody.

Compositions

Each of the compounds described herein can be used as a composition when combined with an acceptable carrier or excipient. Such compositions are useful for in vitro or in vivo analysis or for administration to a subject in vivo or ex vivo for treating a subject with the disclosed compounds.

Thus pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Pharmaceutical formulations comprising a protein of interest, e.g., an antibody or antigen-binding fragment, identified by the methods described herein can be prepared for storage by mixing the protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Acceptable carriers are physiologically acceptable to the administered subject and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier is acceptable in the sense of being compatible with the other ingredients of the formulation and not injurious to a subject to whom it is administered. Nor should an acceptable carrier alter the specific activity of the subject compounds.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. The pharmaceutical compositions and formulations include an amount of a compound described herein and a pharmaceutically or physiologically acceptable carrier.

Compositions can be formulated to be compatible with a particular route of administration (i.e., systemic or local). Thus, compositions include carriers, diluents, or excipients suitable for administration by various routes.

In another embodiment, the compositions can further comprise, if needed, an acceptable additive in order to improve the stability of the compounds in composition and/or to control the release rate of the composition. Acceptable additives do not alter the specific activity of the subject compounds. Exemplary acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, exemplary acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

In one embodiment, a composition may contain an isotonic buffer such as a phosphate, acetate, or TRIS buffer in combination with a tonicity agent such as a polyol, Sorbitol, sucrose or sodium chloride, which tonicifies and stabilizes. A tonicity agent may be present in the composition in an amount of about 5%.

In another embodiment, the composition may include a surfactant such as to prevent aggregation and for stabilization at 0.01 to 0.02% wt/vol.

In another embodiment, the pH of the composition may range from 4.5-6.5 or 4.5-5.5.

Other exemplary descriptions of pharmaceutical compositions for antibodies may be found in, for example, US 2003/0113316 and U.S. Pat. No. 6,171,586, each incorporated herein by reference in its entirety.

A composition herein may also contain more than one active compound as necessary for the particular indication being treated, such as those with complementary activities that do not adversely affect each other. For example, a method of treatment may further provide an immunosuppressive agent. Such molecules are suitably present in combination in amounts that are effective for the purpose intended.

Active ingredients may be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antibodies are also contemplated herein; methods to make suspensions and crystal forms are known to one of skill in the art.

A composition to be used for in vivo administration must be sterile. In some embodiments, the compositions of the invention may be sterilized by conventional, well known sterilization techniques. For example, sterilization may be readily accomplished by filtration through sterile filtration membranes. The resulting solutions may be packaged for use or filtered under aseptic conditions and lyophilized, the lyophilized preparation being combined with a sterile solution prior to administration.

Freeze-drying may be employed to stabilize polypeptides for long-term storage, such as when a polypeptide is relatively unstable in liquid compositions. A lyophilization cycle is usually composed of three steps: freezing, primary drying, and secondary drying; Williams and Polli, *Journal of Parenteral Science and Technology*, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use. Standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, *Drug Development and Industrial Pharmacy*, Volume 18, Numbers 11 and 12, pages 1311-1354 (1992).

Some excipients such as, for example, polyols (including mannitol, sorbitol and glycerol); sugars (including glucose and sucrose); and amino acids (including alanine, glycine and glutamic acid), may act as stabilizers for freeze-dried products; see, e.g., Carpenter et al., *Developments in Biological Standardization*, Volume 74, pages 225-239 (1991). Polyols and sugars may also be used to protect polypeptides from freezing and drying-induced damage and to enhance the stability during storage in the dried state. Sugars may be effective in both the freeze-drying process and during storage. Other classes of molecules, including mono- and disaccharides and polymers such as PVP, have also been reported as stabilizers of lyophilized products.

For injection, a composition and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the compositions may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (see, e.g., U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. While encapsulated antibodies remain in the body for a long time, they may denature or aggregate as a result of exposure to moisture at 37° C., resulting in a loss of biological activity and possible changes in immunogenicity.

Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

A composition described herein may be designed to be short-acting, fast-releasing, long-acting, or sustained-releasing as described herein. In one embodiment, the composition may be formulated for controlled release or for slow release.

The pharmaceutical composition can be administered, for example, by injection, including, but not limited to, subcutaneous, intravitreal, intradermal, intravenous, intra-arterial, intraperitoneal, intracerebreospinal, or intramuscular injection. Excipients and carriers for use in formulation of compositions for each type of injection are contemplated herein. The following descriptions are by example only and are not meant to limit the scope of the compositions. Compositions for injection include, but are not limited to, aqueous solutions (where water soluble) or dispersions, as well as sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation are vacuum drying and freeze drying which yields a powder of the active ingredient plus any additional desired ingredient from a previously sterile-filtered solution thereof.

Compositions can be conventionally administered intravitreally, sub-cutaneous, or via intravitreal implant.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Additionally, compositions can be administered via aerosolization. (Lahn et al., Aerosolized Anti-T-cell-Receptor Antibodies Are Effective against Airway Inflammation and Hyperreactivity, *Int. Arch. Allergy Immuno.,* 134: 49-55 (2004)).

In one embodiment, the composition is lyophilized, for example, to increase shelf-life in storage. When the compositions are considered for use in medicaments or any of the methods provided herein, it is contemplated that the composition can be substantially free of pyrogens such that the composition will not cause an inflammatory reaction or an unsafe allergic reaction when administered to a human subject. Testing compositions for pyrogens and preparing compositions substantially free of pyrogens are well understood to one or ordinary skill of the art and can be accomplished using commercially available kits.

Acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) *Pharm Res.* 13:1760 1764; Samanen (1996) *J. Pharm. Pharmacol.* 48:119 135; and U.S. Pat. No. 5,391,377, describing lipid compositions for oral delivery of therapeutic agents).

The phrase "pharmaceutically acceptable" refers to molecular entities and compositions that are physiologically tolerable and do not typically produce an allergic or similar untoward reaction, such as gastric upset, dizziness and the like, when administered to a human.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion that is sufficient to maintain concentrations in the blood are contemplated.

One embodiment contemplates the use of the compositions described herein to make a medicament for treating a condition, disease or disorder described herein. Medicaments can be formulated based on the physical characteristics of the subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below. The invention is further directed to medicaments of an anti-hepcidin antibody or antigen binding fragment thereof described hereinabove and a pharmaceutically acceptable carrier.

Provided herein are compositions of antibodies and antigen-binding fragments thereof that bind hepcidin and include those such as described elsewhere herein. Antibodies and antigen-binding fragments thereof that bind hepcidin as described herein can be used for the treatment of various diseases and conditions associated with iron homeostasis.

A composition (an antibody or an antigen-binding fragment described herein) can be administered alone or in combination with a second composition either simultaneously or sequentially dependent upon the condition to be treated. In one embodiment, a second therapeutic treatment is an erythropoiesis stimulator. When two or more compositions are administered, the compositions can be administered in combination (either sequentially or simultaneously). A composition can be administered in a single dose or multiple doses.

When formulated for administration to human subjects, the compositions may be formulated to be free of pyrogens. Testing compositions for pyrogens and preparing pharmaceutical compositions free of pyrogens are well understood to one of ordinary skill in the art.

One embodiment contemplates the use of any of the compositions of the present invention to make a medicament for treating a disorder of the present invention. Medicaments can be formulated based on the physical characteristics of the subject needing treatment, and can be formulated in single or multiple formulations based on the disorder. Medicaments of the present invention can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages.

Diagnostics

Provided herein is a method of diagnosing a hepcidin-related disorder, comprising: (a) contacting a biological sample from a subject suspected of having said disorder with an antibody, or antigen-binding fragment thereof, described herein under conditions that allow binding of the antibody or antigen-binding fragment thereof, to hepcidin; and (b) detecting and/or quantitating the hepcidin bound to the antibody, or antigen-binding fragment thereof, wherein the amount of hepcidin in the sample, as quantitated in (b), above a threshold level indicates the presence of hepcidin-related disorder and below the threshold level indicates the absence of hepcidin-related disorder.

A method of differentiating an inflammatory disease from a non-inflammatory disease, comprising: (a) contacting a biological sample from a human suspected of having said disorder with an antibody or antigen-binding fragment thereof, described herein under conditions that allow binding of the antibody or antigen-binding fragment thereof, to hepcidin; and (b) detecting and/or quantitating the hepcidin bound to the antibody or antigen-binding fragment thereof, wherein the amount of hepcidin, as quantitated in (b), above a threshold level indicates the presence of inflammatory disease and below the threshold level indicates the absence of inflammatory disease.

In one embodiment, the antibody or antigen-binding fragment further comprises a detectable moiety. Detection can occur in vitro, in vivo or ex vivo. In vitro assays for the detection and/or determination (quantification, qualification, etc.) of hepcidin with the antibodies or antigen-binding fragments thereof include but are not limited to, for example, ELISAs, RIAs and western blots. In vitro detection, diagnosis or monitoring of hepcidin can occur by obtaining a sample (e.g., a blood sample) from a subject and testing the sample in, for example, a standard ELISA assay. For example, a 96-well microtiter plate can be coated with an antibody or antigen-binding fragment thereof described herein, washed and coating with PBS-Tween/BSA to inhibit non-specific binding. The blood sample can be serially diluted and placed in single or duplicate wells compared to a serially-diluted standard curve of hepcidin. After incubating and washing the wells, an anti-hepcidin antibody labeled with biotin can be added, followed by addition of streptavidin-alkaline phosphatase. The wells can be washed and a substrate (horseradish peroxidase) added to develop the plate. The plate can be read using a conventional plate reader and software.

When detection occurs in vivo, contacting occurs via administration of the antibody or antigen binding fragment using any conventional means such as those described elsewhere herein. In such methods, detection of hepcidin in a sample or a subject can be used to diagnose a disease or disorder associated with, or correlated with the activity of such as those diseases and disorders described herein.

In the in vivo detection, diagnosis or monitoring of hepcidin, a subject is administered an antibody or antigen-binding fragment that binds to hepcidin, which antibody or antigen-binding fragment is bound to a detectable moiety. The detectable moiety can be visualized using art-recognized methods such as, but not limited to, magnetic resonance imaging (MRI), fluorescence, radioimaging, light sources supplied by endoscopes, laparoscopes, or intravascular catheter (i.e., via detection of photoactive agents), photoscanning, positron emission tomography (PET) scanning, whole body nuclear magnetic resonance (NMR), radioscintography, single photon emission computed tomography (SPECT), targeted near infrared region (NIR) scanning, X-ray, ultrasound, etc. such as described, for example, in U.S. Pat. No. 6,096,289, U.S. Pat. No. 7,115,716, U.S. Pat. No. 7,112,412, U.S. Patent Application No. 20030003048 and U. S. Patent Application No. 20060147379, each of which is incorporated herein in its entirety by reference. Labels for detecting compounds using such methods are also known in the art and described in such patents and applications and are incorporated herein by reference. Visualization of the detectable moiety can allow for detection, diagnosis, and/or monitoring of a condition or disease associated with hepcidin.

Additional diagnostic assays that utilize antibodies specific to the desired target protein, i.e., hepcidin, are known in the art and are also contemplated herein.

For in vitro detection methods, samples to be obtained from a subject include, but are not limited to, blood, tissue biopsy samples and fluid therefrom.

Thus, the present invention provides humanized antibodies and antigen-binding fragments thereof against hepcidin which are useful for detecting or diagnosing levels of hepcidin associated with a disease or disorder, potentially indicating need for therapeutic treatment. In certain embodiments, the antibodies comprise a humanized anti-hepcidin antibody described herein. In other embodiments the antibody further comprises a second agent. Such an agent can be a molecule or moiety such as, for example, a reporter molecule or a detectable label. Detectable labels/moieties for such detection methods are known in the art and are described in more detail below. Reporter molecules are any moiety which can be detected using an assay. Non-limiting examples of reporter molecules which have been conjugated to polypeptides include enzymes, radiolabels, haptens, fluorescent labels, phosphorescent molecules, chemiluminescent molecules, chromophores, luminescent molecules, photoaffinity molecules, colored particles or ligands, such as biotin. Detectable labels include compounds and/or elements that can be detected due to their specific functional properties, and/or chemical characteristics, the use of which allows the polypeptide to which they are attached to be detected, and/or further quantified if desired. Many appropriate detectable (imaging) agents are known in the art, as are methods for their attachment to polypeptides (see, for e.g., U.S. Pat. Nos. 5,021,236; 4,938,948; and 4,472,509, each of which is hereby incorporated by reference).

Methods of joining polypeptides such as antibodies with detectable moieties are known in the art and include, for example, recombinant DNA technology to form fusion proteins and conjugation (e.g., chemical conjugation). Methods for preparing fusion proteins by chemical conjugation or recombinant engineering are well-known in the art. Methods of covalently and non-covalently linking components are also known in the art. See, e.g., Williams (1995) Biochemistry 34:1787 1797; Dobeli (1998) Protein Expr. Purif. 12:404-414; and Kroll (1993) DNA Cell. Biol. 12: 441-453.

It may be necessary, in some instances, to introduce an unstructured polypeptide linker region between a label or a moiety and one or more portion of the antibodies, antigen-binding fragments or binding proteins described herein. A linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. One linker sequence is the linker found between the C-terminal and N-terminal domains of the RNA polymerase a subunit. Other examples of naturally occurring linkers include linkers found in the 1CI and LexA proteins.

Within a linker, an amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact deoxyribose nucleic acid (DNA), thereby influencing binding affinity or specificity, or to interact with other proteins. In some cases, such as when it is necessary to span a longer distance between subunits or when the domains must be held in a particular configuration, the linker can, optionally, contain an additional folded domain. In some embodiments, the design of a linker can involve an arrangement of domains which requires the linker to span a relatively short distance, e.g., less than about 10 Angstroms (Å). However, in certain embodiments, linkers span a distance of up to about 50 Angstroms.

Within the linker, the amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. In some cases, when it is necessary to span a longer distance between subunits or when the domains must be held in a particular configuration, the linker can optionally contain an additional folded domain.

Methods for coupling polypeptides (free or cell-bound) to beads are known in the art. Methods for selecting coupled polypeptides or cells displaying a polypeptide are also known in the art. Briefly, paramagnetic polystyrene microparticles are commercially available (Spherotech, Inc., Libertyville, Ill.; Invitrogen, Carlsbad, Calif.) that couple peptides to microparticle surfaces that have been modified with functional groups or coated with various antibodies or ligands such as, for example, avidin, streptavidin or biotin.

The paramagnetic property of microparticles allows them to be separated from solution using a magnet. The microparticles can be easily re-suspended when removed from the magnet. Polypeptides can be coupled to paramagnetic polystyrene microparticles coated with a polyurethane layer in a tube. The hydroxy groups on the microparticle surface are activated by reaction with p-toluensulphonyl chloride (Nilsson K and Mosbach K. "p-Toluenesulfonyl chloride as an activating agent of agarose for the preparation of immobilized affinity ligands and proteins." *Eur. J. Biochem.* 1980: 112: 397-402). Alternatively, paramagnetic polystyrene microparticles containing surface carboxylic acid can be activated with a carbodiimide followed by coupling to a polypeptide, resulting in a stable amide bond between a primary amino group of the polypeptide and the carboxylic acid groups on the surface of the microparticles (Nakajima N and Ikade Y, Mechanism of amide formation by carbodiimide for bioconjugation in aqueous media, *Bioconjugate Chem.* 1995, 6(1): 123-130; Gilles Mass., Hudson A Q and Borders C L Jr, Stability of water-soluble carbodiimides in aqueous solution, *Anal Biochem.* 1990 Feb. 1; 184(2):244-248; Sehgal D and Vijay I K, a method for the high efficiency of water-soluble carbodiimide-mediated amidation, *Anal Biochem.* 1994 April; 218(1):87-91; Szajani B et al, Effects of carbodiimide structure on the immobilization of enzymes, *Appl Biochem Biotechnol.* 1991 August; 30(2): 225-231). Another option is to couple biotinylated polypeptides to paramagnetic polystyrene microparticles whose surfaces have been covalently linked with a monolayer of streptavidin. (Argarana C E, Kuntz I D, Birken S, Axel R, Cantor C R. Molecular cloning and nucleotide sequence of the streptavidin gene. Nucleic Acids Res. 1986; 14(4):1871-82; Pahler A, Hendrickson W A, Gawinowicz Kolks M A, Aragana C E, Cantor C R. Characterization and crystallization of core streptavidin. *J Biol Chem* 1987:262(29):13933-13937).

Polypeptides can be conjugated to a wide variety of fluorescent dyes, quenchers and haptens such as fluorescein, R-phycoerythrin, and biotin. Conjugation can occur either during polypeptide synthesis or after the polypeptide has been synthesized and purified. Biotin is a small (244 kilodaltons) vitamin that binds with high affinity to avidin and streptavidin proteins and can be conjugated to most peptides without altering their biological activities. Biotin-labeled polypeptides are easily purified from unlabeled polypeptides using immobilized streptavidin and avidin affinity gels, and streptavidin or avidin-conjugated probes can be used to detect biotinylated polypeptides in, for example, ELISA, dot blot or Western blot applications. N-hydroxysuccinimide esters of biotin are the most commonly used type of biotinylation agent. N-hydroxysuccinimide-activated biotins react efficiently with primary amino groups in physiological buffers to form stable amide bonds. Polypeptides have primary amines at the N-terminus and can also have several primary amines in the side chain of lysine residues that are available as targets for labeling with N-hydroxysuccinimide-activated biotin reagents. Several different N-hydroxysuccinimide esters of biotin are available, with varying properties and spacer arm length (Pierce, Rockford, Ill.). The sulfo-N-hydroxysuccinimide ester reagents are water soluble, enabling reactions to be performed in the absence of organic solvents.

The mole-to-mole ratio of biotin to polypeptide can be estimated using a 2-(4'-Hydroxyazobenzene-2-carboxylic acid) assay using art-recognized techniques (Green, N. Mex., (1975) "Avidin. In Advances in Protein Chemistry." Academic Press, New York. 29, 85-133; Green, N. Mex., (1971) "The use of bifunctional biotinyl compounds to determine the arrangement of subunits in avidin." *Biochem 1* 125, 781-791; Green, N. Mex., (1965) "A spectrophotometric assay for avidin and biotin based on binding of dyes by avidin." *Biochem. J.* 94: 23c-24c). Several biotin molecules can be conjugated to a polypeptide and each biotin molecule can bind one molecule of avidin. The biotin-avidin bond formation is very rapid and stable in organic solvents, extreme pH and denaturing reagents. To quantitate biotinylation, a solution containing the biotinylated polypeptide is added to a mixture of 2-(4'-Hydroxyazobenzene-2-carboxylic acid) and avidin. Because biotin has a higher affinity for avidin, it displaces the 2-(4'-Hydroxyazobenzene-2-carboxylic acid) and the absorbance at 500 nanometers decreases proportionately. The amount of biotin in a solution can be quantitated in a single cuvette by measuring the absorbance of the 2-(4'-Hydroxyazobenzene-2-carboxylic acid)-avidin solution before and after addition of the biotin-containing peptide. The change in absorbance relates to the amount of biotin in the sample by the extinction coefficient of the 2-(4'-Hydroxyazobenzene-2-carboxylic acid)-avidin complex.

Alternatively, an antibody, antigen-binding fragment or binding protein can be conjugated with a fluorescent moiety Conjugating polypeptides with fluorescent moieties (e.g., R-Phycoerythrin, fluorescein isothiocyanate (FITC), etc.) can be accomplished using art-recognized techniques described in, for example, Glazer, A N and Stryer L. (1984). *Trends Biochem.* Sci. 9:423-7; Kronick, M N and Grossman, P D (1983) *Clin. Chem.* 29:1582-6; Lanier, L L and Loken, M R (1984) *J. Immunol.*, 132:151-156; Parks, D R et al. (1984) *Cytometry* 5:159-68; Hardy, R R et al. (1983) Nature 306:270-2; Hardy R R et al. (1984) *J. Exp. Med.* 159:1169-88; Kronick, M N (1986) *J. Immuno. Meth.* 92:1-13; Der-Balian G, Kameda, N and Rowley, G. (1988) *Anal. Biochem.* 173:59-63.

In one non-limiting embodiment, an antibody antigen-binding fragment can be associated with (conjugated to) a detectable label, such as a radionuclide, iron-related compound, a dye, an imaging agent or a fluorescent agent for immunodetection of hepcidin which can be used to visualize binding of the antibodies to hepcidin in vitro and/or in vivo.

Non-limiting examples of radiolabels include, for example, $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81}MKr$, $^{87}MSr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, 166Ho, $^{169}Eu$, $^{177}Lu$, $^{186}Re$, $^{188}Re$, 189Re, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$. Radiolabels can be attached to compounds using conventional chemistry known in the art of antibody imaging. Radiolabeled compounds are useful in in vitro diagnostics techniques and in in vivo radioimaging techniques and in radioimmunotherapy.

In one embodiment, the antibody or antigen-binding fragment thereof can be conjugated to both a therapeutic moiety and a detectable moiety. An antibody or antigen-binding fragment thereof can be conjugated to, or recombinantly engineered with, an affinity tag (e.g., a purification tag). Affinity tags such as, for example, His6 tags (SEQ ID NO: 28) are conventional in the art.

Antibodies or antigen-binding fragments thereof provided herein are such that they can be conjugated or linked to a therapeutic moiety and/or an imaging or a detectable moiety and/or an affinity tag. Methods for conjugating or linking polypeptides are well known in the art. Associations (binding) between compounds and labels include any means known in the art including, but not limited to, covalent and non-covalent interactions, chemical conjugation as well as recombinant techniques.

Methods of Treatment

Provided herein is a method of inducing a response in a subject (human or non-human) by administering to the subject a composition of an antibody, or antigen-binding fragment thereof, that binds to hepcidin. The binding site to which the antibody binds can be a continuous or conformation/dis-continuous epitope. In one embodiment, an antibody, or antigen-binding fragment thereof, specifically binds to an epitope comprising amino acid residues 1-9 of hepcidin. In another embodiment, an antibody, or antigen-binding fragment thereof, specifically binds to 2, 3, 4, 5, 6, 7, 8 or 9 amino acid residues of an epitope comprising amino acid residues 1-9 of hepcidin. In yet another embodiment, an antibody, or antigen-binding fragment thereof, specifically binds to Hep-20, Hep-22, and Hep-25.

Hepcidin may have an amino acid sequence of, for example, SEQ ID NO: 19. A hepcidin peptide may have an amino acid sequence of, for example, any one of SEQ ID NOS: 20-25.

In yet another embodiment, an antibody, or antigen-binding fragment thereof, binds to an amino acid sequence set forth in any one of the peptide SEQ ID NOS described herein including, for example, SEQ ID NOS: 19-27.

An effective response of the present invention is achieved when the subject experiences partial or total alleviation or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month (mo), about at least 2 mos., about at least 3 mos., about at least 4 mos., about at least 6 mos., about at least 1 year, about at least 2 years, about at least 3 years, etc. Overall survival can be also measured in months to years. Alternatively, an effective response may be that a subject's symptoms remain static. Further indications of treatment of indications are described in more detail below.

Compositions of antibodies and antigen-binding fragments described herein can be used as non-therapeutic agents (e.g., as affinity purification agents). Generally, in one such embodiment, a protein of interest is immobilized on a solid phase such a Sephadex resin or filter paper, using conventional methods known in the art. The immobilized protein is contacted with a sample containing the target of interest (or fragment thereof) to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, which will release the target protein. In addition to purification, compositions can be used for detection, diagnosis and therapy of diseases and disorders described herein.

The term "contacting" as used herein refers to adding together a solution or composition of a compound with a liquid medium bathing the polypeptides, cells, tissue or organ from an organism. Alternately, "contacting" refers to mixing together a solution or composition of a compound, with a liquid such as blood, serum, or plasma derived from an organism. For in vitro applications, a composition can also comprise another component, such as dimethyl sulfoxide (DMSO). DMSO facilitates the uptake of the compounds or solubility of the compounds. The solution comprising the test compound may be added to the medium bathing the cells, tissues, or organs, or mixed with another liquid such as blood, by utilizing a delivery apparatus, such as a pipette-based device or syringe-based device. For in vivo applications, contacting can occur, for example, via administration of a composition to a subject by any suitable means; compositions with pharmaceutically acceptable excipients and carriers have been described in more detail above.

A "subject" (e.g., a mammal such as a human or a non-human animal such as a primate, rodent, cow, horse, pig, sheep, etc.) according to one embodiment of the present application, is a mammal who exhibits one or more clinical manifestations and/or symptoms of a disease or disorder described herein.

A composition described herein may be administered to a subject in a therapeutically effective amount which is effective for producing some desired therapeutic effect by inhibiting a disease or disorder such as described herein which can be associated with hepcidin, at a reasonable benefit/risk ratio applicable to any medical treatment. For the administration of the present compositions to human subjects, the compositions can be formulated by methodology known by one of ordinary skill in the art. A therapeutically effective amount is an amount that achieves at least partially a desired therapeutic or prophylactic effect in an organ or tissue. The amount of an anti-hepcidin antibody or antigen binding fragment thereof necessary to bring about prevention and/or therapeutic treatment of a disease or disorder is not fixed per se. The amount of anti-hepcidin antibody or antigen binding fragment thereof administered may vary with the type of disease, extensiveness of the disease, and size of the mammal suffering from the disease or disorder. In one embodiment, two or more anti-hepcidin antibodies described herein are administered to a subject in combination. Combination includes concomitant or subsequent administration of the antibodies.

"Administering" is defined herein as a means providing the composition to the subject in a manner that results in the composition being inside the subject's body. Such an administration can be by any route including, without limitation, locally, regionally or systemically by subcutaneous, intravitreal, intradermal, intravenous, intra-arterial, intraperitoneal, intracerebreospinal, or intramuscular administration (e.g., injection). "Concurrent administration" means administration within a relatively short time period from each other; such time period can be less than 2 weeks, less than 7 days, less than 1 day and could even be administered simultaneously.

Actual dosage levels of the active ingredients in the compositions can be varied so as to obtain an amount of the active ingredient that is effective to achieve the desired therapeutic response for a particular subject, composition, and mode of administration, without being toxic to the subject. The selected dosage level will depend upon a variety of factors including the activity of the particular compound employed, the route of administration, the time of administration, the rate of excretion of the particular compound being employed, the duration of the treatment, other drugs, compounds and/or materials used in combination with the particular composition employed, the age, sex, weight, condition, general health and prior medical history of the subject being treated, and like factors well known in the medical arts.

The antibodies and antigen-binding fragments described herein may be administered to a subject in various dosing amounts and over various time frames. Non-limiting doses include about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or any integer in between. Additionally, the dose(s) of an antibody or antigen-binding fragment can be administered twice a week, weekly, every two weeks, every three weeks, every 4 weeks, every 6 weeks, every 8 weeks, every 12 weeks, or any combination of weeks therein. Dosing cycles are also contemplated such as, for example, administering antibodies or antigen-binding fragments thereof once or twice a week for 4 weeks, followed by two weeks without therapy. Additional dosing cycles including, for example, different combinations of the doses and weekly cycles described herein are also contemplated within the invention.

Therapeutically effective amounts of a composition may vary and depend on the severity of the disease and the weight and general state of the subject being treated, but generally range from about 1.0 µg/kg to about 100 mg/kg body weight, or about 10 µg/kg to about 30 mg/kg, or about 0.1 mg/kg to about 10 mg/kg or about 1 mg/kg to about 10 mg/kg per application. Administration can be daily, on alternating days, weekly, twice a month, monthly or more or less frequently, as necessary depending on the response to the disorder or condition and the subject's tolerance of the therapy. Maintenance dosages over a longer period of time, such as 4, 5, 6, 7, 8, 10 or 12 weeks or longer may be needed until a desired suppression of disorder symptoms occurs, and dosages may be adjusted as necessary. The progress of this therapy is easily monitored by conventional techniques and assays.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

In some embodiments, the specific binding agent or antibody of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

"Contacting" is defined herein as a means of bringing a composition as provided herein in physical proximity with a cell, organ, tissue or fluid as described herein. Contacting encompasses systemic or local administration of any of the compositions provided herein and includes, without limitation, in vitro, in vivo and/or ex vivo procedures and methods. "Combining" and "contacting" are used interchangeably herein and are meant to be defined in the same way.

An antibody described herein may be administered by any suitable means, either systemically or locally, including via parenteral, subcutaneous, intraperitoneal, intracerebreospinal, intrapulmonary, and intranasal administration, and, if desired for local treatment, intralesional administration. Parenteral routes include intravenous, intraarterial, intraperitoneal, epidural, intrathecal administration. In addition, the specific binding agent or antibody is suitably administered by pulse infusion, particularly with declining doses of the specific binding agent or antibody. In one embodiment, compositions may be administered given by injection depending in part on whether the administration is brief or chronic. Other modes of administration methods are contemplated, including topical, particularly transdermal, transmucosal, rectal, oral or local administration e.g. through a catheter placed close to the desired site.

A response is achieved when the subject experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors. Prolonging survival includes without limitation times of at least 1 month (mo), about at least 2 months (mos.), about at least 3 mos., about at least 4 mos., about at least 6 mos., about at least 1 year, about at least 2 years, about at least 3 years, or more. Overall survival can also be measured in months to years. The subject's symptoms can remain static or can decrease.

A physician or veterinarian having ordinary skill in the art can readily determine and prescribe the effective amount (ED50) of the composition required. For example, the physician or veterinarian could start doses of the compounds employed in the composition at levels lower than that required in order to achieve the desired therapeutic effect and gradually increase the dosage until the desired effect is achieved. Alternatively, a dose can remain constant.

Compositions can be administered to a subject by any convenient route such as described above. Regardless of the route of administration selected, the compounds of the present invention, which can be used in a suitable hydrated form, and/or the compositions, are formulated into acceptable dosage forms such as described below or by other conventional methods known to those of skill in the art.

Antibodies and/or other agents may be combined in separate compositions for simultaneous or sequential administration. In one embodiment, simultaneous administration comprises one or more compositions that are administered at the same time, or within 30 minutes of each other. Administration may occur at the same or different sites.

Toxicity and therapeutic efficacy of such ingredient can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. While compounds that exhibit toxic side effects may be used, care should be taken to design a delivery system that targets such compounds to the site of affected tissue in order to minimize potential damage to healthy cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration arrange that includes the $IC_{50}$ (i.e., the concentration of the test compound which achieves a half-maximal inhibition) as determined in cell culture. Levels in plasma can be measured, for example, by high performance liquid chromatography. Such information can be used to more accurately determine useful doses in humans.

As used herein, an antibody, or antigen-binding fragment thereof, may be a hepcidin activity antagonist, meaning a substance that inhibits hepcidin's iron-regulating activity.

In one aspect, the hepcidin activity antagonist can be a substance that inhibits the function of hepcidin, for example, by inhibiting binding between hepcidin and ferroportin, by inhibiting hepcidin-controlled cellular iron retention, or by facilitating ferroportin dependent iron transport. Hepcidin activity antagonists include antibodies, or antigen-binding fragments thereof, that bind hepcidin and inhibit its activity. An antibody, or antigen-binding fragment thereof, may in some instances, bind to ferroportin but do not activate ferroportin iron transport.

In yet other embodiments, an antibody, or antigen-binding fragment thereof, described herein may inhibit (or neutralize) hepcidin iron-regulating activity, in vitro and/or also in vivo. Such hepcidin-neutralizing antibodies are therapeutically useful for hepcidin-related disorders or disorders of iron homeostasis. Hepcidin neutralizing activity may be measured, for example, through a number of markers such as ferritin/iron levels, red blood cell count, red blood cell characteristics (hemoglobin content and/or cell volume), early red blood cell characteristics (reticulocyte numbers, hemoglobin content or cell volume), ferroportin internalization, or iron transport. In one non-limiting embodiment, an antibody, or antigen-binding fragment thereof, described herein decreases intracellular iron concentration at an $EC_{50}$ of about $10^{-8}$M or less and/or increases circulating iron concentration.

An antibody, or antigen-binding fragment thereof, described herein may antagonize the effect of human hepcidin or inhibit hepcidin iron-regulating activity. In some embodiments, an antibody, or antigen-binding fragment thereof, described herein exerts an effect at an $EC_{50}$ of about $1 \times 10^{-8}$M or less, or about $1 \times 10^{-7}$ M or less. For example, an antibody may decrease the intracellular iron level in a cell at an $EC_{50}$ of about $1 \times 10^{-8}$M or less, or may reduce ferritin expression at an $EC_{50}$ of about $1 \times 10^{-8}$M or less, as determined by a ferritin assay. In other embodiments, an antibody as described herein may reduce free serum hepcidin levels by at least about 20%, by at least about 30%, by at least about 40%, by at least about 50%, by at least about 60%, by at least about 70%, by at least about 80%, or by at least about 90% compared to a control antibody or compared to a placebo. In other embodiments, an antibody as described herein may increase red blood cell count (number), red blood cell mean cell volume or red blood cell hemoglobin content, increase hemoglobin, increase hematocrit, increase % Tsat, increase circulating (or serum) iron levels, and/or increase or normalize reticulocyte count, reticulocyte mean cell volume, reticulocyte hemoglobin content or reticulocyte numbers.

Provided herein are diagnostic methods utilizing an antibody or antigen-binding fragment thereof, described herein. An antibody, or antigen-binding fragment thereof, described herein, may also be used for purification purposes.

Also provided herein are therapeutic methods utilizing an antibody or antigen-binding fragment thereof, described herein. Such antibodies, or antigen-binding fragments thereof, may be used to treat a hepcidin-related disorder. Hepcidin-related disorders, inflammatory diseases, and diseases or disorders of iron homeostasis for which the methods may be applied include but are not limited to African iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, acute kidney injury (AKI), cirrhosis of liver, classic hemochromatosis, collagen-induced arthritis (CIA), conditions with hepcidin excess (elevated hepcidin), congenital dyserythropoietic anemia, congestive heart failure, Crohn's disease, Celiac disease, inflammatory bowel disease (IBD), diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, *H. pylori* infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hepcidin deficiency, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin, TMPRSS6 (IRIDA), or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

As used herein, "treatment" or "treat" refers to both prophylactic treatment of a subject at risk of, or having a predisposition toward, a disease or disorder, and to therapeutic treatment of a subject suffering from a disease or disorder.

Administration of a therapeutic agent in a prophylactic method can occur prior to the manifestation of symptoms of an undesired disease or disorder, such that the disease or disorder is prevented or, alternatively, delayed in its progression. Thus, when used in conjunction with prophylactic methods, the term "therapeutically effective" means that, after treatment, a fewer number of subjects (on average) develop the undesired disease or disorder or progress in severity of symptoms.

When used in conjunction with therapeutic methods involving administration of a therapeutic agent after the subject manifests symptoms of a disease or disorder, the term "therapeutically effective" means that, after treatment, one or more signs or symptoms of the disease or disorder is ameliorated or eliminated.

As used herein, a "hepcidin-related disorder" refers to a condition caused by or associated with an abnormal level of hepcidin (e.g., hepcidin excess or hepcidin deficiency relative to the degree of anemia or iron stored) which disrupts iron homeostasis. A disruption in iron homeostasis can in turn result in secondary diseases such as anemia. Acute or chronic inflammatory conditions can result in up-regulation of hepcidin expression, which can result in decreased circulating iron levels, which can cause anemia or worsen existing anemia. Exemplary hepcidin-related inflammatory diseases include anemia of cancer, anemia of chronic disease, anemia of inflammation, chemotherapy-induced anemia, chronic kidney disease (stage I, II, III, IV or V), end stage renal disease, chronic renal failure congestive heart failure, cancer, rheumatoid arthritis, systemic lupus erythematosus, Crohn's disease, *H. pylori* infection or other bacterial infections, hepatitis C, HIV, and other viral illnesses, arteriosclerosis, atherosclerosis, cirrhosis of the liver, pancreatitis, sepsis, vasculitis, iron-deficiency, hypochromic microcytic anemia and conditions with hepcidin excess.

As used herein, the phrase "disease (or disorder) of iron homeostasis" refers to a condition in which a subject's iron levels require modulation. It includes hepcidin-related disorders; conditions not associated with elevated levels of hepcidin that nevertheless would benefit from inhibition of hepcidin activity, such as a disruption in iron homeostasis not caused by hepcidin; diseases where aberrant iron absorption, recycling, metabolism or excretion causes a disruption in normal iron blood levels or tissue distribution; diseases where iron dysregulation is a consequence of another disease or condition, such as inflammation, cancer or chemotherapy; diseases or disorders resulting from abnormal iron blood levels or tissue distribution; and diseases or disorders that can be treated by modulating iron levels or distribution. Non-limiting examples of such diseases or disorders of iron homeostasis, hepcidin-related disorders and inflammatory conditions which can result in hepcidin excess include African iron overload, iron refractory iron deficiency anemia (IRIDA), alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, acute kidney injury (AKI), cardiopulmonary bypass-associated AKI, drug or toxin-associated AKI, cirrhosis of liver, classic hemochromatosis, collagen-induced arthritis (CIA), conditions with hepcidin excess (elevated hepcidin), congenital dyserythropoietic anemia, congestive heart failure, Crohn's disease, Celiac disease, inflammatory bowel disease (IBD), diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, Gracile syndrome, *H. pylori* infection or other bacterial infections, Hallervordan Spatz disease, hereditary hemochromatosis, acquired hemochromatosis, hemochromatosis resulting from mutations in transferrin receptor 2, hemoglobinopathies, hepatitis, hepatitis (Brock), hepatitis C, hepatocellular carcinoma, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

Non-inflammatory conditions which are implicated in a disruption of iron regulation include, but are not limited to, vitamin B6 deficiency, vitamin B12 deficiency, folate deficiency, pellagra, funicular myelosis, pseudoencephalitis, Parkinson's disease (Fasano et al., J. Neurochem. 96:909 (2006) and Kaur et al., Ageing Res. Rev., 3:327 (2004)), Alzheimer's disease, coronary heart disease, osteopenia and osteoporosis (Guggenbuhl et al., Osteoporos. Int. 16:1809 (2005)), hemoglobinopathies and disorders of red cell metabolism (Papanikolaou et al., Blood 105:4103 (2005)), and peripheral occlusive arterial disease.

In one aspect, provided herein is a method of treating a disorder of iron homeostasis in a subject in need thereof, comprising administering to said subject a composition described herein. In another aspect, provided herein is a method of modulating hepcidin activity in a subject in need thereof, comprising administering to said subject a composition described herein. In yet another aspect, provided herein is a method for treating a disorder of iron homeostasis in a subject in need thereof, comprising administering to said subject a composition described herein. In yet another aspect, provided herein is a method of treating hemochromatosis in a subject in need thereof, comprising administering to said subject a composition described herein. In yet another aspect, provided herein is a method of treating a subject with an elevated level of hepcidin, comprising administering to said subject a pharmaceutical composition described herein. In yet another aspect, provided herein is a method of treating anemia in a subject in need thereof, comprising administering to said subject a composition described herein. In yet another aspect, provided herein is a method of treating an inflammatory disease in a subject in need thereof, comprising administering to said subject a composition described herein. In yet another aspect, provided herein is a method of treating an infection in a subject in need thereof, comprising administering to said subject a composition described herein. An infection may be, for example, a bacterial, fungal, or viral infection.

Any of such methods may, in some instances, further comprise administering to said subject an erythropoiesis stimulator, wherein said erythropoiesis stimulator is selected from the group consisting of erythropoietin, an erythropoietin variant and an antibody that binds erythropoietin. In one embodiment, the antibody, or antigen-binding fragment thereof, that specifically binds hepcidin and said erythropoiesis stimulator are administered concurrently or sequentially. As used herein, the term "erythropoietic activity" means activity to stimulate erythropoiesis as demonstrated in an in vivo assay, for example, the exhypoxic polycythemic mouse assay. See, e.g., Cotes and Bangham, Nature 191:1065 (1961).

In one embodiment, an antibody, or antigen-binding fragment thereof, described herein and an erythropoiesis stimulator may be used to improve treatment of a patient with anemia. In another embodiment, patients who are hypo-responsive to, including unresponsive to, erythropoiesis stimulator therapy, such as erythropoietin or analogs thereof (Epoetin alfa, Epoetin beta, darbepoetin alfa), among others, may benefit from co-treatment with a hepcidin activity antagonist or hepcidin expression inhibitor. In another embodiment, an antibody, or antigen-binding fragment thereof, described herein and an erythropoiesis stimulator may be used to improve treatment of a patient an iron loading disorder secondary to transfusion-dependent iron overload, or have an iron maldistribution disorder such as Friedreich's ataxia.

As used herein, "erythropoiesis stimulator" refers to a chemical compound that directly or indirectly causes activation of the erythropoietin receptor, for example, by binding to and causing dimerization of the receptor or by stimulating endogenous erythropoietin expression. Erythropoiesis stimulators include erythropoietin and variants, analogs, or derivatives thereof that bind to and activate erythropoietin receptor; antibodies that bind to erythropoietin receptor and activate the receptor; or peptides that bind to and activate erythropoietin receptor; or small organic chemical compounds, optionally less than about 1000 Daltons in molecular weight, that bind to and activate erythropoietin receptor. Erythropoiesis stimulators include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), mimetic antibodies and HIF inhibitors (see U.S. Patent Publication No. 2005/0020487, the disclosure of which is incorporated by reference in its entirety). Exemplary erythropoiesis stimulators include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and US publication nos. US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; US 2006/0111279.

In one embodiment, an antibody, or antigen-binding fragment thereof, described herein and an iron chelator to redistribute iron stores in the body is also contemplated. An iron chelator is an agent capable of binding iron and removing it from a tissue or from circulation. Examples include deferoxamine (Desferal®) and deferasirox (Exjade®), and deferiprone (1,2-dimethyl-3-hydroxypyridin-4-one).

Administration of a composition herein may be by any suitable means including, but not limited to, injection. In one embodiment, injection may be, for example, intravenous, subcutaneous, or intramuscular injection.

Packages, Kits, and Pre-Filled Containers

Also provided herein are kits containing one or more compounds described above. The kit may comprise an antibody or antigen-binding fragment thereof that binds hepcidin in suitable container means.

The container means of the kits will generally include at least one vial, test tube, flask, bottle, ampoule, syringe an intravenous (IV) bag and/or other container means, into which the at least one polypeptide can be placed, and/or preferably, suitably aliquoted. Provided herein is a container means comprising a composition described herein.

The kits may include a means for containing at least one fusion protein, detectable moiety, reporter molecule, and/or any other reagent containers in close confinement for commercial sale. Such containers may include injection and/or blow-molded plastic containers into which the desired vials are retained. Kits can also include printed material for use of the materials in the kit.

Packages and kits may additionally include a buffering agent, a preservative and/or a stabilizing agent in a pharmaceutical formulation. Each component of the kit can be enclosed within an individual container and all of the various containers can be within a single package. Invention kits can be designed for cold storage or room temperature storage.

Additionally, the preparations can contain stabilizers to increase the shelf-life of the kits and include, for example, bovine serum albumin (BSA). Where the compositions are lyophilized, the kit may contain further preparations of solutions to reconstitute the lyophilized preparations. Acceptable reconstitution solutions are well known in the art and include, for example, pharmaceutically acceptable phosphate buffered saline (PBS).

Packages and kits can further include one or more components for an assay, such as, for example, an ELISA assay. Samples to be tested in this application include, for example, blood, plasma, and tissue sections and secretions, urine, lymph, and products thereof. Packages and kits can further include one or more components for collection of a sample (e.g., a syringe, a cup, a swab, etc.).

Packages and kits can further include a label specifying, for example, a product description, mode of administration and/or indication of treatment. Packages provided herein can include any of the compositions as described herein. disease (e.g., IBD), rheumatoid arthritis, osteoarthritis, a forms of cancer and their metastases.

The term "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

In still further embodiments, a kit may further comprise a container means for an erythropoiesis stimulator.

Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a flash/cloud drive, disk (floppy diskette or hard disk), optical CD such as CD- or DVD-ROM/RAM, magnetic tape, electrical storage media such as RAM and ROM, IC tip and hybrids of these such as magnetic/optical storage media.

Provided herein is a container means comprising a composition described herein. The container means may be any suitable container which may house a liquid or lyophilized composition including, but not limited to, a vial, syringe, bottle, an in intravenous (IV) bag or ampoule. A syringe may be able to hold any volume of liquid suitable for injection into a subject including, but not limited to, 0.5 cc, 1 cc, 2 cc, 5 cc, 10 cc or more.

Provided herein are kits comprising a composition described herein. In one aspect, provided herein is a kit for treating a disorder associated with elevated hepcidin levels or a disorder of iron homeostasis, comprising an antibody, or an antigen-binding fragment thereof, as described herein and an erythropoiesis stimulator.

In another aspect, provided herein is a kit for treating a disorder associated with elevated hepcidin levels or a disorder of iron homeostasis, comprising an antibody, or an antigen-binding fragment thereof, as described herein, and a label attached to or packaged with the container, the label describing use of the antibody, or an antigen-binding fragment thereof, with an erythropoiesis stimulator.

In another aspect, provided herein is a kit for treating a disorder associated with elevated hepcidin levels, comprising an erythropoiesis stimulator and a label attached to or packaged with the container, the label describing use of the erythropoiesis stimulator with an antibody, or an antigen-binding fragment thereof, as described herein.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

Example 1. Monoclonal Antibody Development and Antigen Design to Human Hepcidin

Background

Hepcidin is a 25 amino acid peptide hormone that regulates iron homeostasis. Genetic or acquired hepcidin deficiency or excess is the main or contributing cause of major diseases of iron regulation. In other diseases where iron homeostasis is disturbed by the primary deficiency or excess of body iron stores, blood hepcidin concentrations reflect the physiologic responses to the primary disturbance. Despite the potential importance of hepcidin-25 directed therapies in clinical medicine, only one humanized monoclonal antibody has entered into early Phase 1 clinical studies.

The amino acid sequence of mature hepcidins is highly conserved among mammals, particularly the N-terminus. Mouse and rat hepcidins are 76% and 64% identical to human hepcidin respectively. The distinctive structure of hepcidin is highly conserved evolutionarily, and the N-terminal 5 amino acids are absolutely required for bioactivity in vitro as the N-terminal amino acids are directly involved in binding Fpn and leading to internalization and degradation in lysozomes (Nemeth et al., 2006).

On the molecular level, this occurs by hepcidin causing the degradation of its receptor, ferroportin, the sole human iron channel, and trapping iron inside liver cells, macrophages, and cells lining the intestine where ferroportin is expressed. As plasma iron levels decrease, hepcidin levels decrease, and ferroportin is produced and trafficked to the cell membrane. This allows normal iron absorption and recycling to occur and provide iron required for blood production. The hepcidin-ferroportin iron-regulatory axis is the target of several novel therapeutic drug development efforts currently in pre-clinical and Phase I trials. However, only one humanized MAb directed against hepcidin is currently being evaluated in early Phase I studies.

Human embryonic kidney (HEK 293) cells have been stably transfected with a ponesterone inducible promoter that promotes high levels of expression of a murine ferroportin-GFP fusion protein (designated Ec:R50-GFP) to study ferroportin biology in vitro cell based assay.

The well-known difficulty in producing antibodies to hepcidin-25 is due to its compact shape and high degree of evolutionary conservation, particularly in the N-terminal region of the peptide in mammals, including those in use for MAb development efforts.

Other companies have directed their antibodies against linear peptides from the mature C-terminal region of hepcidin-25 (hepcidin (10-25)) [SEQ ID NO: 27], which is not useful for ELISA detection of biologically active hepcidin-25 and would not be expected to be effective in therapeutic applications (see, e.g., Geacintov et al., US2004/0096990 A1).

Antibodies Developed by the Present Inventors

Using our knowledge of the importance of the amino terminus of hepcidin-25 and its poor immunogenicity, we designed a suite of antigens and immunized groups of BALB/c mice to produce monoclonal antibodies to biologically active hepcidin-25.

Our antigen design was focused on producing MAbs to the N-terminus of hepcidin-25 and the full length, oxidized hepcidin-25 peptide. Examples of antigens that were designed leading to three functional MAbs described herein are shown in FIGS. 1 and 6.

A number of peptide antigens were tested in vivo in BALB/c mice for immunogenicity and to produce MAbs specific to hepcidin-25 using a number of synthetic methods to add haptens (e.g., DNP, PamCys) and immunogenic carrier proteins (e.g., KLH, mKLH, albumin, or Carrier Protein) and few proved to be suitable antigens (FIGS. 5 and 6).

Example 2: Hybridoma Protocol

Following antibody titer calculation, hybridomas are prepared using a commercially available fusion kit (Hy-Clone) or by the conventional methods described by Kohler and Milstein (Id.).

The purpose of this example is to describe the production of monoclonal antibodies by isolation of mouse lymphocytes from lymph nodes (LN) and/or spleen (S) after immunization, the production of hybridoma cells, and production and selection of positive clones which secrete the antigen-specific antibodies.

Procedure

Preparation of Myeloma Cells.

Two weeks before fusion, a Sp2/0 myeloma cell line is propagated in DEME medium, with 10% FCS, 8-Azaguanine and Pen-Strep. One week prior to cell fusion, the cells are cultured without 8-azaguanine and split the cells every other day. Cell density for fusion is $2\times10^5$/ml and 100 ml of these cells are required. The cells were split the day before the fusion and cell viability determined; viability is expected to be greater than 95%.

The SP2/0 cells were harvested by centrifugation at 300×g for 10 minutes and washed 3 times by adding 30 ml of ClonaCell-HY-Fusion Medium B. The cell pellets were resuspended in 25 ml of Medium B to contain $2\times10^7$ viable cells. After resuspension the cells were kept at room temperature (RT). This step may be performed simultaneously with, or after, the lymphocyte preparation.

Isolation of Mouse Lymph Nodes, Spleen and Lymphocytes

PEG and media (Medium A, B, C,) were prepared for fusion by pre-warming to 37° C.

Only mice that responded to immunization as determined by standard serum titer analysis using hepcidin-25 as the antigen are selected for hybridoma fusion. Hybridoma fusion was performed 3 days after the last boost with the selected antigen.

Each mouse was sacrificed using asphyxiation and cervical dislocation and sprayed with 75% ethanol. The mouse was placed with its ventral surface facing up on a dissection board and all limbs secured to the dissection board. All dissection techniques were performed using aseptic techniques and different sets of sterile instruments (scissors, forceps) were used for each step of the dissection to remove the spleen and lymph nodes (LN).

The LN (and/or spleen) was placed into one well of 6 well plate containing 2 ml of Medium A and the fat and connective tissue trimmed off. We set one disposable cell strainer on the top of a 50 ml conical centrifuge tube and transferred the LN (or spleen) into the strainer and cut LN (or spleen) into small pieces with sterile scissors and ground the tissue using the plunger of a 3 mL sterile syringe and passing 5-10 ml of Medium B through the strainer. We ground the tissue one more time and rinsed with 10 ml of Medium B (only the membrane should remain on the screen). The lymphocytes were gently pipetted and mixed by inversion and centrifuged at 400×g for 7 minutes. The supernatant was discarded and the cells re-suspended in 10 ml Medium B. Appropriate dilutions of the cells were then counted using a hemocytometer.

Fusion

The lymphocytes and myeloma cells were mixed at a 4:1 ratio (approximately $8 \times 10^7$ lymphocytes with $2 \times 10^7$ myeloma cells) in a 50 ml tube. Lymphocytes and myeloma cells ratio can be in the range from 10:1 to 1:1. The fused cells were centrifuged for 10 minutes at 400×g once and the cell mixture re-suspended in 30 ml Medium B and centrifuged at 800 g×5 min to get good adherence and promote fusion of the cells.

The media from was completely aspirated from the cell pellet and the bottom of the tube gently tapped since the pellet must be disrupted for optimal fusion. One ml of PEG solution was slowly added to the pellet drop wise using a one ml pipette over a period of one minute without stirring. The bottom of the tube was continually tapped gently over the next minute.

4 ml Medium B was slowly added to the fusion mixture with continuous tapping as before over a period of 4 minutes.

10 ml Medium B was slowly added to the cells, incubate for 15 minutes in water bath set at 37° C.

30 ml of Medium A was slowly added and the cells centrifuged at 400×g for 7 minutes. The supernatant was discarded and cells washed with 40 ml of Medium A to ensure that all PEG was removed.

The cell pellet was slowly re-suspended in 10 ml of Clonacell-HY Hybridoma Recovery Medium (Medium C) and transferred to a T-75 cm² tissue culture flask containing 20 ml of Medium C (total volume=30 ml). The cells incubated overnight in a humidified incubator at 37° C. in 5% $CO_2$ atmosphere.

Selection and Cloning

On the day before the fusion, the ClonaCell-Hy Hybridoma Selection Medium (Medium D) was placed at 2-8° C. and thawed overnight. On the day of the fusion, Medium D was shaken vigorously to mix contents well and let warm to room temperature.

The fused cell suspension was then transferred into a 50 ml conical tube and centrifuged for 10 minutes at 400×g at RT and the supernatant removed and discarded. The cells were re-suspended in Medium C to a total volume of 10 mL.

10 mL of the cell suspension was transferred into 90 mL of Medium D and mixed thoroughly by gently inverting the bottle several times. The hybridoma cell suspension was then transferred into a disposable reagent reservoir and allowed to sit for 15 minutes at RT to let any bubbles to rise to the top and disperse.

Using a multi-channel pipette and sterile pipette tips, the ClonaCell®-HY Medium D containing the hybridoma cells was dispensed in 60-80 µL volumes per well into 96-well plates. This typically yielded between 10-16 plates depending on the volume plated. The plates were incubated at 37° C. in a humidified, 5% $CO_2$ incubator. Following 8 days of undisturbed incubation, the wells were examined for the presence of colonies and gently overlain with 150 µL of pre-warmed ClonaCell®-HY Medium E onto the semi-solid medium of each well, regardless of the presence of colonies and analysis performed on all wells.

The plates were incubated for an additional 2-4 days at 37° C. in a humidified, 5% $CO_2$ incubator. The overlay incubation time may be increased further to ensure the detection of low expressing hybridomas.

100 µL of the overlaid ClonaCell®-HY Medium E was carefully removed without disturbing the colonies in the semi-solid medium. The supernatants were tested for specific antibodies using an assay system appropriate for the antigen involved e.g. Neutravidin ELISA, Mouse Mab Isotyping etc.

The contents of wells that tested positive for antibodies were gently re-suspended and transferred to wells of a 24-well plate containing one mL of ClonaCell®-HY Medium E to expand the hybridomas. When a positive well contained more than a single colony the clones were harvested separately and transferred to individual wells for expansion and retesting to determine which clone produces the antibody of interest.

Freezing Hybridomas

Cells were cryopreserved at a concentration of $2 \times 10^6$ cells per vial.

A 20% DMSO solution in Fetal Bovine Serum (FBS) was placed in a 50 mL conical tube and allowed to cool on ice. The appropriate volume of DMSO was slowly added and mixed well and filter sterilized using a 0.2 µm filter and keep on ice.

Harvest cells and re-suspend in cold FBS at twice the desired final cell concentration (e.g., suspend at $4 \times 10^6$ cells/mL for cells cryopreserved at $2 \times 10^6$ cells per cryovial).

For cryopreservation, the FBS/20% DMSO solution was slowly added at a ratio of 1:1 to the tube containing the cells with continuous mixing during the addition. One mL of cells in freezing medium was transferred to each cryovial. The final cell suspension was calculated be in 90% FBS containing 10% DMSO.

Cryovials were placed immediately into freezing containers and then moved into −80° C. freezer overnight. Next day, remove frozen vials from the freezing container and store in liquid nitrogen.

Example 3: Screening Hybridomas for Anti-Hepcidin Antibodies

After eight days of undisturbed incubsation following fusion, all wells were screened to identify murine hybridomas that secreted anti-human hepcidin antibodies. Briefly, one day before screening 100 µl of neutravidin (200 ng/well) prepared in carbonate coating buffer (pH 9.6) was placed into each well of an enzyme immunoassay (EIA) plate and incubated overnight at 4° C. The following day the plate was washed, blocked with 1% BSA in buffer, and 1 ng of K18-Biotin hepcidin-25 tracer was added to each well. After one hour incubation, the plate was washed, 100 µl of hybridoma tissue culture supernatant was combined with 50 µl of 1% BSA/TBST in each well and the plate incubated on a rotary shaker (240 rpm) for 1.5 h. The plate was washed and a HRP-labeled goat anti-mouse IgG (H+L) chain detecstion antibody was added and incubation continued for another hour. The plate was washed, substrate applied, the reaction developed for 10 min before stopping with 1N $H_2SO_4$ and the absorbance read at 450 nM. An example of this first round screen yielded an 8×12 matrix of OD values as depicted in FIG. 2. Hybridomas that produced an OD>2.0 were identified and further propagated prior to the second round screen.

The second round of screening involved testing the specificity of each hybridoma to hepcidin-25. Briefly, 96 well EIA plates are coated overnight with goat anti-mouse IgG Fc-specific antibody (1/2,500 dilution), and the following day the plate was washed, blocked and 100 μl of tissue culture supernatant was placed in each well and incubated for 1 hour at room temperature. The ability of the murine antibodies present in the tissue culture supernatant that were captured by the Fc region was tested by addition of 1 ng of K18-Biotin Hepcidin-25 tracer to each well and incubating for 1.5 hours on a rotary plate shaker. After washing, HRP labeled streptavidin (SA-HRP) was added to the wells, incubated for one hour, washed and the presence of antibody-captured tracer was detected by the addition of TMB substrate for 10 min. The reaction was halted by the addition of acid and absorbance read at 450 nM. As depicted in FIG. 3, hybridomas that produce an OD>0.4 were identified and subcloned for further characterization. Our experience has proven that hybridomas that produce an OD that exceeds 2.0 in this second round of screening are strong candidates for further characterization.

To test for functional activity of the hybridomas, clones identified in the second round screen were subcloned, grown to approximately 70% confluency and screened as described for the second round screen. Briefly 96-well plates are coated with goat anti-mouse IgG Fc-specific antibody and the following day the plates were washed and blocked and tissue culture supernatant was placed in each well and incubated for 1 hour.

To prepare a stock solution of hepcidin, weigh out approximately 1 mg of lyophilized Hepcidin and reconstitute in 0.5 ml of 0.016% HCl (prepared in sterile tissue culture grade water) to make a final concentration of 2 mg/ml.

To accurately determine hepcidin concentration in the solution, measure the absorbance at 215 nm and 225 nm on a spectrophotometer.

For sample measurement, make a 1:20 dilution of the solution (10 μl of the stock solution to 190 μl of sterile water). Blank the spectrophotometer with 10% of 0.016% HCl. (10 μl of the 0.016% HCl to 190 μl of sterile water). Measure the absorbance at 215 nm and 225 nm and calculate the hepcidin concentration using the following formula for peptide concentration:

The calculation for hepcidin-25 concentration in mg/ml is [hepcidin-25 mg/ml]=(A215-A225)×0.144×20 (20 is the dilution factor).

To store hepcidin-25 stock solutions aliquot the solution in 100 μl volumes into a sterile 0.5 ml microcentrifuge tubes and store at −80° C. To further dilute the hepcidin stock to a convenient working solution, dilute the concentrated stock to 500 μg/ml (working solution) with sterile tissue culture grade water.

To confirm peptide concentration in the prepared solution, measure the absorbance at 215 nm and 225 nm. For the measurement, make a 1:10 dilution of the solution. Aliquot in 25 μl volumes in 0.5 ml sterile microcentrifuge tubes with the screw cap.

The ability of synthetic human hepcidin-25 to compete against the K18-Biotin Hepcidin-25 tracer for MAb binding sites was tested by the addition of 100 ng of hepcidin-25 prepared as above to the tracer solution and 100 μl of this was added to each well and incubated for 1.5 h. After washing, HRP labeled streptavidin was added, incubated for one hour, washed and the presence of bound tracer was detected by the addition of TMB substrate. The reaction was halted by the addition of acid and absorbance read at 450 nM. An example of functional activity screening of hybridoma supernatants is shown in FIG. 4. Hybridomas that display functional activity were identified by a reduction in the OD in the Tracer+Hepcidin-25 wells, compared to the OD produced by the Tracer only (for example hybridoma 5A3; 5A3 designation was later changed to "MAb 583").

An example of the difficulty of producing murine MAbs is shown in FIG. 5. A variety of typical antigens and immunization approaches can yield varying numbers of mice that respond to immunization (based on serum titers), and the tissues that yield successful fusions. Regardless of the antigen employed, the percentage of functional hepcidin-25 specific murine MAbs is consistently less than 0.06% (FIG. 5). Similarly, as an example of the effort required for discovery of 3 murine MAbs specific for hepcidin-25, we tested eight antigens and screened 11,845 hybridomas with a success rate of 0.025% (FIG. 6).

Example 4: Purification of Murine MAbs

Large quantities of MAb 583 and MAb 1B1 were produced by seeding individual commercially available Cell-Max hollow fiber bioreactors (10,000 $cm^2$ surface area (Spectrum Labs, Inc.) that were then incubated at 37° C. in a 5% $CO_2$ atmosphere. Approximately 2-3 liters of total cell culture supernatant from each MAb was harvested in approximately 100 ml batches. Each batch was centrifuged and frozen at −20° C. until purification.

For purification, the supernatant was thawed, re-centrifuged and immunoglobulin was purified by affinity chromatography using a 5 ml HiTrap protein G column (GE Healthcare, Uppsala, Sweden) as per manufacturer's instructions. Purification was performed using a BioRad Biologic DuoFlow medium pressure chromatography system equipped with a BioLogic Maximizer, QuadTec UV-VIS detector and a BioFrac fraction collector. For SDS-PAGE analysis. Flow through fractions from two previous purifications of MAb 583 and MAb 1B1 containing immunoglobulin were pooled and buffer exchange was performed using a HiPrep 26/10 desalting column (GE Healthcare). Protein concentration was determined using bicinchoninic acid (BCA, Thermo Scientific) and aliquots were stored frozen at −20° C.

An example of the purification of MAb 581 and MAb 1B1 (lot 3) was confirmed using Coomassie stained SDS-PAGE gels (12% acrylamide) run under standard reducing conditions (FIG. 7). As depicted in FIG. 7, purified preparations of MAbs 583 and 1B1 IgG (lanes 8, 9) were obtained from their respective hybridoma culture supernatants (lanes 2-5) as evidenced by the presence of both heavy and light chain proteins of the correct molecular mass (approximately 50 and 25 kDa, respectively). In addition, the purified murine MAbs were electrophoretically equivalent to the mouse IgG control (lane 10). Serum free tissue culture medium (lane 6) served as a negative control. This method would consistently yield a purified MAb that was suitable for further binding affinity (e.g. Biacore) and specificity studies.

To assess consistency of bioreactor production and purification yield a MAb activity characterization method was developed to assess the binding activity each successive purification Lot of MAb 583 antibody that were each assessed by gel electrophoresis as shown in FIG. 7. This same method was applied to purifications of MAb 1B1 (data not shown).

We used a microwell plate ELISA to assess antibody activity. Serial dilutions of purified MAb 583 from each successive purification Lot from bioreactor supernatants (approx. 100 ml per Lot) were coated on plates (0-100 ng) and blocked. The NT-biotin hepcidin-25 tracer was added across the plate at 1 ng/well in TBST, pH 8 containing 0.25% Blotto. The tracer was allowed to bind for 2 hours and the wells were washed in TBST, pH 8 with no Blotto. SA-HRP was added at 1:2500 for 30 minutes, the wells washed in TBST, and TMB substrate added for 10 minutes. Stop buffer was added the OD quantified on a spectrophotometer at 450 nm. An OD of 4 indicates the absorbance is beyond the analytic range of the spectrophotmer.

The table below is an example of the established ELISA method to determine binding activity characteristics for 5 successive MAb 583 purifications.

| 583 (ng/well) | Lot 3 583 #3 | Lot 4 583 #4 | Lot 5 583 #5 | Lot 6 583 #6 | Lot 7 583 #7 |
|---|---|---|---|---|---|
| 100 ng/well | 4 | 4 | 4 | 4 | 4 |
| 50 ng/well | 4 | 4 | 4 | 4 | 4 |
| 25 ng/well | 4 | 4 | 4 | 4 | 4 |
| 12.5 ng/well | 4 | 4 | 4 | 4 | 4 |
| 6.25 ng/well | 2.1401 | 3.2808 | 2.7839 | 4 | 3.3373 |
| 3.12 ng/well | 1.0645 | 1.8302 | 1.5279 | 2.3104 | 2.1237 |
| 1.56 ng/well | 0.5974 | 1.1527 | 0.9335 | 1.4203 | 1.3805 |
| 0 ng/well | 0.0446 | 0.0257 | 0.0232 | 0.0303 | 0.0642 |

The data show that the binding activity of purified MAb 583 across lots increased after Lot 3 and was consistent across Lots 4-7 after the purification protocol was optimized over the first four purifications performed. Wells coated with 6.25 ng purified MAb 583 demonstrated that optical density at 450 nm ranged from 2.7-4 across Lots 4-7 and at the next dilution (3.12 ng/well) the ODs ranged from 1.5-2.3. This example demonstrates that an established and validated protocol for purification of the MAb 583 antibody from bioreactor supernatants is established and shown to be consistent over dozens of purification Lots of both MAb 583 and 1B1.

Figure 8:
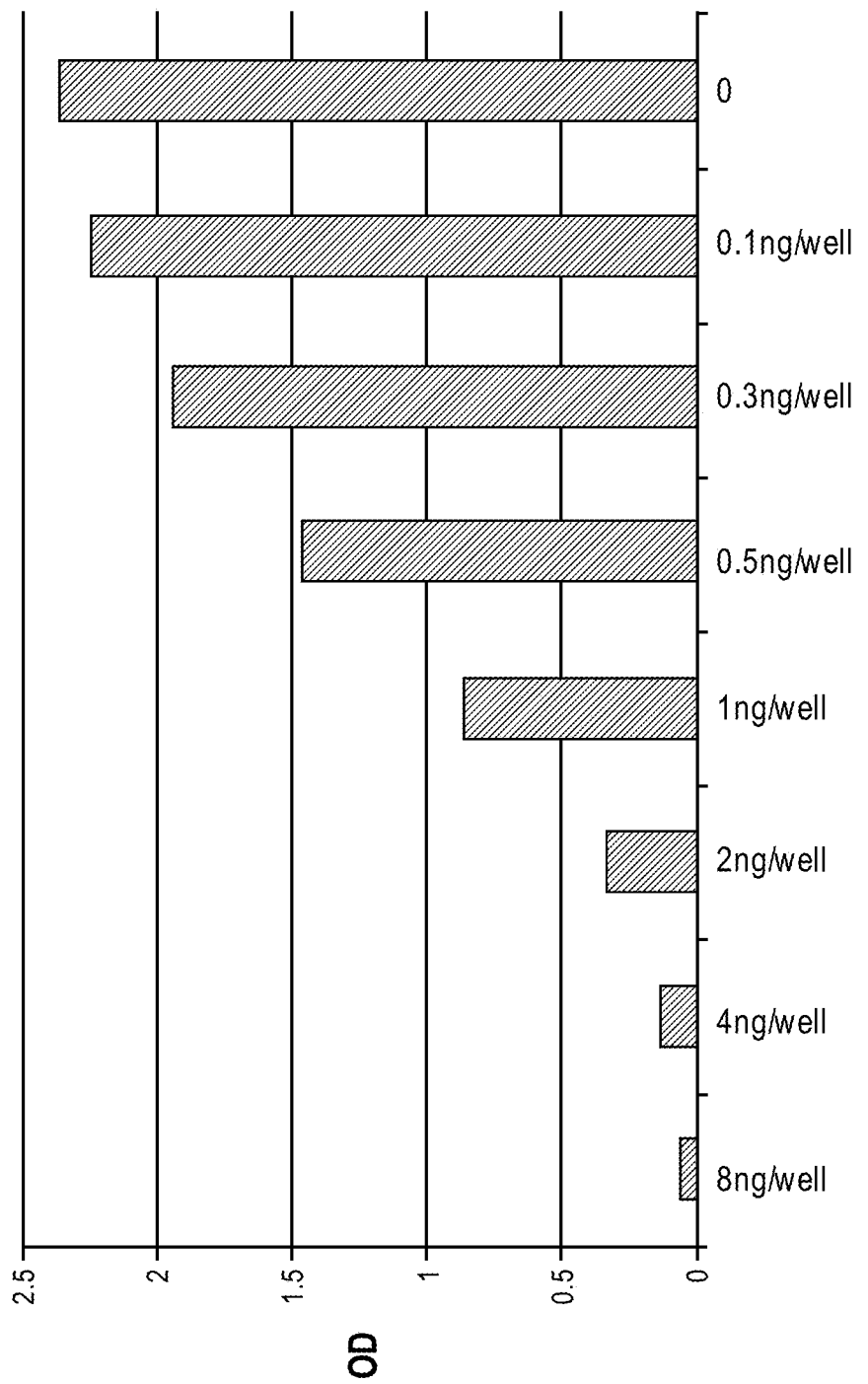
FIG. 8. ELISA analysis of neutralization of MAb 583 in solution by hepcidin-25. This solution-based screen tested the ability of 0.0, and 0.1-8.0 ng synthetic hepcidin-25 (x axis) to block (neutralize) the binding of 20 ng MAb 583 in solution. Synthetic hepcidin (0.1-8.0 ng) was added to 20 ng MAb 583 for two hours in binding buffer. The hepcidin-25 treated MAb 583 solutions were added to duplicate wells with hepcidin-25 (200 ng/well) covalently bound to maleic anhydride activated microwell plates. Binding to hepcidin-25 by MAb 583 was detected using rabbit anti-mouse IgG (H+L) conjugated to HRP with TMB as the substrate. MAb 583 binding to bound hepcidin-25 is quantified by spectrophotometry after addition of stop solution by measuring OD (optical density) at 450 nm.

Example 5: Characterization of MAb Specificity to Hepcidin-25 and Hepcidin Peptides MAb 583 demonstrates exquisite and excellent specificity for hepcidin-25 in a solution based specificity assay. For example, hepcidin-25 was coated on a maleic anhydride plate and unoccupied binding sites were quenched using standard methods. In parallel, 20 ng of MAb 583 is mixed with increasing concentrations of hepcidin-25 (0 to 8 ng/well) in a low protein binding 96-well plate and allowed to react for one hour. This MAb mixture is then transferred to the maleic anhydride plate and allowed to react for 2 hours, after which it is washed and the presence of MAb 583 bound to hepcidin-25 covalently bound to the plate is determined using HRP-goat anti-mouse IgG secondary antibody. After additional incubation and washing the substrate is added, development halted using acid and the OD 450 nM is determined. FIG. 8 demonstrates that hepcidin-25 can block the binding sites on MAb 583 in solution in a dose dependent manner.

Figure 9:
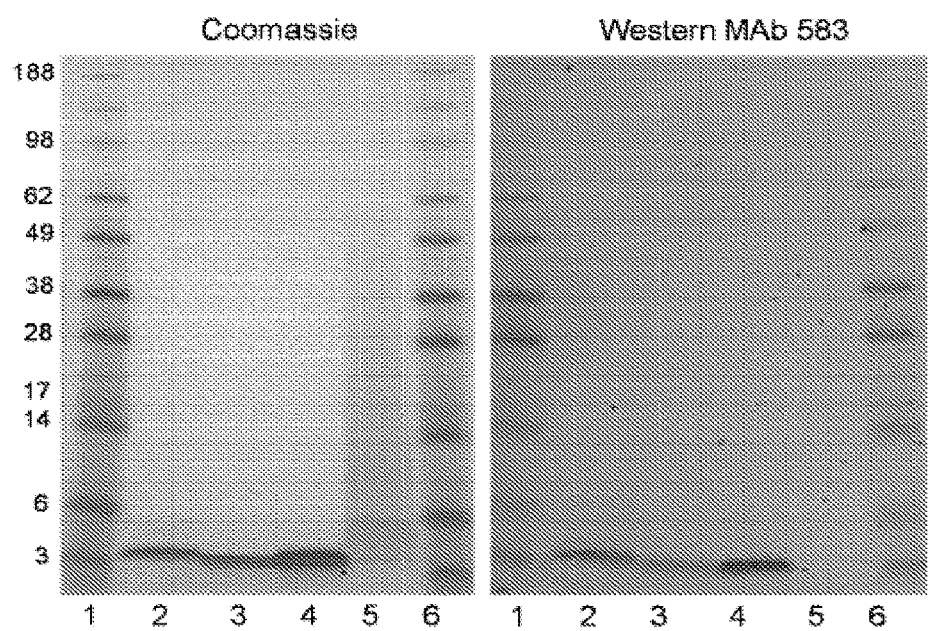
FIG. 9. Non-reducing tricine SDS-PAGE gel (left panel) stained with Coomassie and Western blot (right panel) of hepcidin-25, hepcidin-22, hepcidin-20, and protegrin (1.5 µg/lane) probed with MAb 583. Lane descriptions are provided in the legend below the blot.

Another example of the specificity of MAb 583 for hepcidin-20, hepcidin-22 and hepcidin-25 and protegrin was demonstrated using membrane based assays such as, but not limited to, non-reducing tricine SDS-PAGE (10-20% acrylamide) analysis using standard electrophoresis and immunoblot conditions (FIG. 9). As depicted in the Coomassie stained image, hepcidin-20, -22 and -25 (lane 2, 3, 4) and protegrin (lane 5) all have a similar molecular mass of approx. 3 kDa. In contrast, the Western blot probed with MAb 583 indicated that MAb 583 specifically recognized hepcidin-20, hepcidin-22 and hepcidin-25 but did not recognize protegrin.

Figure 10:
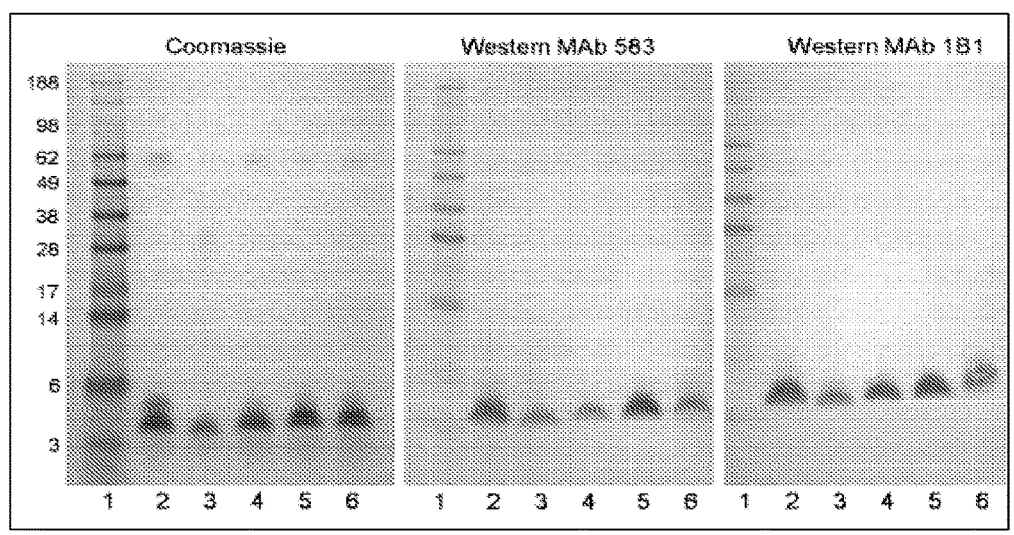
FIG. 10. Coomassie stained reducing SDS-PAGE and Western blots of binding activity of MAb 583 and MAb 1B1 against hepcidin-25, hepcidin-20, K18-biotin hepcidin-25, K24-biotin hepcidin-25, and NT-biotin hepcidin-25. Lane descriptions are provided in the legend below the blot.

To further exemplify the specificity of MAb 583 and MAb 1B1 for hepcidin-22 and hepcidin-25 and NT-biotin hepcidin-25 tracer, K18-biotin hepcidin-25 tracer and K24-biotin hepcidin-25 tracer, reducing SDS-PAGE (12% acrylamide) analysis and Western immunoblots were performed under standard electrophoresis and immunoblotting methods (FIG. 10). Coomassie stained SDS-PAGE analysis indicates that both hepcidin-20 and hepcidin-25 (lane 2, 3) and the three forms of biotin-labeled tracer (lane 4, 5, 6) have an identical molecular mass. Western blots probed with either MAb 583 or MAb 1B1 indicated that these MAbs specifically recognized the hepcidin-20, hepcidin-25 and the three forms of biotin-labeled hepcidin-25 tracer peptides. Taken collectively, our solution-based and membrane based studies demonstrate that MAb 583 and MAb 1B1 possess unique specificity for all three forms of the biotinylated human hepcidin-25 tracer molecules.

Example 6: BIAcore Surface Plasmon Resonance (SPR) Analysis of MAbs 583 and 1B1

This example describes the analysis of the binding affinity and dissociation constants of MAbs 583 and 1B1 interaction with hepcidin-25 using SPR.

SPR was performed on a Biacore 3000 System (BIAcore, Piscataway, N.J.) using CMS sensor chip. CMS chip matrix consists of a carboxymethylated dextran covalently attached to a gold surface. All measurements were performed at 25° C.

Neutravidin (Sigma, St. Louis, Mo.) was immobilized on a CMS sensor chip (flow cells 1 to 4) by the amine-coupling protocol, at a level of 5000-10000 response units (RUs). The amine coupling protocol includes activation of the dextran matrix on the sensor chip surface with a 1:1 mixture of 0.4 M 1-ethyl-3-(3-dimethylaminopropyl carbodiimide (EDC) and 0.1 M N-hydroxysuccinimide (NETS), followed by injection of neutravidin in 10 mM sodium acetate buffer, pH 4.

After neutravidin immobilization, the subsequent steps were carried out in HBS-EP buffer (10 mM HEPES, pH 7.4, 150 mM NaCl mM EDTA, and 0.005% surfactant P20).

Biotinylated hepcidin peptides (NT-biotin-hepcidin-25, K18-biotin-hepcidin-25 and K24-biotin-hepcidin-25) were immobilized in flow cells 2-4 (one peptide species per flow cell) by injecting individual peptides at a concentration of 200 µg/ml at a flow rate of 5 µl/min, for 20 min.

After biotin-hepcidin-25 analogs were captured on the chip, anti-hepcidin MAb 583 or 1B1 was injected into flow cells 1-4 at the concentration of 24 µg/ml in HBS-EP buffer at the flow rate of 50 µl/min, for 3 min. After 3 minutes, injection was stopped and dissociation was followed for 6 min. Regeneration was performed by injecting 10 mM glycine HCl pH 1.5 at a flow rate of 10 µl/min for 1 min.

Resonance signals were corrected for nonspecific binding by subtracting the signal of the control flow cell (cell 1) and analyzed using BIAevaluation 4.1 software (Biacore).

Figure 11:
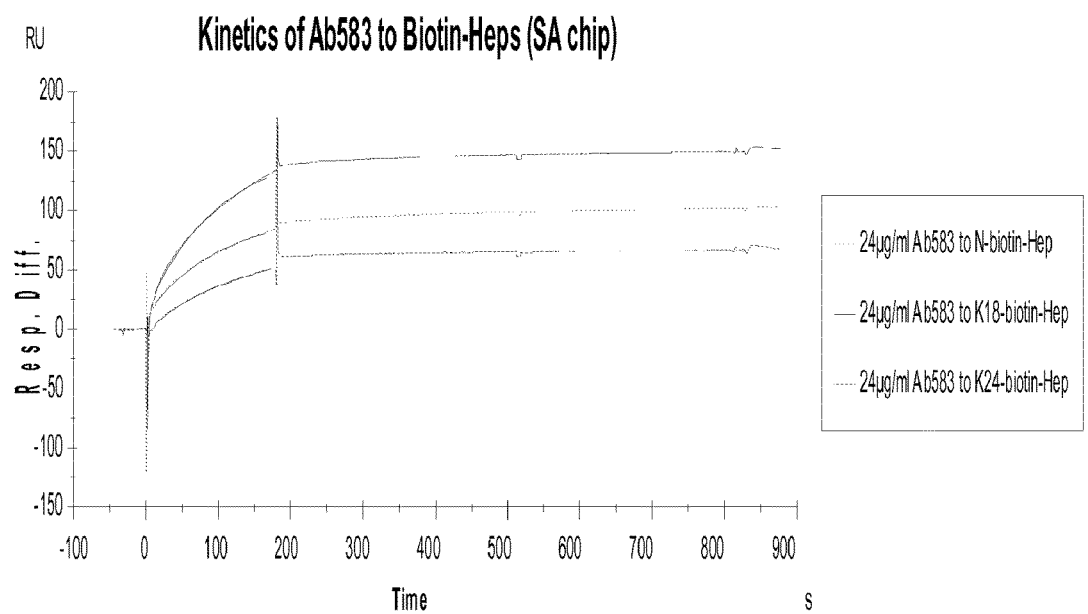
FIG. 11. Biacore analysis of binding affinities of MAb 583 at 24 µg/ml, for K18-biotin hepcidin-25, NT-biotin hepcidin-25, and K24-biotin hepcidin-25 bound to a streptavidin coated Biacore chip. The data show high affinity and picomolar dissociation constants for MAb 583 for NT-biotin hepcidin-25, and approximately one log decreased affinity constants for K18-biotin hepcidin-25 and K24-biotin hepcidin-25, respectively.

In the first SPR experiment, MAb 583 was applied to theBiacore chip prepared as described above at a concentration of 24 µg/ml and rapid binding and very low rate of dissociation of MAb 583 to the three biotin-hepcidin-25 analogs was observed (FIG. 11). The data from the SPR experiments shown in FIG. 11 are shown in the table below. Excellent binding affinity (Ka) and dissociation constants (Kd) were observed for MAb 583 with the NT-biotin hepcidin-25, and approximately 1 log lower affinity and dissociation constants for K18-biotin hepcidin-25 and K24-biotin hepcidin-25, respectively.

| | ka (1/Ms) | kd (1/s) | Rmax (RU) | RI (RU) | Conc of analyte | KA (1/M) | KD (M) | Req (RU) | kobs (1/s) |
|---|---|---|---|---|---|---|---|---|---|
| 24 µg/ml Ab583 to NT-biotin-hepcidin-25 | 6.11e4 | 3.15e−6 | 78.8 | 18.7 | 160n | 1.94e10 | 5.16e−11 | 78.8 | 9.77e−3 |
| 24 µg/ml Ab583 to K18-biotin-hepcidin-25 | 6.37e4 | 5.59e−5 | 127 | 25.9 | 160n | 1.14e9 | 8.78e−10 | 126 | 0.0102 |
| 24 µg/ml Ab583 to K24-biotin-hepcidin-25 | 5.2e4 | 2.88e−4 | 65.3 | 2.11 | 160n | 1.8e8 | 5.54e−9 | 63.1 | 8.6e−3 |

Figure 12:
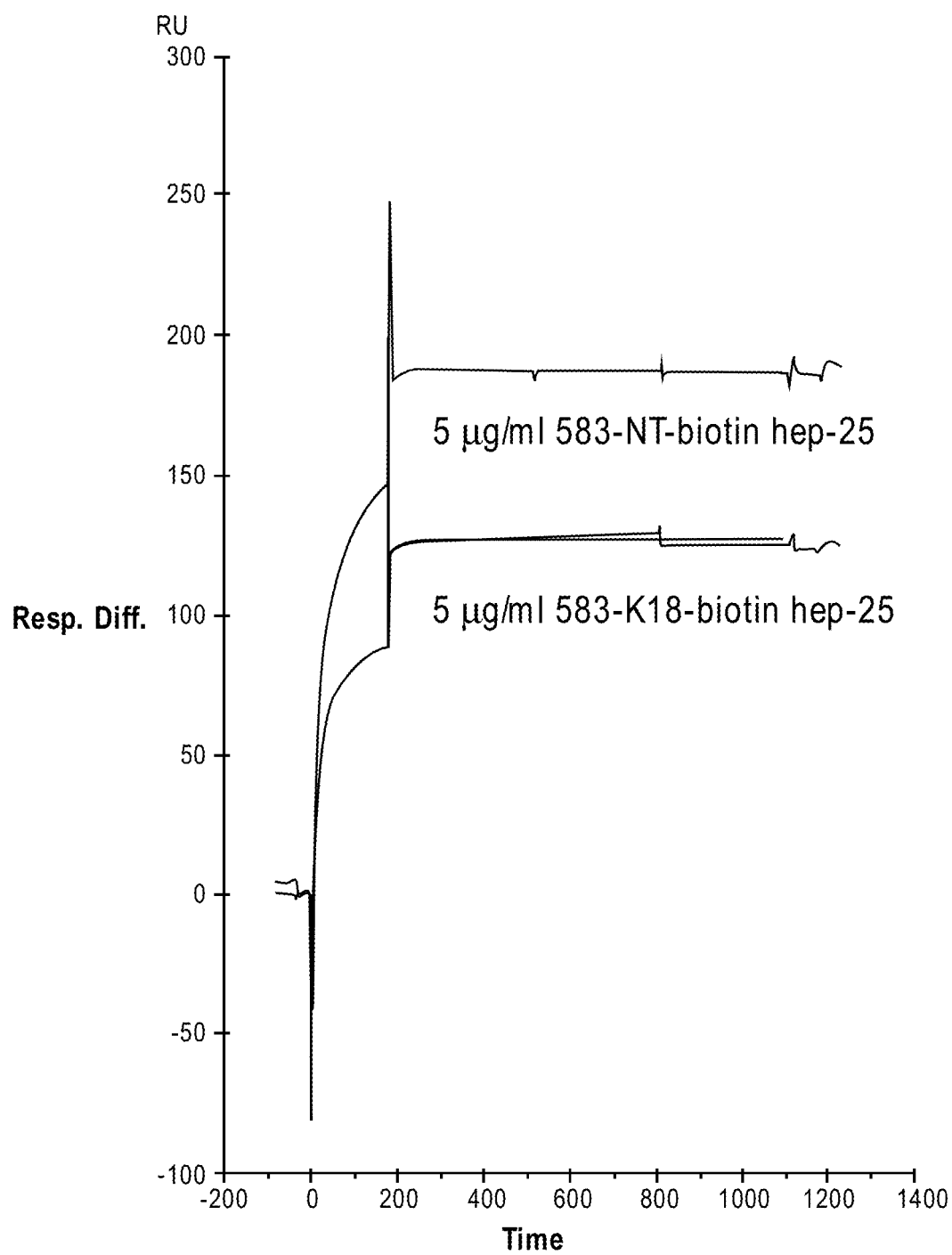
FIG. 12. Biacore analysis of binding affinities of MAb 583 at 5 µg/ml for K18-biotin hepcidin-25 and NT-biotin hepcidin-25 bound to a streptavidin coated Biacore chip. There is little change in the slope of the Biacore trace over 1200 seconds (20 minutes) indicating a low binding dissociation constants for MAb 583 for K18-biotin hepcidin-25 and NT-biotin hepcidin-25.

We repeated the Biacore experiment shown in FIG. 11 with an approximately 5-fold lower MAb 583 concentration (5 µg/ml) to assess MAb 583 at a much lower molar ratio of antibody for the two best biotinylated hepcidin-25 antigens, NT-biotin hepcidin-25 and K18-biotin hepcidin-25 (FIG. 12). The Biacore plot shows MAb583 has excellent binding affinity and very low disassociation from both K18-biotin hepcidin-25 and NT-biotin hepcidin-25 peptides assessed in this Biacore experiment. Biacore results from FIG. 12 are shown in FIG. 13.

The Biacore data indicate that MAb 583 binds to K18-biotin hepcidin-25 with high affinity and a low picomolar dissociation constant (Kd)=approx. 7.5 pM). MAb 583 has high but slightly lower binding affinity and low picomolar dissociation constants for NT-biotin-hepcidin-25, with a Kd=approx. 18 pM.

Figure 14:
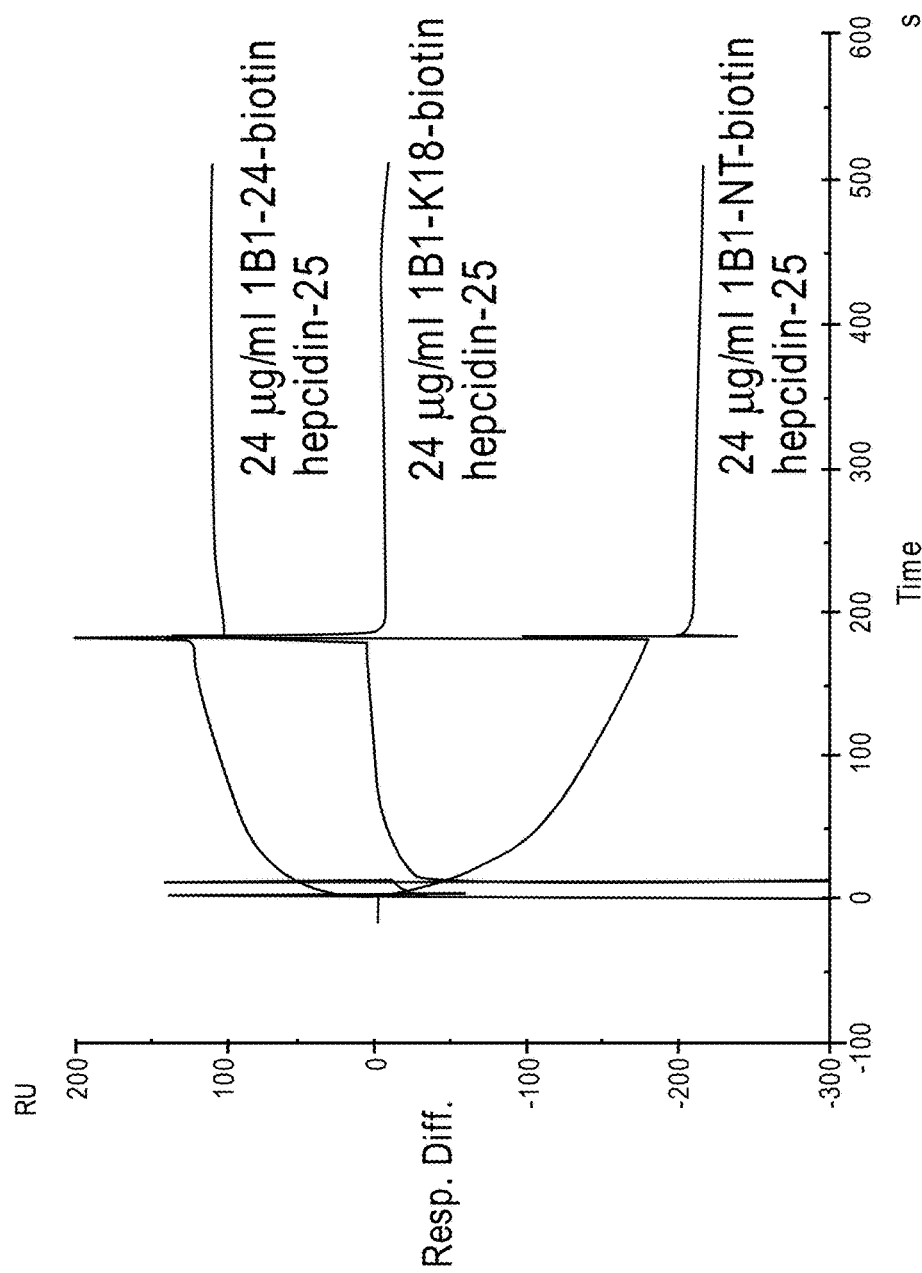
FIG. 14. Biacore data showing the binding affinity of MAb 1B1 at 24 µg/ml for K18-biotin hepcidin-25, NT-biotin hepcidin-25, and K24-biotin hepcidin-25. These data show MAb 1B1 has strong binding affinity for K24-biotin hepcidin-25, lower affinity for K18-biotin hepcidin-25, and no affinity for NT-biotin hepcidin-25. This experiment was conducted for 500 seconds and a no dissociation of 1B1 was observed or calculable by the Biacore instrument after binding to K24-biotin hepcidin-25 and K18-biotin hepcidin-25 over 500 seconds.
Figure 15:
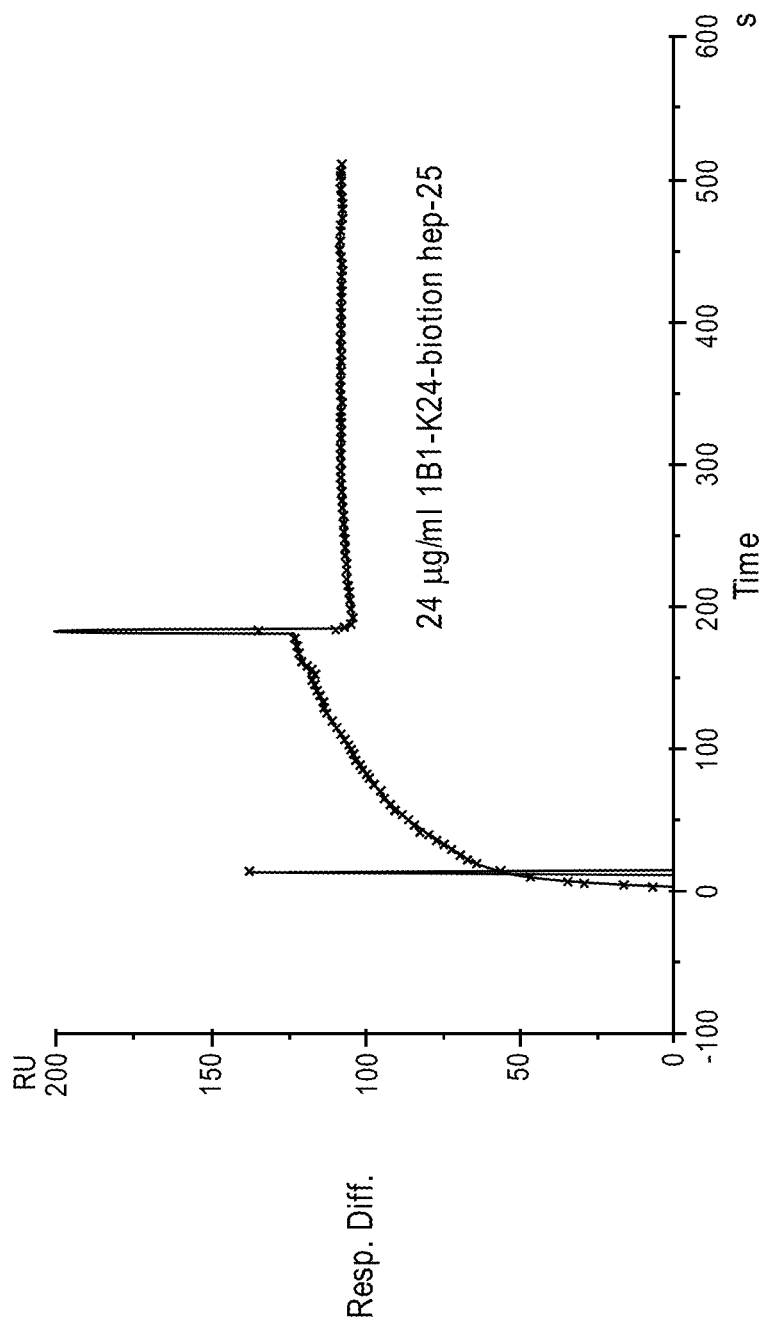
FIG. 15. Biacore data showing binding affinity of MAb 1B1 at 24 µg/ml for K24-biotin hepcidin-25. These data show strong affinity of 1B1 for K24-biotin hepcidin-25 and no dissociation of MAb 1B1 from K24-biotin hepcidin-25 over 500 seconds suggesting a low picomolar to femtamolar dissociation constant for 1B1 for hepcidin-25 is possible.

These Biacore experiments and results confirm that MAb 583 binds hepcidin-25 rapidly and with high affinity and dissociates from hepcidin-25 slowly with low pM dissociation constants. The epitope for MAb 583 is the N-terminal 9 amino acids of which the first 5 N-terminal amino acids (SEQ 25) are essential for hepcidin-25 binding to the iron transporter and receptor, ferroportin, and its ability to internalize and degrade ferroportin The excellent specificity, affinity, avidity, and pM Kd of MAb 583 for the N-terminus of hepcidin-25 indicates that it will be a neutralizing antibody in vitro and in vivo, and suitable for humanization for therapeutic applications. Examples of Biacore experiments with MAb 1B1 are shown in FIGS. 14-15. Two attempts were made using the same conditions as described for MAb 583 to conduct SPR analysis with MAb 1B1 in and each case the dissociation rate of 1B1 from the hepcidin-25 antigens was so low that the Biacore 3000 instrument that the BIAevaluation 4.1 software used could not detect any dissociation of 1B1 from the hepcidin-25 antigens over the 20 minute experiment. For this reason, the experiments failed to produce statistical information as shown for MAb 583 in FIG. 13 for the Biacore experiments shown in FIGS. 14-15.

SPR analysis under these experimental conditions indicate that the murine MAb 1B1 has extraordinary affinity for hepcidin-25 peptides and may have an affinity constant ($K_D$) of $\leq 10^{-12}$-$10^{-13}$ M) and with these characteristics may be suitable for humanization and pre-clinical evaluation as a hepcidin-25 specific MAb.

Example 7: Hepcidin Specificity and Binding Experiments with MAbs 583 and 1B1

The specificity and relative binding affinities of the 583 and 1B1 were assessed in a series of microtiter plate competition experiments. Assays were performed in duplicate or triplicate using 96-well-microtiter plates coated with MAb 583 or MAb 1B1.

MAb 583 was diluted 1:4000 in Tris buffered saline (TBS) containing 40 mM Tris-HCl (pH 7.3), 100 mM NaCl, was pipetted into the microtiter plates.

After a 1 hour incubation at room temperature (RT), the microtiter plates were washed with TBST (TBS with 0.05% TWEEN® 20) and 100 ml standard samples containing various amounts of synthetic peptides and biotin hepcidin-25 analogs (1-2 ng/well) were added to each well and incubated for 1 hour at RT.

Competition was detected by streptavidin-HRP with the substrate tetramethylbenzidine; the color reaction was stopped with 0.5 N $H_2SO_4$ and the optical density of the solution read at 450 nm wavelength.

Figure 16:
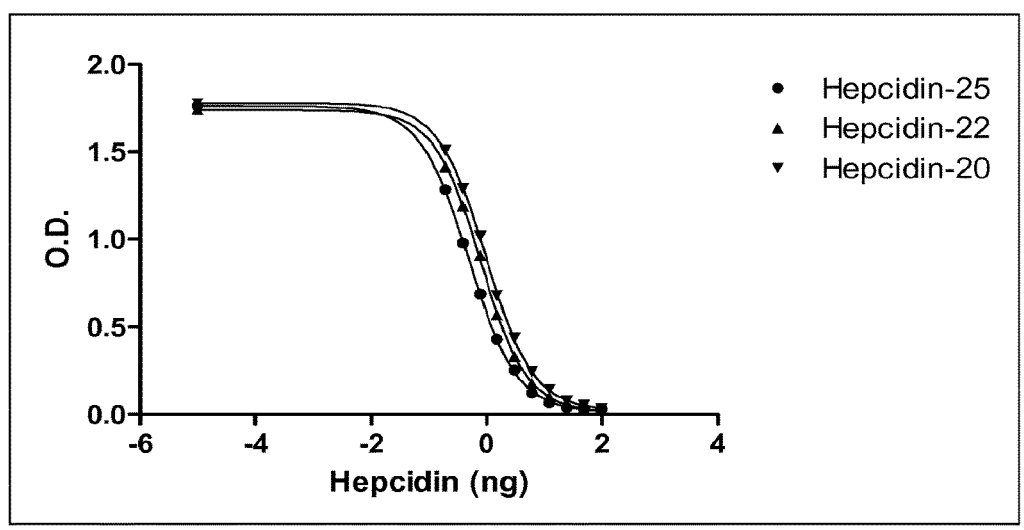
FIG. 16. ELISA standard curve analysis of binding of hepcidin-25, hepcidin-22, and hepcidin-20 to MAb 583 antibody coated at 100 ng/ml per well. The relative binding of the NT-biotin hepcidin-25 tracer (1 ng/well) relative to hepcidin-25, hepcidin-22, and hepcidin-20 was measured by ELISA. Four parameter logistical regression analysis was conducted using GraphPad Prism software to produce the curves shown. A right shift in the curve demonstrates consecutively lower affinity of MAb 583 for hepcidin-22 and hepcidin-20, than MAb 583 has for hepcidin-25.

Analysis of binding of hepcidin-25, hepcidin-22, and hepcidin-20 to MAb 583 antibodies coated on a microtiter plate. Binding of biotinylated hepcidin-25 analogs and detection of bound NT-biotin hepcidin-25 was used to detect relative degree of binding of each of the hepcidin peptides relative to hepcidin-25 (FIG. 16). Competition curves with the NT-biotin hepcidin-25 with the hepcidin peptide isomers, hepcidin-22 and hepcidin-20, were similar indicating that the hepcidin isomers do bind to MAb 583, but with decreasing EC50 values (affinity) with decreasing size of the hepcidin isomer as demonstrated by the right shift in the regression curve going from hepcidin-25 to hepcidin-22 to hepcidin-20.

We used the same method as above to investigate the relative binding affinities of MAbs 583 and 1B1 against a C-terminal, oxidized peptide, to assess the binding epitopes on hepcidin for each MAb. The carboxy terminal peptides such as hepcidin (10-25) are described in U.S. Pat. Nos. 7,320,894 and 7,411,048, each of which patents are incorporated herein by reference with respect to the peptides.

Figure 17:
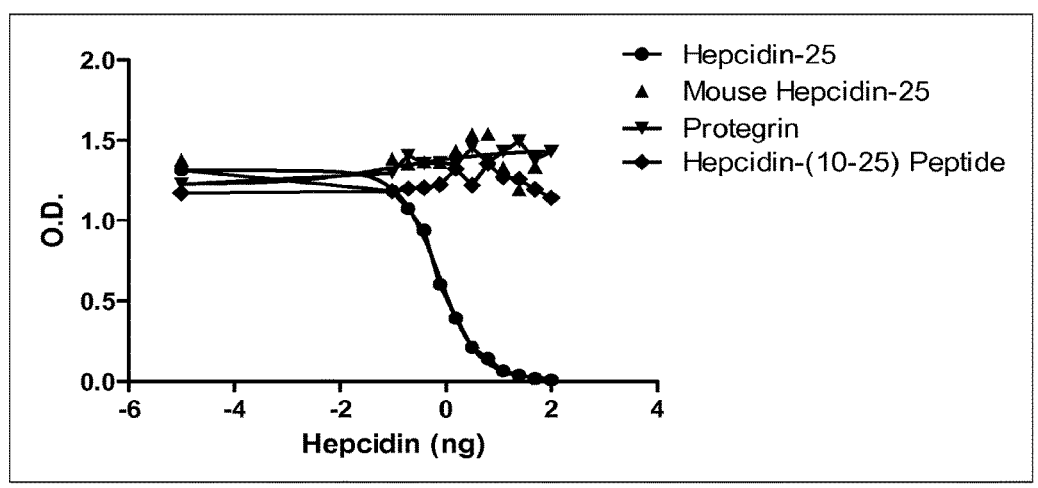
FIG. 17. ELISA analysis of binding to murine hepcidin-1 (mouse hepcidin-25), protegrin, and hepcidin-(10-25) peptide to MAb 583 compared to NT-biotin hepcidin-25. These data show that there is no binding of MAb 583 to murine hepcidin-1, protegrin, or an oxidized and refolded hepcidin-(10-25) peptide containing the proper cysteine bonds for this region of hepcidin-25 at concentrations up to 2000 ng/ml.
Figure 18:
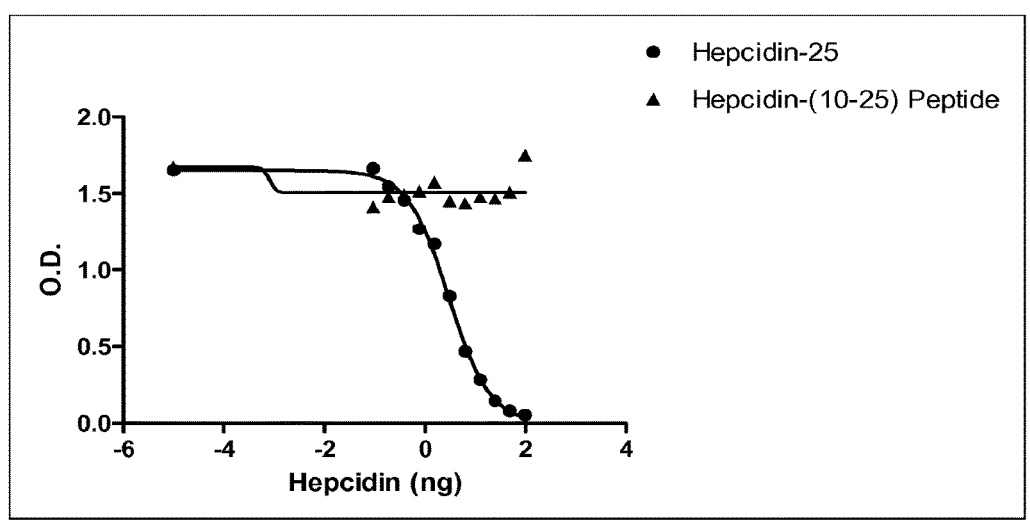
FIG. 18. ELISA analysis of binding of hepcidin-(10-25) peptide to MAb 1B1. The results indicate that MAb 1B1 has no binding affinity for an oxidized and refolded hepcidin-(10-25) peptide containing the proper cysteine bonds for this region when compared to hepcidin-25. K18-biotin hepcidin-25 was used for detection. Note that there is no binding of hepcidin-(10-25) peptide to MAb 1B1 at concentrations up to 2000 ng/ml.

As shown in FIG. 17 and FIG. 18, there was no binding of the hepcidin (10-25) peptide to either MAb 583 or 1B1, respectively, at any tested concentration up to 2000 ng/ml with either the NT-biotin hepcidin-25. There was also no binding observed between MAb 583 and mouse hepcidin-25 (murine hepcidin-1) or protegrin as compared to excellent competitive binding by synthetic hepcidin-25 in this ELISA experiment (FIG. 17). These experiments clearly show that MAbs 583 and 1B1 do not bind any epitopes found in the C-terminal 16 amino acids of hepcidin-25 (hepcidin (10-15) and thus bind N-terminal epitopes.

The cationic antimicrobial peptide, protegrin, and mouse hepcidin-25, (murine hepcidin-1) are structurally similar, with murine hepcidin-1 sharing 76% amino acid identity to human hepcidin-25. We used to the peptides to test cross-reactivity of MAb 583 with similar peptides in the same assay with MAb 583. As clearly shown in an ELISA experiment, we found no apparent binding of 583 to these structurally similar peptides (FIG. 17).

Figure 19:
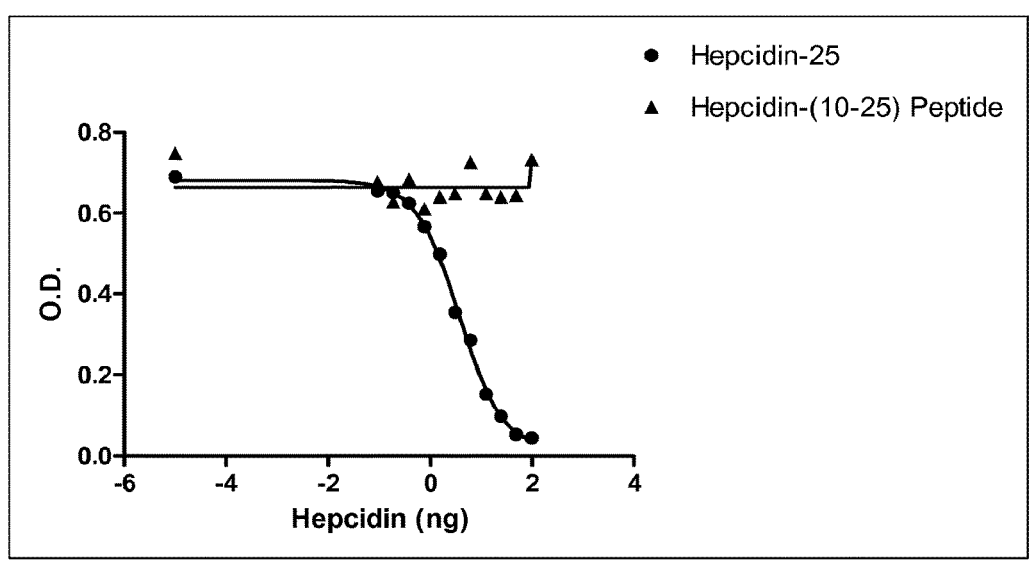
FIG. 19. ELISA analysis of binding of hepcidin-(10-25) to MAb 1B1. The results indicate that MAb 1B1 has no binding affinity for an oxidized and refolded hepcidin-(10-25) peptide containing the proper cysteine bonds for this region when compared to hepcidin-25. NT-biotin hepcidin-25 was used for detection. Note that there is no binding of hepcidin-(10-25) to MAb 1B1 at concentrations up to 2000 ng/ml of the hepcidin-(10-25) peptide.

In a similar experiment as shown in FIG. 18, we observed no binding of hepcidin (10-25) to MAb 1B1 in a similar experiment conducted with K18-biotin hepcidin-25 used as the tracer in the ELISA experiment (FIG. 19) further confirming the N-terminal 9 amino acids as the key epitope for 1B1. Importantly, these data show that both MAbs 583 and 1B1 have excellent affinity and specificity for the N-terminus of hepcidin-25. Both would be predicted to be neutralizing antibodies for hepcidin's bioactivity against the ferroportin receptor and iron channel in vitro and in vivo and once humanized, candidates for therapeutic development Example 8: Analysis of MAb 583 for Neutralizing Activity Against Hepcidin-25 In Vitro in Cell Based Assays by Ferroportin-GFP Fluorescence Analysis In Vitro Cell Based Assays We assessed the neutralizing activity of MAb 583 in vitro in a cell based fluorescence assay using the flow cytometry protocol as described in Nemeth et al. (2006) to assess the neutralizing activity of MAb 583 against human hepcidin-25 (SEQ ID NO. 19). The N-terminal five amino acids [SEQ ID NO. 25] of hepcidin interact with ferroportin and are required for the biological activity of hepcidin, whereby each single amino acid deletion from the N-terminus reduces hepcidin's biological activity as defined by ferroportin degradation activity (FIGS. 20-23).

Human HEK cells containing a ponasterone-inducible mouse ferroportin construct (Fpn-GFP) were incubated with or without 10 mM ponasterone for 24 hours. After three washes with 1×Dulbecco's PBS, the cells were treated sequentially with known quantities of Protein A affinity purified MAb 583 antibody and known concentrations of biologically active synthetic human hepcidin-25, or control buffer for another 24 hours.

Cells were detached using TrypLE Express (Invitrogen) and re-suspended in medium at a concentration of $1 \times 10^6$ cells/ml. The intensity of green fluorescence was measured using flow cytometry.

Cells not expressing Fpn-GFP (no ponasterone) were used to establish a gate (baseline) to exclude background fluorescence. The results were represented as a fraction of the GFP intensity of untreated cells, according to the formula (Fx-Fhep)/(Funtreated-Fhep), where F represents the mean of the gated green fluorescence.

Flow Cytometry of Fpn-GFP Cells Treated with MAb 583.

Figure 20:
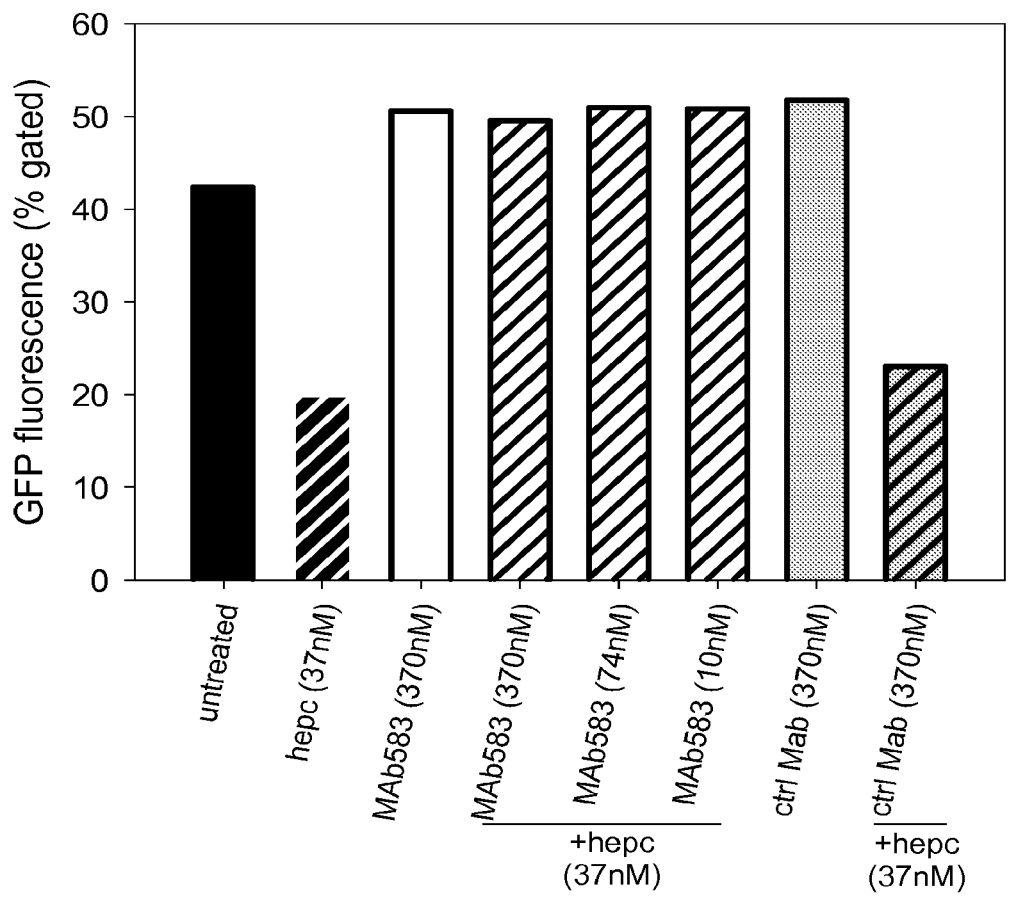
FIG. 20. Flow cytometry of Fpn-GFP cells treated with MAb 583. Cells were induced overnight with ponasterone to induce expression of murine Fpn-GFP. The next day, ponasterone was removed by washing, and hepcidin-25 and MAb 583 antibodies added for 24 hours. Hepcidin-25 was used at 100 ng/ml concentration (37 nM). MAb 583 was added at 10-times, 2-times or ⅓rd of hepcidin concentration (370 nM, 74 nM and 10 nM). The control MAb was a failed anti-hepcidin monoclonal antibody when screened in vitro by ELISA and was used at the highest concentration (370 nM). Note that 10 nM MAb 583 neutralized completely 37 nM hepcidin-25 and its biological activity leading to degradation of FPN-GFP.
Figure 21:
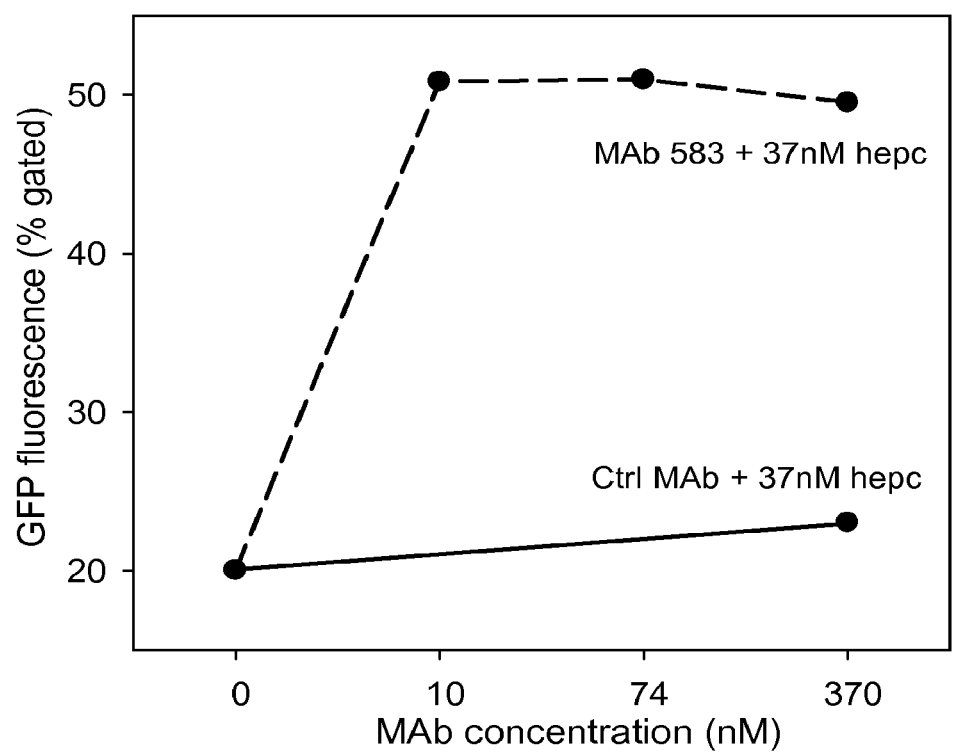
FIG. 21. Percent (%) change in FPN-GFP fluorescence in HEK cells treated with MAb 583 at concentrations from 10-370 nM in the presence of 37 nM hepcidin-25.

In the first experiment, cells were induced overnight with ponasterone to induce expression of murine Fpn-GFP. Next day, ponasterone was removed by washing, and hepcidin-25 and 583 antibodies added for 24 hours (FIG. 20 and FIG. 21).

Hepcidin-25 was used at 100 ng/ml concentration (37 nM). MAb 583 was added at 10-times, 2-times or ⅓rd relative molar concentration of hepcidin concentration (370 nM, 74 nM and 10 nM).

The control MAb was a failed anti-hepcidin monoclonal antibody when screened in vitro by ELISA and was used at the highest concentration (370 nM). In this experiment, 10 nM MAb 583 completely neutralized 37 nM hepcidin-25 and suppressed hepcidin-25 degradation of FPN-GFP.

Figure 22:
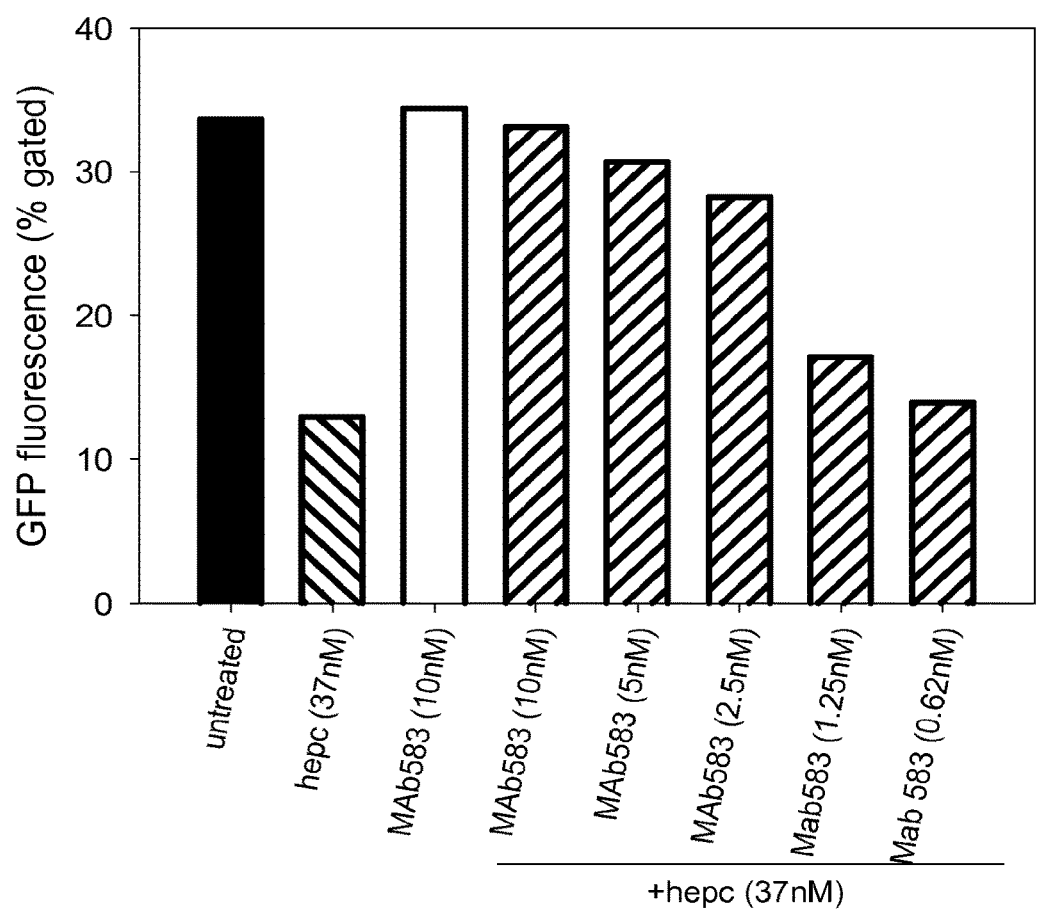
FIG. 22. Flow cytometry of Fpn-GFP cells treated with MAb 583. Cells were induced overnight with ponasterone to induce expression of murine Fpn-GFP. Next day, ponasterone was removed by washing, and hepcidin-25 and MAb 583 antibodies added for 24 hours. Hepcidin-25 was used at 100 ng/ml concentration (37 nM). MAb 583 was added at ⅓rd, ⅙th, ¹⁄₁₂th, and ¹⁄₂₄th the molar concentration of hepcidin-25 in these cell based assays of MAb 583 biological activity. The control MAb was a failed anti-hepcidin monoclonal antibody when screened in vitro by ELISA and was used at the highest concentration (370 nM). Note that 2.5 nM MAb 583 neutralized significantly (~23% decrease) 37 nM hepcidin-25 and it biological activity leading to degradation of FPN-GFP at $1/12^{th}$ of the molar ratio in vitro.
Figure 23:
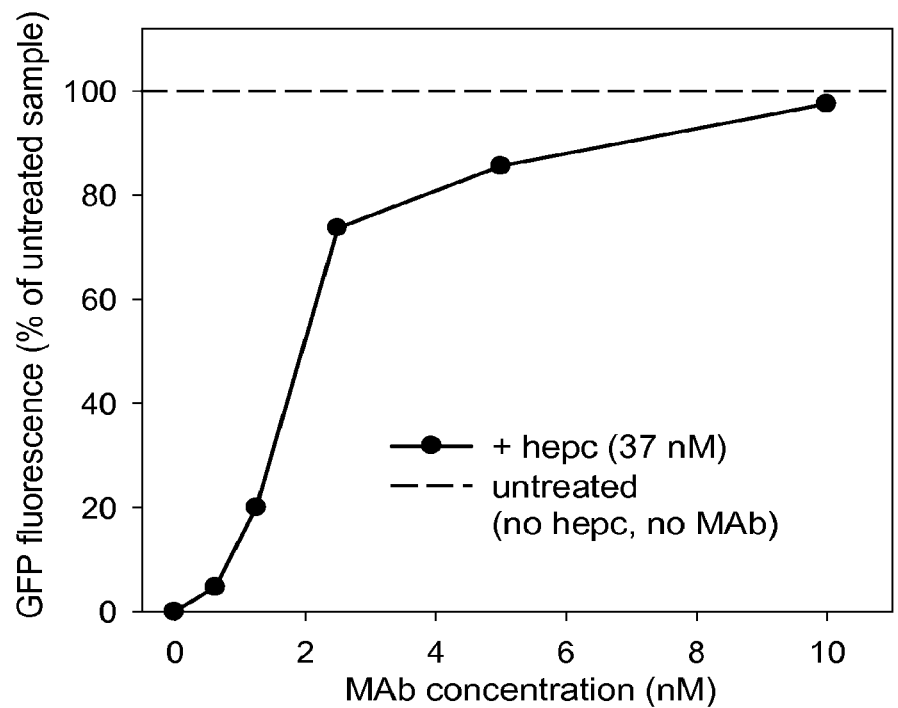
FIG. 23. Percent (%) change in FPN-GFP fluorescence in HEK cells treated with MAb 583 at concentrations from 0.62-10 nM in the presence of 37 nM hepcidin-25 as described in FIG. 22.

We repeated the experiment by with MAb 583 added at ⅓rd, ⅙th, 1/12th, and 1/24th the molar concentration of hepcidin-25 in these cell based assay of MAb 583 biological activity (FIG. 22 and FIG. 23).

In this experiment 2.5 nM of MAb 583 neutralized significantly (~23% decrease) 37 nM hepcidin-25 and it biological activity to FPN-GFP at 1/12$^{th}$ of the molar ratio of biologically active hepcidin-25 (FIG. 22, 23).

Figure 24:
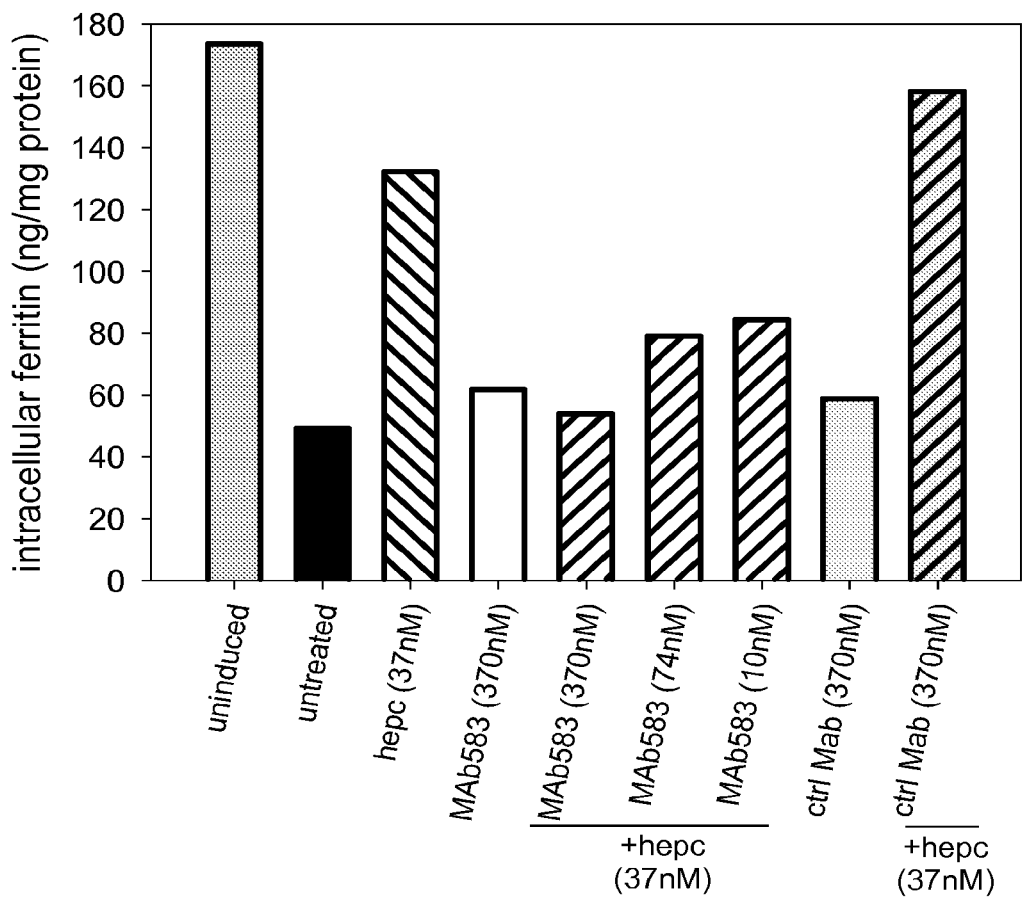
FIG. 24. Ferritin assay of Fpn-GFP cells treated with MAb 583. HEK cells were induced overnight with ponasterone to induce expression of murine Fpn-GFP and iron transport into the media. The next day, ponasterone was removed by washing, and hepcidin-25 and MAb 583 antibodies added for 24 hours. Hepcidin-25 was used at 100 ng/ml concentration (37 nM). MAb 583 was added at 10-times, 2-times or ⅓rd of hepcidin concentration (370 nM, 74 nM and 10 nM). The control MAb was a failed anti-hepcidin monoclonal antibody when screened in vitro by ELISA and was used at the highest concentration (370 nM). Note that 10 nM MAb 583 significantly neutralized 37 nM hepcidin-25 and it biological activity leading to degradation of FPN-GFP and retention of intracellular ferritin bound iron. Proteins were extracted using RIPA buffer and intracellular ferritin concentrations determined using ferritin ELISA (Ramco).
Figure 25:
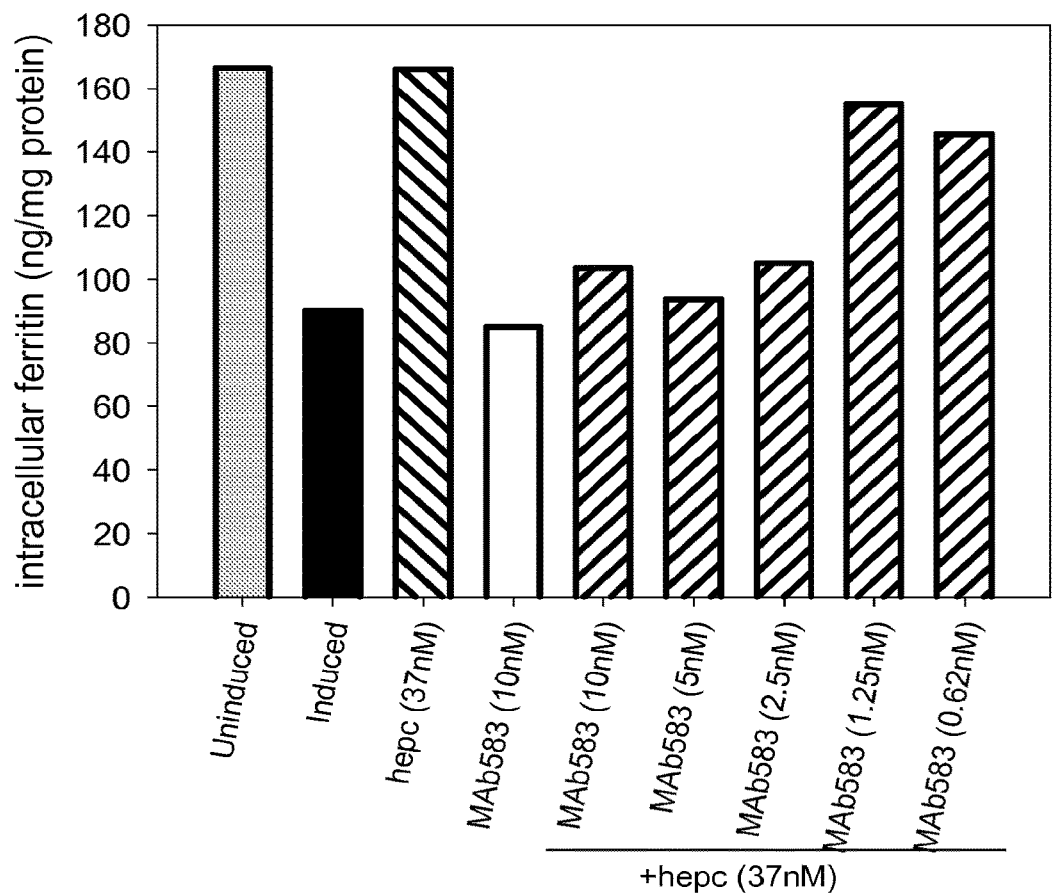
FIG. 25. Ferritin assay of Fpn-GFP cells treated with MAb 583. HEK cells were induced overnight with ponasterone to induce expression of murine Fpn-GFP and iron transport into the media. Next day, ponasterone was removed by washing, and hepcidin-25 and MAb 583 antibodies added for 24 hours. Hepcidin-25 was used at 100 ng/ml concentration (37 nM) and MAb 583 antibody at ⅓rd, ⅙th, ¹/₁₂th, and ¹/₂₄th the molar concentration of hepcidin-25 in these cell based assay of MAb 583 biological activity. The control MAb (sham MAb) was a failed anti-hepcidin monoclonal antibody when screened in vitro by ELISA and was used at the highest concentration (370 nM). Note that 2.5-5 nM 583 significantly neutralized 37 nM hepcidin-25 and it biological activity leading to degradation of FPN-GFP and retention of intracellular ferritin bound iron. Proteins were extracted using RIPA buffer and intracellular ferritin concentrations determined using ferritin ELISA (Ramco).
Figure 26:
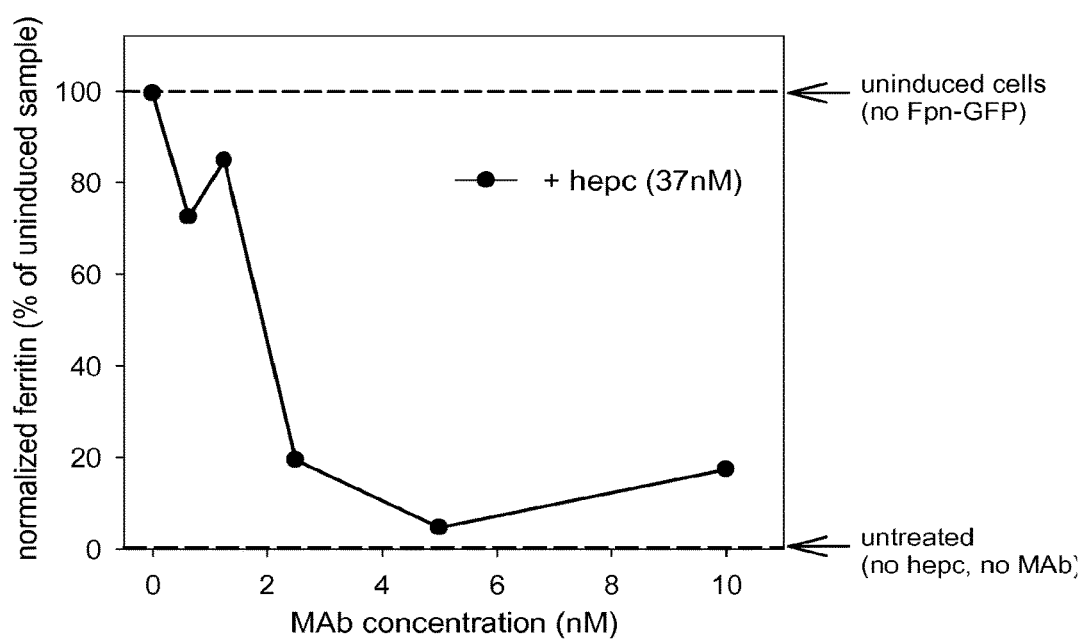
FIG. 26. Percent (%) change of intracellular ferritin concentration in HEK cells treated with MAb 583 at concentrations from 0.62-10 nM in the presence of 37 nM hepcidin-25 as described in FIG. 25.

We also assessed the neutralizing activity of MAb 583 by obtaining intracellular ferritin measurements from control Fpn-GFP cells and cells treated with varying concentrations of MAb 583 and hepcidin in two additional experiments using the identical protocols, including concentration of the MAb 583 antibody and hepcidin-25 biotinylated peptides, as in the cell based fluorescence assays (FIGS. 24-26).

To obtain intracellular ferritin concentrations, total cellular protein was extracted using RIPA buffer (Boston Bio-Products, Ashland, Mass.) with addition of a protease inhibitor cocktail according to the manufacturer's instructions (Roche, Indianapolis, Ind.).

Ferritin levels were determined using an enzyme-linked immunosorbent assay (ELISA; Ramco Laboratories, Stafford, Tex.) according to the manufacturer's instructions with normalized total protein concentrations in each sample. Total protein concentration was determined using the bicinchoninic acid (BCA) assay (Pierce, Rockford, Ill.).

FIGS. 24-26 show the results of these assays designed to assess the ability of MAb 583 to neutralize the biological activity of hepcidin-25 against ferroportin.

Similar to the results observed in fluorescence assays described herein, 2.5-10 nM MAb 583 significantly neutralized 37 nM hepcidin-25 and its biological activity in vitro, leading to decreased degradation of FPN-GFP and retention of intracellular ferritin bound iron (FIG. 24-26).

Example 9. In Vivo Neutralizing Activity of MAb 583 in C57BL/6 Mice

To assess the in vivo neutralizing characteristics of MAb 583, we performed a simple but robust animal study were we examined two dosing regimens with affinity purified MAb 583 antibodies for the 583 antibodies ability to block biologically active hepcidin-25 in vivo. We tested a single dose of MAb 583 and two 50% doses of MAb 583 applied sequentially 24 hours apart via intra peritoneal injection.

Figure 27:
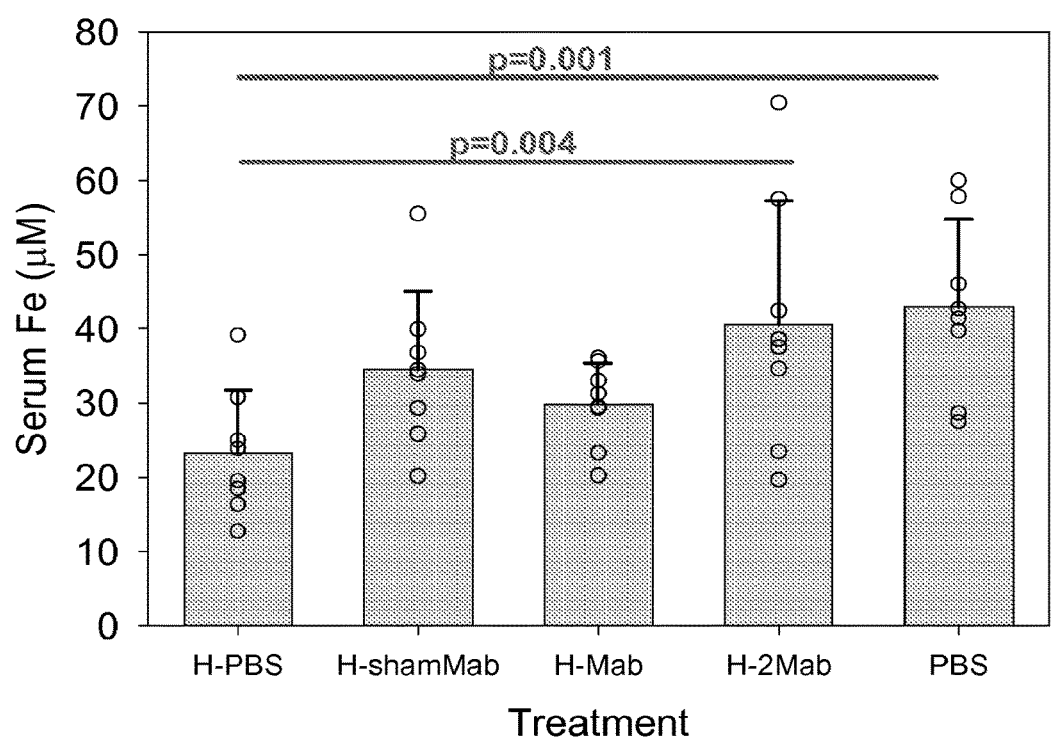
FIG. 27. Effect of injection of MAb 583 and human hepcidin-25 in vivo on serum iron concentration in male C57Bl/6 mice. Five groups of mice (n=8/group) were injected intraperitoneally with either PBS (group 1, H-PBS and group 5, PBS), 1 mg MAb 583 (group 2, H-Mab), 0.5 mg MAb 583 (group 3, H-2Mab), or 0.5 mg of control Mab (group 4, H-sham Mab). The following day all mice in group 3 received an additional 0.5 mg of MAb 583 and 24 hours later groups 1-4 received a single injection of 50 µg of human hepcidin-25 and group 5 received PBS. All mice were sacrificed 2 hours later and serum iron was measured. Statistical analysis (see FIG. 28 for details) indicated a significant difference between PBS and PBS plus hepcidin-25 (H-PBS, P=0.001), and between PBS plus hepcidin-25 (H-PBS) and mice that received two doses of 0.5 mg of MAb 583 and hepcidin-25 (H-2Mab, P=0.004).

To initiate the in vivo MAb 583 experiment, forty C57BL/6 male mice (6 weeks of age) were housed in a commercial vivarium within our building and fed a low iron diet (20 ppm total iron, Teklad Custom Research Diet, Harlan Laboratories) for 17 days. On day 1, forty mice were randomized into five experimental groups of 8 and each group was treated as described below. Group one received PBS only, groups 2 and 3 received 1.0 mg and 0.5 mg of MAb 583 respectively, group 4 received the control Mab (anti-hepcidin MAb unsuitable for ELISA) and group 5 received PBS. Twenty-four hours later each mouse in group 3 received an additional 0.5 mg of MAb 583. Following an additional 24 hour incubation period, groups 1 through 4 received 50 µg hepcidin-25 in PBS and mice in group 5 (control group) received their second dose of PBS (FIG. 27)

Mice were bled via cardiac puncture 2 hours after treatment, blood was allowed to clot for 30 min and their serum iron levels assessed using a commercial spectrophotometric method (Iron-SL Assay, Genzyme Diagnostics).

Statistical analysis of the data show the data was normally distributed by the Shapiro-Wilk Normality Test (P=0.216).

The Equal Variance Test of the data showed equivalent variances across the groups (P=0.360).

ANOVA was performed and indicated that there was a statistically significant difference (P=0.008) differences in the mean values of serum iron concentrations among the treatment groups (FIG. 28). FIG. 27 shows these results graphically and the significant differences between PBS controls and mice treated with either hepcidin-25 in PBS alone or in combination with two 0.5 mg doses of MAb 583 in PBS (FIG. 28).

Power of performed test with alpha=0.050:0.748.

Multiple Comparisons versus Control Group (Holm-Sidak method) yielded an overall significance level=0.05.

Significant differences were observed in plasma iron concentrations between the PBS control group and the group of mice administered either 50 µg hepcidin-25 in PBS or two 0.5 mg doses of MAb 583 over 24 hours. The group administered the 50 µg hepcidin-25 in PBS followed by 1.0 mg of the control anti-hepcidin MAb (sham MAb) approached a significant difference with the PBS plus hepcidin-25 control group (P=0.054; FIG. 28).

These results are promising and indicate that MAb 583 has neutralizing activity in vivo that suppress the biological activity of hepcidin-25 when both are injected sequentially IP in male C57BL/6 mice. The 50 µg dose of human hepcidin-25 used in this in vivo experiment has been previously shown to induce severe hypoferrimia for up to 72 hours in C57BL\6 mice and therefore the dose represents a stringent test of the neutralizing activity of MAb 583 (Rivera et al. 2005).

Example 10. Human-Mouse Chimeric Antibody

The light and heavy chain variable domains of murine anti-hepcidin MAB 583 were synthesized and cloned into a proprietary mammalian expression vector without any modifications. The light chain variable domain was cloned in-frame with a secretion signal and a human kappa light chain constant domain. The heavy chain variable domain was cloned in frame with a secretion signal and a human IgG1 constant domain. The resulting clone, BAP070-01, was sequence verified. Note that the signal sequence is underlined below.

BAP070-01-Light Chain DNA Sequence (SEQ ID NO: 37)
ATGGACATGAGGGTCCCCGCTCAGCTCCTGGGGCTCCTGCTGCTCTGGCT

CCCAGGTGCCAAGTGTGACATTGTGCTGACCCAATCTCCAGCTTCTTTGG

CTGTGTCTCTAGGGCAGAGGGCCACCATATCCTGCAGAGCCAGTGAAAGT

GTTGATAGTTATGGCAATAGTTTTATGCACTGGTATCAGCAGAAACCAGG

ACAGCCACCCAAACTCCTCATCTATCGTGCATCCAACCTAGAATCTGGGA

TCCCTGCCAGGTTCAGTGGCAGTGGGTCTAGGACAGACTTCACCCTCACC

ATTAATCCTGTGGAGGCTGATGATGTTGCAACCTATTACTGTCAGCAAAG

TAATGAGGATCTGACGTTCGGCCAAGGGACCAAGGTGGAAATCAAACGTA

CGGTGGCTGCACCATCTGTCTTCATCTTCCCGCCATCTGATGAGCAGTTG

AAATCTGGAACTGCCTCTGTTGTGTGCCTGCTGAATAACTTCTATCCCAG

AGAGGCCAAAGTACAGTGGAAGGTGGATAACGCCCTCCAATCGGGTAACT

CCCAGGAGAGTGTCACAGAGCAGGACAGCAAGGACAGCACCTACAGCCTC

AGCAGCACCCTGACGCTGAGCAAAGCAGACTACGAGAAACACAAAGTCTA

CGCCTGCGAAGTCACCCATCAGGGCCTGAGCTCGCCCGTCACAAAGAGCT

TCAACAGGGGAGAGTGT

Amino Acid Sequence of BAP070-01-Light Chain Protein (SEQ ID NO: 38)
MDMRVPAQLLGLLLLWLPGAKCDIVLTQSPASLAVSLGQRATISCRASES

VDSYGNSFMHWYQQKPGQPPKLLIYRASNLESGIPARFSGSGSRTDFTLT

INPVEADDVATYYCQQSNEDLTFGQGTKVEIKRTVAAPSVFIFPPSDEQL

KSGTASVVCLLNNFYPREAKVQWKVDNALQSGNSQESVTEQDSKDSTYSL

SSTLTLSKADYEKHKVYACEVTHQGLSSPVTKSFNRGEC

BAP070-01-Heavy Chain DNA Sequence (SEQ ID NO: 39)
ATGGCCACAACCATGGAGTTTGGGCTGAGCTGGCTTTTTCTTGTGGCTAT

TTTAAAAGGTGTCCAGTGTCAGATCCAGTTGGTGCAGTCTGGACCTGAGC

TGAAGAAGCCTGGAGAGACAGTCAAGATCTCCTGCAAGGCTTCTGGGTAT

ACCTTCACAAACTATGGAATGAACTGGGTGAAGCAGGCTCCAGGAAAGGG

TTTAAAGTGGATGGGCTGGATAAACACCTACACTGGAGAGCCAACATATG

CTGATGACTTCAAGGGACGGTTTGCCTTCTCTTTGGAAACCTCTGCCAGC

ACTGCCTATTTGCAGATCAACAACCTCAAAAATGAGGACACGGCTACATA

TTTCTGTACAACGTACGCTACTAGCTGGTACTGGGGCCAGGGAACGCTGG

TCACCGTCAGCTCAGCCTCCACCAAGGGCCCATCGGTCTTCCCCCTGGCA

CCCTCCTCCAAGAGCACCTCTGGGGGCACAGCGGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCA

GACCTACATCTGCAACGTGAATCACAAGCCCAGCAACACCAAGGTGGACA

AGAAAGTTGAGCCCAAATCTTGTGACAAAACTCACACATGCCCACCGTGC

CCAGCACCTGAACTCCTGGGGGGACCGTCAGTCTTCCTCTTCCCCCCAAA

ACCCAAGGACACCCTCATGATCTCCCGGACCCCTGAGGTCACATGCGTGG

TGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCAGCAACAAAGCCCTCCCA

GCCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

-continued
GAGGCTCTGCACAACCACTACACGCAGAAGAGCCTCTCCCTGTCTC CGG

GTAAA

Amino Acid Sequence of BAP070-01-Heavy Chain Protein (SEQ ID NO: 40)
MATTMEFGLSWLFLVAILKGVQCQIQLVQSGPELKKPGETVKISCKASGY

TFTNYGMNWVKQAPGKGLKWMGWINTYTGEPTYADDFKGRFAFSLETSAS

TAYLQINNLKNEDTATYFCTTYATSWYWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK

Murine mAb 583 Heavy Chain Variable Region Sequence:

(SEQ ID NO: 53)
CAGATCCAGTTGGTGCAGTCTGGACCTGAGCTGAAGAAGCCTGGAGAGAC

AGTCAAGATCTCCTGCAAGGCTTCTGGGTATACCTTCACAAACTATGGAA

TGAACTGGGTGAAGCAGGCTCCAGGAAAGGGTTTAAAGTGGATGGGCTGG

ATAAACACCTACACTGGAGAGCCAACATATGCTGATGACTTCAAGGGACG

GTTTGCCTTCTCTTTGGAAACCTCTGCCAGCACTGCCTATTTGCAGATCA

ACAACCTCAAAAATGAGGACACGGCTACATATTTCTGTACAACGTACGCT

ACTAGCTGGTACTGGGGCCAAGGCACCACTCTCACAGTCTCCTCA

Murine mAb 583 Light Chain Variable Region Sequence:

(SEQ ID NO: 54)
GACATTGTGCTGACCCAATCTCCAGCTTCTTTGGCTGTGTCTCTAGGGCA

GAGGGCCACCATATCCTGCAGAGCCAGTGAAAGTGTTGATAGTTATGGCA

ATAGTTTTATGCACTGGTATCAGCAGAAACCAGGACAGCCACCCAAACTC

CTCATCTATCGTGCATCCAACCTAGAATCTGGGATCCCTGCCAGGTTCAG

TGGCAGTGGGTCTAGGACAGACTTCACCCTCACCATTAATCCTGTGGAGG

CTGATGATGTTGCAACCTATTACTGTCAGCAAAGTAATGAGGATCTGACG

TTCGGTGGAGGCACCAAGCTGGAAATCAAAC

CHO cells were seeded in 6 well plates, transfected with BAP070-01 (recombinant chimera) or empty vector only (BAP070) using a proprietary transfection protocol and cultured at 37° C. in DMEM with 10% serum. Supernatants were collected at 48 hours post-transfection. Concentration of IgG in the supernatant was determined using BioAtla's quantitation ELISA. The concentration of the recombinant BAP070-01 was determined by quantitation ELISA to be 3650 ng/ml.

Figure 29:
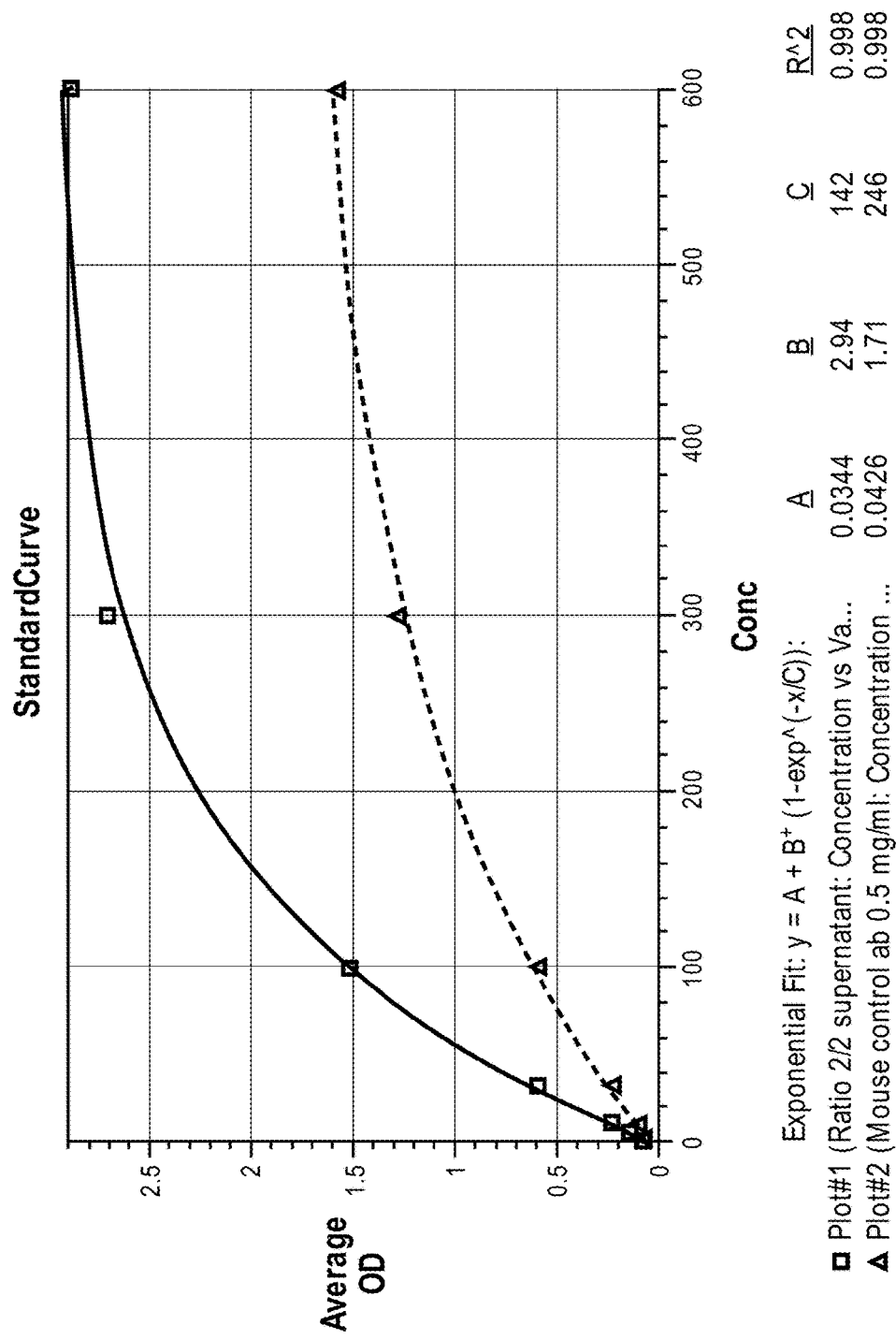
FIG. 29. Comparison of the MAb 583 chimera to murine MAb 583 for binding to a Hepcidin-25 coated ELISA plate. 100 ng hepcidin-25 was covalently bound to wells of a maleic anhydride activated 96 well microplate. Increasing amounts of MAb 583 chimera (BAP070-01; 3650 ng/ml; open squares) and murine MAb 583 (positive control MAb; open triangles) were added to microwell plate and allowed to bind for one hour. Binding of MAb 583 chimera was detected by rabbit anti-human IgG$_1$ (H+L) HRP. Bound murine MAb 583 antibody was detected with anti-mouse IgG$_1$ (H+L) conjugated with HRP. The reactions were stopped with 1N HCl at 5 minutes after TMB was added to the wells and read immediately. Binding was quantified as OD on a spectrophotometer at 450 nm after addition of stop solution. X axis: Antibody concentration in ng/ml; and Y axis: OD 450 nm values.

Our first experiment with the BAP070-01 MAb 583 chimera was designed to compare the MAb 583 chimera to the murine MAb 583 for binding activity to hepcidin-25. Two-fold and then three-fold dilution series of BAP070-1 CHO cell supernatant or murine MAb 583 (Lot 10, 0.5 mg/ml) starting at 600 ng/ml was incubated in microwell plates with 100 ng of hepcidin-25 covalently bound to the maleic anhydride activated wells. Antibody binding was detected with anti-human IgG (H+L) conjugated with HRP (1:2500) for BAP070-01 supernatant. Antibody binding by the purified MAb 583 control was detected using rabbit anti-mouse IgG (H+L) at the same dilution. The reactions were stopped with 1N HCl at 5 minutes after TMB was added to the wells and read immediately. OD 450 nm value of the reactions was measure with Molecular Device SPECTRAmax Plus (FIG. 29). The OD results shown in the table below and in FIG. 29 demonstrate excellent binding by the BAP070-01 chimeric MAb 583 and the purified MAb 583 control indicating that the BAP070-01 chimera clone was constructed correctly and that the murine heavy chain and light chain CDRs functioned correctly in the context of the human IgG framework. These data confirm that the cloning, expression of the BAP070-01 in CHO cell culture, and chimera binding activity are sufficiently robust to continue the humanization protocol. We conducted additional experiments to confirm the initial observation.

OD 450 nm values are as follows:

| [ng/ml] | BAP070-01 | Murine MAb 583 |
| --- | --- | --- |
| 600 | 2.8799 | 1.5871 |
| 300 | 2.6993 | 1.285 |
| 100 | 1.5046 | 0.5912 |
| 33.3 | 0.591 | 0.2297 |
| 11 | 0.2295 | 0.1035 |
| 3.6 | 0.1257 | 0.078 |
| 1.2 | 0.0848 | 0.0677 |
| 0.4 | 0.0723 | 0.065 |

The MAb 583 chimera, BAP070-01, clearly bound to hepcidin-25 to a greater degree that did the serially diluted purified murine MAb 583 in this experiment, confirming the chimeric antibodies specificity and functionality is comparable to the parent murine MAb 583 (FIG. 29).

This initial binding assay was a semi-quantitative assessment of the BAP070-01 chimera since the comparison involves a cell culture supernatant of a human-mouse chimeric MAb 583 with a purified murine MAb 583. Quantitation of chimeric antibody concentration in cell culture supernatants was performed using a proprietary immunological method and purified MAb 583 using BCA. The different assay can potentially lead to comparison of unequal amounts of antibody, and thus signal, in an ELISA comparison. Despite these caveats, both MAb 583 and the BAP070-01 chimera show increasing signal with increasing antibody as is predicted for this comparison.

583 Chimera Titering by Hepcidin-25 Coated Plate.

To compare the binding activity of BAP070-01 and the empty vector, BAP070 was determined by ELISA. Briefly, human hepcidin-25 (100 ng/well) was covalently bound to maleic anhydride activated microwell plates overnight and the remaining unbound activated sites were blocked as per manufacturer's instructions. Serially diluted culture supernatants containing the MAb 583 chimera, BAP070-01, or for the empty vector, BAP070, were added to the microwell plate and incubated at room temperature (RT) for 2 hours. Bound chimeric MAb 583 antibody was detected using anti-human IgG-HRP with TMB as substrate. The results are shown in FIG. 30.

Figure 30:
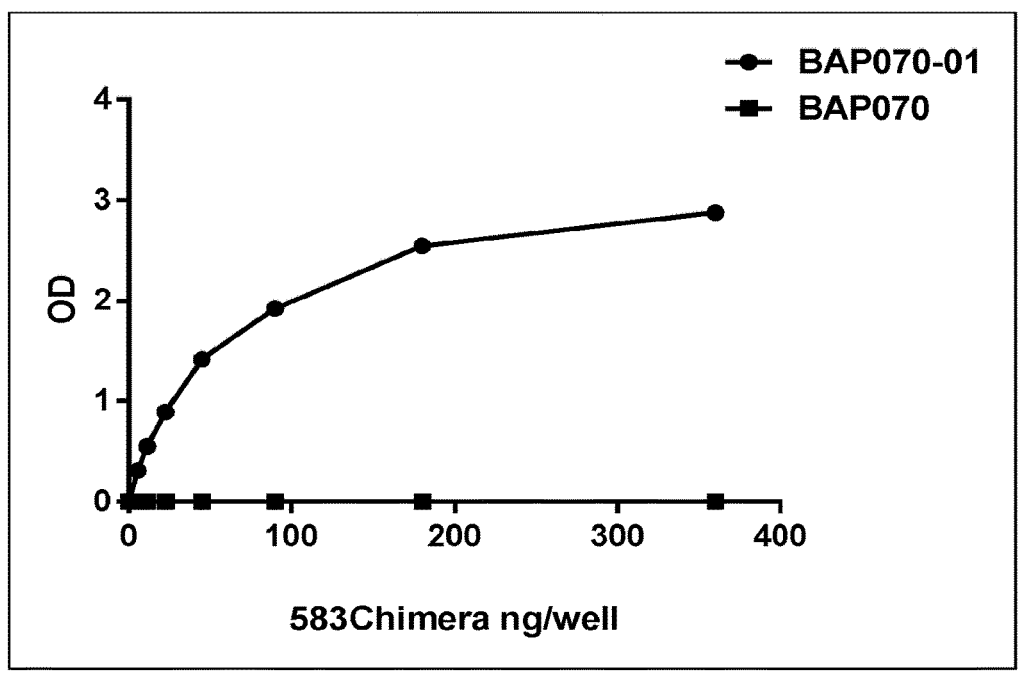
FIG. 30. MAb 583 chimera binding to a hepcidin-25 coated ELISA plate. 100 ng hepcidin-25 was covalently bound to wells of a maleic anhydride activated 96 well microplate. Increasing amounts of MAb 583 chimera (BAP070-01; 3650 ng/ml; filled circles) and supernatant from cells transfected with empty vector (BAP070; filled squares) were added to microwell plate and allowed to bind for 2 hours. Binding of MAb 583 chimera was detected by rabbit anti-human IgG1 (H+L) HRP with TMB as substrate. Binding was quantified on a spectrophotometer at 450 nm after addition of stop solution.

The data clearly indicates that the BAP070-01 human-mouse chimeric MAb specifically recognizes human hepcidin-25 with excellent affinity while there is no binding to hepcidin-25 by BAP070 CHO supernatant in this assay (FIG. 30). The data shown in FIGS. 29 and 30 demonstrate a very positive comparison of purified MAb 583 and the BAP070-01 chimeric MAb 583 and the hepcidin-25 specific binding of the of the BAP070-01 chimera. The expected ELISA results comparing the supernatants of the BAP070-01 chimera to the negative control BAP070 empty vector was demonstrated using hepcidin-25 coated plates to capture functional human IgG antibodies and anti-human IgG (H+L) antibodies for detection (FIG. 30).

Protein G Coated C-ELISA for BAP070-01 583 Chimera

Figure 31:
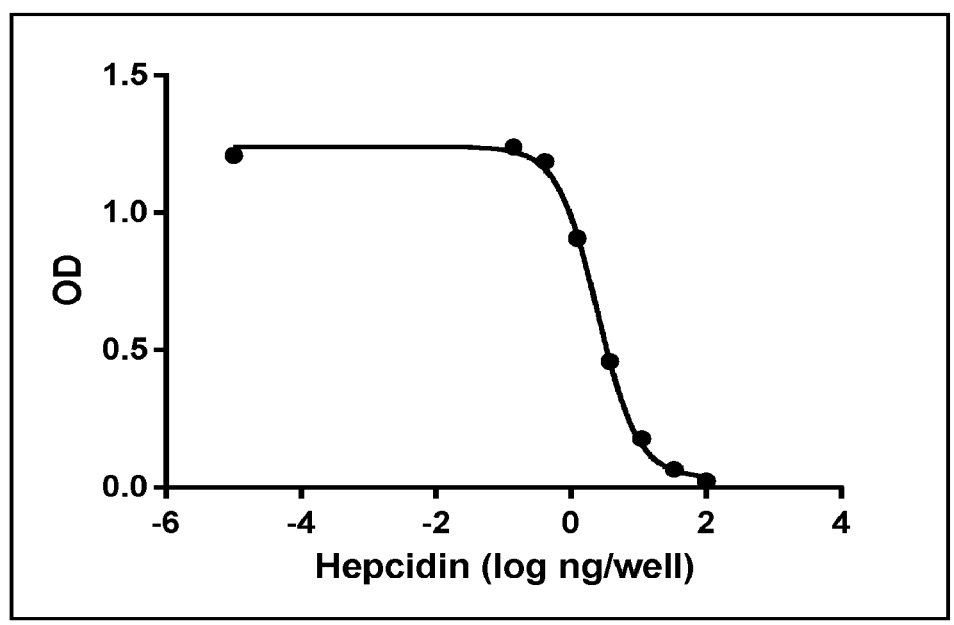
FIG. 31. Hepcidin-25 standard curve produced using the BAP070-01 MAb 583 chimera. Wells on microwell plate were coated with 150 ng/ml Protein G and blocked. The Mab 583 chimera (BAP070-01) was added to the wells at 150 ng/well and allowed to bind for one hours. Known concentrations of synthetic hepcidin-25 was added to assay buffer containing NT-biotin hepcidin-25 (1 ng/well), mixed, and added to 8 duplicate wells and allowed to compete for two hours. The wells were washed and SA-HRP with TMB substrate was used to detect binding of the NT-biotin hepcidin-25 tracer. Binding was quantified on a spectrophotometer at 450 nm after addition of stop solution. The standard curve was generated using Graphpad Prism software (San Diego, Calif.) using a 4-parameter logistical regression.

To assess binding of the BAP070-01 chimera to Protein G and the degree of neutralization of the BAP070-01 MAb 583 by synthetic hepcidin-25 we performed a C-ELISA assay using NT-biotin hepcidin-25 as the tracer (FIG. 31). This C-ELISA format also was useful to test the binding of NT-biotin hepcidin-25 tracer to the BAP070-01 chimera and compete with hepcidin-25 for binding to the chimeric MAb 583. To capture BAP070-01 chimeric antibodies we coated microwell plates with Protein G (150 ng/well) overnight in carbonate coating buffer.

The plate was washed with TBST and CHO cell supernatant containing the BAP070-01 MAb 583 chimera (150 ng/well) was added and allowed to bind to the Protein G at RT for 1 hour.

The plate was washed with TBST and one (1) ng/well of NT-biotin hepcidin-25 was mixed with different amounts (0-100 ng) of synthetic hepcidin-25 standard in TBST, 0.25% BLOTTO and added onto the plate to bind competitively. The plate was washed with TBST and SA-HRP (1:2500) added and allowed to bind for 1 hour.

The plate was washed with TBST and TBS substrate added and the reaction stopped after 10 minutes with stop solution. Absorbance at 450 nm was measured on a spectrophotometer.

Absorbance ($OD_{450}$) for C-ELISA of BAP070-01 is shown in the Table below.

| ng hepcidin | OD1 | OD2 | AVG O.D. | replicates ratio |
|---|---|---|---|---|
| 100.00 | 0.0231 | 0.0233 | 0.0232 | 99 |
| 33.33 | 0.0698 | 0.0621 | 0.0660 | 112 |
| 11.11 | 0.1710 | 0.1817 | 0.1764 | 94 |
| 3.70 | 0.4657 | 0.4511 | 0.4584 | 103 |
| 1.23 | 0.8793 | 0.9340 | 0.9067 | 94 |
| 0.41 | 1.1751 | 1.1974 | 1.1863 | 98 |
| 0.14 | 1.2469 | 1.2306 | 1.2388 | 101 |
| 0.00001 | 1.1811 | 1.2359 | 1.2085 | 96 |

The results in the table above and in FIG. 31 demonstrate that synthetic hepcidin-25 competes for BAP070-10 chimera binding sites competitively and that the chimeric MAb 583 antibodies are specific for hepcidin-25 and NT-biotin hepcidin-25. The standard curve shown in FIG. 31 was generated using a four parameter logistical regression (Graphpad Prism; San Diego, Calif.). We used Prism to calculate the EC50 for the binding of hepcidin-25 to BAP070-01 and determined EC50=54 ng/ml (FIG. 31). This EC50 is excellent considering that it is derived from a crude supernatant and not a purified MAb 583 where the EC50 is ≤5.0 ng/ml (FIG. 16).

Neutravidin C-ELISA for BAP070-01 583 Chimera

Another assessment of BAP070-01 chimeric MAb 583 was performed by coating microwell plates with neutravidin (150 ng/well) overnight in carbonate coating buffer. The plate was washed with TBST. The NT-biotin hepcidin-25 tracer was added at 1 ng/well with different concentrations of hepcidin-25 (0-100 ng/well) and allowed to bind at RT for 1 hour. Anti-human IgG (H+L)-HRP was used to detect bound BAP070-01 MAb 583 chimera in this C-ELISA analysis The table below shows both duplicate and mean $OD_{450}$ values relative to hepcidin-25 concentrations. The results show that human hepcidin-25 clearly neutralizes binding sites on the BAP070-01 chimera and that the NT-biotin hepcidin-25 tracer (hepcidin analog) binds efficiently.

| ng hepcidin | OD1 | OD2 | Mean O.D. | replicates ratio |
|---|---|---|---|---|
| 100.00 | 0.2236 | 0.2029 | 0.2133 | 110 |
| 33.33 | 0.5828 | 0.6466 | 0.6147 | 90 |
| 11.11 | 1.5866 | 1.4614 | 1.5240 | 109 |
| 3.70 | 1.7336 | 1.9523 | 1.8430 | 89 |
| 1.23 | 1.6484 | 1.7580 | 1.7032 | 94 |
| 0.41 | 1.8400 | 1.7147 | 1.7774 | 107 |
| 0.14 | 1.8255 | 1.5933 | 1.7094 | 115 |
| 0.00001 | 1.9864 | 1.5274 | 1.7569 | 130 |

Figure 32:
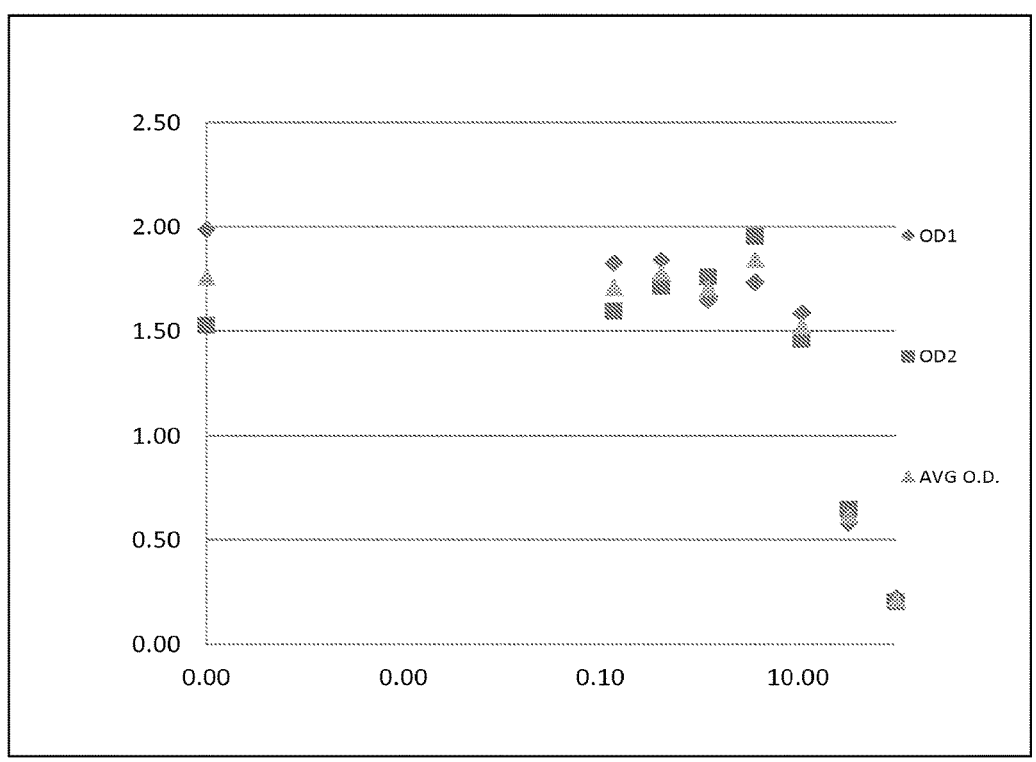
FIG. 32. Binding of MAb 583 chimera to NT-biotin hepcidin-25 on neutravidin coated microwell plates. Wells on microwell plate were coated with 150 ng/ml neutravidin and blocked. The NT-biotin hepcidin-25 tracer was added to wells at 1 ng/well and allowed to bind for one hour. The Mab 583 chimera (BAP070-01) was added to the wells at 150 ng/well along with synthetic hepcidin-25 at known concentrations and allowed to compete for binding to NT-biotin hepcidin-25 for one hour. Binding of the Mab 583 chimera was detected using rabbit anti-human IgG1 (H+L) HRP with TMB as substrate. Binding was quantified by spectropscopy at 450 nm after addition of stop solution. The points represent the two duplicates (filled diamonds and squares) and the mean (filled triangles).

FIG. 32 provides graphic data illustrating the results presented in the table above for competitive binding of the BAP070-01 chimera to NT-biotin hepcidin-25. As expected in any competitive assay, lower signal is observed with increasing unlabeled antigen (e.g. hepcidin-25) concentration. FIG. 32 shows the two duplicate $OD_{450}$ and the mean $OD_{450}$ value for each increasing concentration of hepcidin-25.

Cumulatively, the data we have presented in Example 10 demonstrates that the BAP070-01 chimeric Mab 583 retains the high affinity and specificity characteristics as the parent murine MAb 583 antibody and that complete humanization of the native murine MAb 583 antibody will yield a candidate therapeutic antibody suitable for pre-clinical and clinical testing in humans.

While certain embodiments of the present embodiments have been shown and described herein, it will be obvious to those skilled in the art that such embodiments are provided by way of example only. Numerous variations, changes, and substitutions will now occur to those skilled in the art without departing from the embodiments. It should be understood that various alternatives to the embodiments of the embodiments described herein may be employed in practicing the embodiments. It is intended that the following claims define the scope of the embodiments and that methods and structures within the scope of these claims and their equivalents be covered thereby.

SEQUENCES

Nucleotide Alignments of CDR-1, CDR-2, and CDR-3 Regions of Variable Heavy and Light Chains of Hepcidin MAbs H32, 583 and 1B1. CDRs are underlined. Framework regions are not underlined.

Variable Heavy Chain

CDR-1
H32
SEQ ID NO: 1
GGTTCT<u>GGCTACACATTCACTGATTATGCTATGCAC</u>

583
SEQ ID NO: 2
GCTTCT<u>GGGTATACCTTCACAAACTATGGAATGAAC</u>

-continued

1B1
SEQ ID NO: 3
GTCACTGGCTACTCAATCACCAGTGATTATGCCTGGAAC

CDR-2
H32
SEQ ID NO: 4
GGAGTTATTAGTTCTTACTATGGTGATGCTAGCTAC

583
SEQ ID NO: 5
GGCTGGATAAACACCTACACTGGAGAGCCAACATAT

1B1
SEQ ID NO: 6
GGCTACATAAGCTACAGTAGTATCACTAACTAC

CDR-3
H32
SEQ ID NO: 7
TACTGTGCAAGATATAGGGGGCTCTGGTACTTCGATGTCTGGGGC

583
SEQ ID NO: 8
TTCTGTACAACGTACGCTACTAGCTGGTACTGGGGC

1B1
SEQ ID NO: 9
TACTGTGCTGGTCTTTACTATGTTATGGACCACTGGGGT

Variable Light Chain

CDR-1
H32
SEQ ID NO: 10
TCTAGTAAGAGTCTCCTGCATAGTAATGGCAACACTTACTTGTAT

583
SEQ ID NO: 11
GCCAGTGAAAGTGTTGATAGTTATGGCAATAGTTTTATGCAC

1B1
SEQ ID NO: 12
GCCAGCTCAAGTGTAAGTTACATGTAC

CDR-2
H32
SEQ ID NO: 13
GTATATCGGATGTCCAACCTT

583
SEQ ID NO: 14
ATCTATCGTGCATCCAACCTA

1B1
SEQ ID NO: 15
ATTTATCTCACATCCAACCTG

CDR-3
H32
SEQ ID NO: 16
TATTGTATGCAACATCTAGAATATCCTTTCACGTTCGGT

583
SEQ ID NO: 17
TACTGTCAGCAAAGTAATGAGGATCTGACGTTCGGT

1B1
SEQ ID NO: 18
TACTGCCAGCAGTGGAGTAGTGACCCTTTCACGTTCGGC

Human hepcidin peptide (hepcidin-25, hep-25, Hep-25, hHepcidin-25): SEQ ID NO: 19 (25aa) DTHFPICIFCCGC-CHRSKCGMCCKT Mouse hepcidin-1 peptide (mhepcidin-1, mhep-1, mHep-1, mHepcidin-1): SEQ ID NO: 20: (25aa) DTNFPICIFC-CKCCNNSQCGICCKT Rat hepcidin peptide (rhepcidin, rhep, rHep, rHepcidin): SEQ ID NO: 21: (25aa) DTNFPICLFCCKCCKNSS-CGLCCIT Human hepcidin-20 peptide (hepcidin-20, hep-20, Hep-25, hHepcidin-20): SEQ ID NO: 22: (20aa) ICIFCCGC-CHRSKCGMCCKT Human hepcidin 22 peptide (hepcidin-22, hep-22, Hep-22, hHepcidin-22): SEQ ID NO: 23: (23aa) HFPICIFC-CGCCHRSKCGMCCKT Human hepcidin-9 peptide (hepcidin-9, hep-9, Hep-9, hHepcidin-9): SEQ ID NO: 24 (9aa) DTHFPICIF Human hepcidin-5 peptide (hepcidin-5, hep-5, Hep-5, hHepcidin-5): SEQ ID NO: 25 (5aa) DTHFP Human hepcidin 10-25 peptide (hepcidin 10-25, hep 10-25, Hep 10-25, hHepcidin 10-25): SEQ ID NO: 26 (16aa) CCGCCHRSKCGMCCKT DNP-human hepcidin-9 KLH peptide (DNP-hepcidin-9-KLH, DNP-hep-9-KLH, DNP-Hep-9-KLH, DNP-hHepcidin-9-KLH): SEQ ID NO: 27 DNP-DTHFPIC(KLH-SMCC)-IF IgG1 heavy chain variable region [Homo sapiens] GenBank: AAK62671.1

(SEQ ID NO: 29)
LLESGPGLLKPSETLSLTCTVSGGSMINYYWSWIRQPPGERPQWLGHIIY

GGTTKYNPSLESRITISRDISKSQFSLRLNSVTAADTAIYYCARVAIGVS

GFLNYYYYMDVWGSGTAVTVSS

IgG1 heavy chain variable region [Homo sapiens] GenBank: AAK19936.1

(SEQ ID NO: 30)
QVQLQQWGAGLLKPSETLSRTCAVYGGSFSDDYWSWIRQPPGKGLEWIGE

INHSGSTNYNPSLKSRVTISVDTSEKQFSLKLSSVTAADTAVYYCARRND

WYPFDYWDEGILVTVSSASTKGPSVFPLAPSSKSTSGGTAALGCLVKDYF

PEPVTVSW

IgG1 [Mus musculus] GenBank: BAA23565.1

(SEQ ID NO: 31)
QVQLQQSGAELMKPGASVNISCKASGYIFSSYWIEWVKQRPGHGLEWIGE

ILPGSGNIKYNEKFKGKAIFTVETSSNTAYMQLSSLTSEDSAVYFCAKTD

YYASGYGFDYWGQGTTVTVSS

Immunoglobulin kappa light chain variable region [Mus musculus] GenBank: ABE03 823.1

(SEQ ID NO: 32)
DIVMTQSPASLDVSLGQRATISCRASKSVSTSGYSYMNWYQQKPGQPPKL

LIYLASSLESGVPARFSGSGSGTDFTLNIHPVEEEDAATYYCQHSREPPP

TFGGGTKLEIKRAD

Immunoglobulin kappa light chain variable region [Mus musculus] GenBank: ABE03821.1

(SEQ ID NO: 33)
DVVMTQSPLTLSVTIGQPASISCKSSQSLLANNGRTYLNWLLQRPGQSPK

RLIYLVSTLDSGVPDRFTGSGSGTDFTLKISRVEAEDLGVYYCWQGTHFP

LTFGAGTKLELKRAD

Immunoglobulin IgG1 light chain variable region [Homo sapiens] GenBank: AAK62672.1

(SEQ ID NO: 34)
LTQSPATLSLSPGERATLSCRASQSVGRNLGWYQQKPGQAPRLLIYDASN

RATGIPARFSGSGSGTDFTLTISSLEPEDFAVYYCQQRSDWPRTFGQGTK

VEIKR

Mouse_VK (SEQ ID NO: 35)
QIVLSQSPAILSASPGEKVTMTCRASSSVSYMHWYQQKPGSSPKPWIYAT

SNLASGVPVRFSGSGSGTSYSLTISRVEAEDAATYYCQQWSSNPLTFGAG

TKLELK

Mouse V_VH (SEQ ID NO: 36)
EVKLEESGGGLVQPGGSMKLSCAASGFTFSDAWMDWVRQSPEKGLEWVAE

IRSKASNHATYYAESVKGRFTISRDDSKSSVYLQMNSLRAEDTGIYYCTR

WRRFFDSWGQGTTLTVSS

Variable Heavy and Light Chain Nucleic Acid and Amino Acid Sequences of Hepcidin MAbs H32, 583 and 1B1.

H32 VH (SEQ ID NO: 41)
GGTTCTGGCTACACATTCACTGATTATGCTATGCACGGAGTTATTAGTTC

TTACTATGGTGATGCTAGCTACTACTGTGCAAGATATAGGGGGCTCTGGT

ACTTCGATGTCTGGGGC

H32 VH (SEQ ID NO: 42)
Gly Ser Gly Tyr Thr Phe Thr Asp Tyr Ala Met His

Gly Val Ile Ser Ser Tyr Tyr Gly Asp Ala Ser Tyr

Tyr Cys Ala Arg Tyr Arg Gly Leu Trp Tyr Phe Asp

Val Trp Gly

583 VH (SEQ ID NO: 43)
GCTTCTGGGTATACCTTCACAAACTATGGAATGAACGGCTGGATAAACAC

CTACACTGGAGAGCCAACATATTTCTGTACAACGTACGCTACTAGCTGGT

ACTGGGGC

583 VH (SEQ ID NO: 44)
Ala Ser Gly Tyr Thr Phe Thr Asn Tyr Gly Met Asn

Gly Trp Ile Asn Thr Tyr Thr Gly Glu Pro Thr Tyr

Phe Cys Thr Thr Tyr Ala Thr Ser Trp Tyr Trp Gly

1B1 VH (SEQ ID NO: 45)
GTCACTGGCTACTCAATCACCAGTGATTATGCCTGGAACGGCTACATAAG

CTACAGTAGTATCACTAACTACTACTGTGCTGGTCTTTACTATGTTATGG

ACCACTGGGGT

1B1 VH (SEQ ID NO: 46)
Val Thr Gly Tyr Ser Ile Thr Ser Asp Tyr Ala Trp

Asn Gly Tyr Ile Ser Tyr Ser Ser Ile Thr Asn Tyr

Tyr Cys Ala Gly Leu Tyr Tyr Val Met Asp His Trp

Gly

H32 VL (SEQ ID NO: 47)
TCTAGTAAGAGTCTCCTGCATAGTAATGGCAACACTTACTTGTATGTATA

TCGGATGTCCAACCTTTATTGTATGCAACATCTAGAATATCCTTTCACGT

TCGGT

H32 VL (SEQ ID NO: 48)
Ser Ser Lys Ser Leu Leu His Ser Asn Gly Asn Thr

Tyr Leu Tyr Val Tyr Arg Met Ser Asn Leu Tyr Cys

Met Gln His Leu Glu Tyr Pro Phe Thr Phe Gly

583 VL (SEQ ID NO: 49)
GCCAGTGAAAGTGTTGATAGTTATGGCAATAGTTTTATGCACATCTATCG

TGCATCCAACCTATACTGTCAGCAAAGTAATGAGGATCTGACGTTCGGT

583 VL (SEQ ID NO: 50)
Ala Ser Glu Ser Val Asp Ser Tyr Gly Asn Ser Phe

Met His Ile Tyr Arg Ala Ser Asn Leu Tyr Cys Gln

Gln Ser Asn Glu Asp Leu Thr Phe Gly

1B1 VL (SEQ ID NO: 51)
GCCAGCTCAAGTGTAAGTTACATGTACATTTATCTCACATCCAACCTGTA

CTGCCAGCAGTGGAGTAGTGACCCTTTCACGTTCGGC

1B1 VL (SEQ ID NO: 52)
Ala Ser Ser Ser Val Ser Tyr Met Tyr Ile Tyr Leu

Thr Ser Asn Leu Tyr Cys Gln Gln Trp Ser Ser Asp

Pro Phe Thr Phe Gly

CDR-1, CDR-2, and CDR-3 polynucleotide sequences of Variable Heavy and Light Chains of Hepcidin MAbs H32, 583 and 1B1.

Variable Heavy Chain

CDR-1
H32

SEQ ID NO: 55
GGCTACACATTCACTGATTATGCT

583

SEQ ID NO: 56
GGGTATACCTTCACAAACTATGGA

1B1

SEQ ID NO: 57
GGCTACTCAATCACCAGTGATTATGCC

CDR-2
H32

SEQ ID NO: 58
ATTAGTTCTTACTATGGTGATGCT

583

SEQ ID NO: 59
ATAAACACCTACACTGGAGAGCCA

1B1

SEQ ID NO: 60
ATAAGCTACAGTAGTATCACT

-continued

Variable Light Chain

CDR-3
H32
SEQ ID NO: 61
GCAAGATATAGGGGGCTCTGGTACTTCGATGTC

583
SEQ ID NO: 62
ACAACGTACGCTACTAGCTGGTAC

1B1
SEQ ID NO: 63
GCTGGTCTTTACTATGTTATGGACCAC

CDR-1
H32
SEQ ID NO: 64
AAGAGTCTCCTGCATAGTAATGGCAACACTTAC

583
SEQ ID NO: 65
GAAAGTGTTGATAGTTATGGCAATAGTTTT

1B1
SEQ ID NO: 66
TCAAGTGTAAGTTAC

CDR-2
H32
SEQ ID NO: 67
CGGATGTCC

583
SEQ ID NO: 68
CGTGCATCC

1B1
SEQ ID NO: 69
CTCACATCC

-continued

CDR-3
H32
SEQ ID NO: 70
ATGCAACATCTAGAATATCCTTTCACG

583
SEQ ID NO: 71
CAGCAAAGTAATGAGGATCTGACG

1B1
SEQ ID NO: 72
CAGCAGTGGAGTAGTGACCCTTTCACG

REFERENCES

Hunter et al., *J. Biol. Chem.*, 277:37597-37603 (2002)
Kemna et al., *Blood*, 106:1864-1866, 2005
Kilpatrick K E, Wring S A, Walker D H, et al. 1997. Rapid Development of Monoclonal Antibodies Using Repetitive Immunization, Multiple Sites.
Krause et al., *FEBS Lett.* 480:147 (2000)
Lauth et al., *J. Biol. Chem.*, 280:9272-9282 (2005)
Nemeth et al., *J. Clin. Invest.*, 113:1271-1276, 2004
Nemeth et al., *Blood,* 101:2461-2463, 2003
Nicolas et al., *Nat. Genet.*, 34:97-101, 2003
Nicolas et al., *Proc. Natl. Acad. Sci. USA,* 99:4596-4601, 2002
Nicolas et al., *Proc. Natl. Acad. Sci. USA,* 98:8780-8785, 2001.
Nicolas et al., *J. Clin. Invest.*, 110:1037-1044, 2002
Park et al., *J. Biol. Chem.* 276:7806 (2001)
Pigeon et al., *J. Biol. Chem.* 276:7811 (2001)
Rivera et al., *Blood*, 105:1797-1802, 2005
Roetto et al., *Nat. Genet.*, 33:21-22, 2003
Weinstein et al., *Blood*, 100:3776-36781, 2002 The N-terminus of hepcidin is essential for its interaction with ferroportin:
Nemeth et al., *Blood,* 107(1):328-333, 2006.

---

What is claimed is:

1. A method of treating a disorder of iron homeostasis associated with elevated hepcidin levels in a subject in need thereof, comprising administering to the subject a composition that comprises an antibody, or antigen-binding fragment thereof, that specifically binds to hepcidin (Hep) or a hepcidin peptide, wherein the antibody, or antigen-binding fragment thereof, comprises a heavy chain Complementary Determining Region 1 (CDR1) encoded by SEQ ID NO: 57, a heavy chain CDR2 encoded by SEQ ID NO: 60, a heavy chain CDR3 encoded by SEQ ID NO: 63, a light chain CDR1 encoded by SEQ ID NO: 66, a light chain CDR2 encoded by SEQ ID NO: 69, and a light chain CDR3 encoded by SEQ ID NO: 72, and an acceptable carrier or excipient.

2. The method of claim 1, wherein the disorder of iron homeostasis comprises an anemia.

3. The method of claim 2, wherein the anemia comprises an iron refractory iron deficiency anemia (IRIDA).

4. The method of claim 2, wherein the anemia comprises an Anemia of Chronic Disease (ACD), an Anemia of Cancer, an Anemia of Inflammation, a Congenital Dyserythropoietic Anemia, a Hypochromic Microcytic Anemia, or a Chemotherapy Induced Anemia (CIA).

5. The method of claim 1, wherein the disorder of iron homeostasis comprises a hemochromatosis.

6. The method of claim 5, wherein the hemochromatosis comprises Neonatal Hemochromatosis or Juvenile Hemochromatosis.

7. The method of claim 1, wherein the disorder of iron homeostasis comprises an inflammatory disease.

8. The method of claim 1, wherein the disorder of iron homeostasis comprises a Chronic Kidney Disease, Collagen-Induced Arthritis, a Ferroportin Disease, Parkinson's Disease, Crohn's Disease, Celiac Disease, an Acute Kidney Injury, Friedrich's ataxia, a Hepatitis, Huntingdon's Disease, hyperferritinemia, Multiple Sclerosis, Rheumatoid Arthritis, Thalassemia, an Inflammatory Bowel Disease, or Wilson's Disease.

9. The method of claim 1, wherein the antibody or antigen-binding fragment thereof, comprises a heavy chain variable amino acid sequence represented by SEQ ID NO: 46 and a light chain variable amino acid sequence represented by SEQ ID NO: 52.

10. A method of reducing hepcidin activity in a subject in need thereof, comprising administering to the subject a composition that comprises an antibody, or antigen-binding fragment thereof, that specifically binds to hepcidin (Hep) or a hepcidin peptide, wherein the antibody, or antigen-binding fragment thereof, comprises a heavy chain CDR1 encoded by SEQ ID NO: 57, a heavy chain CDR2 encoded by SEQ ID NO: 60, a heavy chain CDR3 encoded by SEQ ID NO: 63, a light chain CDR1 encoded by SEQ ID NO: 66, a light chain CDR2 encoded by SEQ ID NO: 69, and a light chain CDR3 encoded by SEQ ID NO: 72, and an acceptable carrier or excipient.

11. The method of claim 10, wherein the subject has an infection, and the infection comprises a bacterial infection, a fungal infection, or a viral infection.

12. The method of claim 10, wherein the antibody or antigen-binding fragment thereof, comprises a heavy chain variable amino acid sequence represented by SEQ ID NO: 46 and a light chain variable amino acid sequence represented by SEQ ID NO: 52.

13. The method of claim 1 or 10, further comprising administering to the subject a erythropoiesis stimulator, wherein the erythropoiesis stimulator is selected from the group consisting of erythropoietin, an erythropoietin variant, a hypoxia inducible factor (HIF) prolyl hydroxylase inhibitor, a bone marrow derived erythroid factor, a mini-hepcidin peptide, an anti-BMP-2 antibody, an anti-BMP-4 antibody, an anti-BMP-6 antibody, an anti-IL-6 antibody, an anti-TNF-alpha antibody, methotrexate, an anti-inflammatory agent, hemojuvelin, and an antibody that binds erythropoietin.

14. A method of treating a disorder of iron homeostasis associated with elevated hepcidin levels in a subject in need thereof, comprising administering to the subject a composition that comprises an antibody, or antigen-binding fragment thereof, that specifically binds to hepcidin (Hep) or a hepcidin peptide, wherein the antibody, or antigen-binding fragment thereof, comprises a heavy chain CDR1 encoded by SEQ ID NO: 56, a heavy chain CDR2 encoded by SEQ ID NO: 59, a heavy chain CDR3 encoded by SEQ ID NO: 62, a light chain CDR1 encoded by SEQ ID NO: 65, a light chain CDR2 encoded by SEQ ID NO: 68, and a light chain CDR3 encoded by SEQ ID NO: 71, and an acceptable carrier or excipient.

15. The method of claim 14, wherein the disorder of iron homeostasis comprises an anemia.

16. The method of claim 15, wherein the anemia comprises an Anemia of Chronic Disease (ACD), an Anemia of Cancer, an Anemia of Inflammation, a Congenital Dyserythropoietic Anemia, a Hypochromic Microcytic Anemia, or a Chemotherapy Induced Anemia (CIA).

17. The method of claim 15, wherein the anemia comprises an iron refractory iron deficiency anemia (IRIDA).

18. The method of claim 14, wherein the disorder of iron homeostasis comprises a hemochromatosis.

19. The method of claim 18, wherein the hemochromatosis comprises Neonatal Hemochromatosis or Juvenile Hemochromatosis.

20. The method of claim 14, wherein the disorder of iron homeostasis comprises an inflammatory disease.

21. The method of claim 14, wherein the disorder of iron homeostasis comprises an infection, and the infection comprises a bacterial infection, a fungal infection, or a viral infection.

22. The method of claim 14, wherein the disorder of iron homeostasis comprises a Chronic Kidney Disease, Collagen-Induced Arthritis, a Ferroportin Disease, Parkinson's Disease, Crohn's Disease, Celiac Disease, an Acute Kidney Injury, Friedrich's ataxia, a Hepatitis, Huntingdon's Disease, hyperferritinemia, Multiple Sclerosis, Rheumatoid Arthritis, Thalassemia, an Inflammatory Bowel Disease, or Wilson's Disease.

23. A method of reducing hepcidin activity in a subject in need thereof, comprising administering to the subject a composition that comprises an antibody, or antigen-binding fragment thereof, that specifically binds to hepcidin (Hep) or a hepcidin peptide, wherein the antibody, or antigen-binding fragment thereof, comprises a heavy chain CDR1 encoded by SEQ ID NO: 56, a heavy chain CDR2 encoded by SEQ ID NO: 59, a heavy chain CDR3 encoded by SEQ ID NO: 62, a light chain CDR1 encoded by SEQ ID NO: 65, a light chain CDR2 encoded by SEQ ID NO: 68, and a light chain CDR3 encoded by SEQ ID NO: 71, and an acceptable carrier or excipient.

24. The method of claim 14 or 23, further comprising administering to the subject a erythropoiesis stimulator, wherein the erythropoiesis stimulator is selected from the group consisting of erythropoietin, an erythropoietin variant, a hypoxia inducible factor (HIF) prolyl hydroxylase inhibitor, a bone marrow derived erythroid factor, a mini-hepcidin peptide, an anti-BMP-2 antibody, an anti-BMP-4 antibody, an anti-BMP-6 antibody, an anti-IL-6 antibody, an anti-TNF-alpha antibody, methotrexate, an anti-inflammatory agent, hemojuvelin, and an antibody that binds erythropoietin.

25. A method of treating an anemia associated with an elevated level of hepcidin in a subject in need thereof, comprising administering to the subject a composition that comprises an antibody, or antigen-binding fragment thereof, that specifically binds to hepcidin (Hep) or a hepcidin peptide, wherein the antibody, or antigen-binding fragment thereof, comprises a heavy chain CDR1 encoded by SEQ ID NO: 57, a heavy chain CDR2 encoded by SEQ ID NO: 60, a heavy chain CDR3 encoded by SEQ ID NO: 63, a light chain CDR1 encoded by SEQ ID NO: 66, a light chain CDR2 encoded by SEQ ID NO: 69, and a light chain CDR3 encoded by SEQ ID NO: 72, and an acceptable carrier or excipient.

26. The method of claim 25, wherein the anemia comprises an iron refractory iron deficiency anemia (IRIDA).

27. The method of claim 25, wherein the anemia comprises an Anemia of Chronic Disease (ACD), an Anemia of Cancer, an Anemia of Inflammation, a Congenital Dyserythropoietic Anemia, a Hypochromic Microcytic Anemia, or a Chemotherapy Induced Anemia (CIA).

28. The method of claim 25, wherein the antibody or antigen-binding fragment thereof, comprises a heavy chain variable amino acid sequence represented by SEQ ID NO: 46 and a light chain variable amino acid sequence represented by SEQ ID NO: 52.

* * * * *

SEQUENCE LISTING

<160> NUMBER OF SEQ ID NOS: 72

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggttctggct acacattcac tgattatgct atgcac                                36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcttctgggt ataccttcac aaactatgga atgaac                                36

<210> SEQ ID NO 3
<211> LENGTH: 39
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 3
gtcactggct actcaatcac cagtgattat gcctggaac                           39

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggagttatta gttcttacta tggtgatgct agctac                              36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggctggataa acacctacac tggagagcca acatat                              36

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggctacataa gctacagtag tatcactaac tac                                 33

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tactgtgcaa gatatagggg gctctggtac ttcgatgtct ggggc                    45

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttctgtacaa cgtacgctac tagctggtac tggggc                              36

<210> SEQ ID NO 9
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 9
tactgtgctg gtctttacta tgttatggac cactggggt                           39

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tctagtaaga gtctcctgca tagtaatggc aacacttact tgtat                    45

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gccagtgaaa gtgttgatag ttatggcaat agttttatgc ac                       42

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gccagctcaa gtgtaagtta catgtac                                        27

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtatatcgga tgtccaacct t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atctatcgtg catccaacct a                                              21

<210> SEQ ID NO 15
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 15
atttatctca catccaacct g                                              21

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tattgtatgc aacatctaga atatcctttc acgttcggt                            39

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tactgtcagc aaagtaatga ggatctgacg ttcggt                               36

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tactgccagc agtggagtag tgaccctttc acgttcggc                            39

<210> SEQ ID NO 19
<211> LENGTH: 25
<212> TYPE: PRT
<213> ORGANISM: Homo sapiens

<400> SEQUENCE: 19

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 20
<211> LENGTH: 25
<212> TYPE: PRT
<213> ORGANISM: Mus sp.

<400> SEQUENCE: 20

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25
```

```
<210> SEQ ID NO 21
<211> LENGTH: 25
<212> TYPE: PRT
<213> ORGANISM: Rattus sp.

<400> SEQUENCE: 21

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 22
<211> LENGTH: 20
<212> TYPE: PRT
<213> ORGANISM: Homo sapiens

<400> SEQUENCE: 22

Ile Cys Ile Phe Cys Cys Gly Cys Cys His Arg Ser Lys Cys Gly Met
1               5                   10                  15

Cys Cys Lys Thr
            20

<210> SEQ ID NO 23
<211> LENGTH: 23
<212> TYPE: PRT
<213> ORGANISM: Homo sapiens

<400> SEQUENCE: 23

His Phe Pro Ile Cys Ile Phe Cys Cys Gly Cys Cys His Arg Ser Lys
1               5                   10                  15

Cys Gly Met Cys Cys Lys Thr
            20

<210> SEQ ID NO 24
<211> LENGTH: 9
<212> TYPE: PRT
<213> ORGANISM: Homo sapiens

<400> SEQUENCE: 24

Asp Thr His Phe Pro Ile Cys Ile Phe
1               5

<210> SEQ ID NO 25
<211> LENGTH: 5
<212> TYPE: PRT
<213> ORGANISM: Homo sapiens

<400> SEQUENCE: 25

Asp Thr His Phe Pro
1               5

<210> SEQ ID NO 26
<211> LENGTH: 16
<212> TYPE: PRT
<213> ORGANISM: Homo sapiens

<400> SEQUENCE: 26

Cys Cys Gly Cys Cys His Arg Ser Lys Cys Gly Met Cys Cys Lys Thr
1               5                   10                  15

<210> SEQ ID NO 27
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DNP-Asp
<220> FEATURE:
<221> NAME/KEY: MOD_RES
<222> LOCATION: (7)..(7)
<223> OTHER INFORMATION: Cys-(KLH-SMCC)

<400> SEQUENCE: 27

Asp Thr His Phe Pro Ile Cys Ile Phe
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 28

His His His His His His
1               5

<210> SEQ ID NO 29
<211> LENGTH: 122
<212> TYPE: PRT
<213> ORGANISM: Homo sapiens

<400> SEQUENCE: 29

Leu Leu Glu Ser Gly Pro Gly Leu Leu Lys Pro Ser Glu Thr Leu Ser
1               5                   10                  15

Leu Thr Cys Thr Val Ser Gly Gly Ser Met Ile Asn Tyr Tyr Trp Ser
                20                  25                  30

Trp Ile Arg Gln Pro Pro Gly Glu Arg Pro Gln Trp Leu Gly His Ile
            35                  40                  45

Ile Tyr Gly Gly Thr Thr Lys Tyr Asn Pro Ser Leu Glu Ser Arg Ile
        50                  55                  60

Thr Ile Ser Arg Asp Ile Ser Lys Ser Gln Phe Ser Leu Arg Leu Asn
65                  70                  75                  80

Ser Val Thr Ala Ala Asp Thr Ala Ile Tyr Tyr Cys Ala Arg Val Ala
                85                  90                  95

Ile Gly Val Ser Gly Phe Leu Asn Tyr Tyr Tyr Met Asp Val Trp
            100                 105                 110

Gly Ser Gly Thr Ala Val Thr Val Ser Ser
        115                 120

<210> SEQ ID NO 30
<211> LENGTH: 158
<212> TYPE: PRT
<213> ORGANISM: Homo sapiens

<400> SEQUENCE: 30

Gln Val Gln Leu Gln Gln Trp Gly Ala Gly Leu Leu Lys Pro Ser Glu
1               5                   10                  15

Thr Leu Ser Arg Thr Cys Ala Val Tyr Gly Gly Ser Phe Ser Asp Asp
                20                  25                  30

Tyr Trp Ser Trp Ile Arg Gln Pro Pro Gly Lys Gly Leu Glu Trp Ile
            35                  40                  45
```

Gly Glu Ile Asn His Ser Gly Ser Thr Asn Tyr Asn Pro Ser Leu Lys
            50                  55                  60

Ser Arg Val Thr Ile Ser Val Asp Thr Ser Glu Lys Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Asn Asp Trp Tyr Pro Phe Asp Tyr Trp Asp Glu Gly Ile Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp
145                 150                 155

<210> SEQ ID NO 31
<211> LENGTH: 121
<212> TYPE: PRT
<213> ORGANISM: Mus musculus

<400> SEQUENCE: 31

Gln Val Gln Leu Gln Gln Ser Gly Ala Glu Leu Met Lys Pro Gly Ala
 1               5                  10                  15

Ser Val Asn Ile Ser Cys Lys Ala Ser Gly Tyr Ile Phe Ser Ser Tyr
                 20                  25                  30

Trp Ile Glu Trp Val Lys Gln Arg Pro Gly His Gly Leu Glu Trp Ile
            35                  40                  45

Gly Glu Ile Leu Pro Gly Ser Gly Asn Ile Lys Tyr Asn Glu Lys Phe
    50                  55                  60

Lys Gly Lys Ala Ile Phe Thr Val Glu Thr Ser Ser Asn Thr Ala Tyr
 65                  70                  75                  80

Met Gln Leu Ser Ser Leu Thr Ser Glu Asp Ser Ala Val Tyr Phe Cys
                 85                  90                  95

Ala Lys Thr Asp Tyr Tyr Ala Ser Gly Tyr Gly Phe Asp Tyr Trp Gly
                100                 105                 110

Gln Gly Thr Thr Val Thr Val Ser Ser
            115                 120

<210> SEQ ID NO 32
<211> LENGTH: 114
<212> TYPE: PRT
<213> ORGANISM: Mus musculus

<400> SEQUENCE: 32

Asp Ile Val Met Thr Gln Ser Pro Ala Ser Leu Asp Val Ser Leu Gly
 1               5                  10                  15

Gln Arg Ala Thr Ile Ser Cys Arg Ala Ser Lys Ser Val Ser Thr Ser
                 20                  25                  30

Gly Tyr Ser Tyr Met Asn Trp Tyr Gln Gln Lys Pro Gly Gln Pro Pro
            35                  40                  45

Lys Leu Leu Ile Tyr Leu Ala Ser Ser Leu Glu Ser Gly Val Pro Ala
    50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

```
Glu Pro Pro Pro Thr Phe Gly Gly Gly Thr Lys Leu Glu Ile Lys Arg
            100                 105                 110
Ala Asp

<210> SEQ ID NO 33
<211> LENGTH: 115
<212> TYPE: PRT
<213> ORGANISM: Mus musculus

<400> SEQUENCE: 33

Asp Val Val Met Thr Gln Ser Pro Leu Thr Leu Ser Val Thr Ile Gly
1               5                   10                  15
Gln Pro Ala Ser Ile Ser Cys Lys Ser Ser Gln Ser Leu Leu Ala Asn
            20                  25                  30
Asn Gly Arg Thr Tyr Leu Asn Trp Leu Leu Gln Arg Pro Gly Gln Ser
        35                  40                  45
Pro Lys Arg Leu Ile Tyr Leu Val Ser Thr Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Trp Gln Gly
                85                  90                  95
Thr His Phe Pro Leu Thr Phe Gly Ala Gly Thr Lys Leu Glu Leu Lys
            100                 105                 110
Arg Ala Asp
        115

<210> SEQ ID NO 34
<211> LENGTH: 105
<212> TYPE: PRT
<213> ORGANISM: Homo sapiens

<400> SEQUENCE: 34

Leu Thr Gln Ser Pro Ala Thr Leu Ser Leu Ser Pro Gly Glu Arg Ala
1               5                   10                  15
Thr Leu Ser Cys Arg Ala Ser Gln Ser Val Gly Arg Asn Leu Gly Trp
            20                  25                  30
Tyr Gln Gln Lys Pro Gly Gln Ala Pro Arg Leu Leu Ile Tyr Asp Ala
        35                  40                  45
Ser Asn Arg Ala Thr Gly Ile Pro Ala Arg Phe Ser Gly Ser Gly Ser
    50                  55                  60
Gly Thr Asp Phe Thr Leu Thr Ile Ser Ser Leu Glu Pro Glu Asp Phe
65                  70                  75                  80
Ala Val Tyr Tyr Cys Gln Gln Arg Ser Asp Trp Pro Arg Thr Phe Gly
                85                  90                  95
Gln Gly Thr Lys Val Glu Ile Lys Arg
            100                 105

<210> SEQ ID NO 35
<211> LENGTH: 106
<212> TYPE: PRT
<213> ORGANISM: Mus sp.

<400> SEQUENCE: 35

Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Ser Val Ser Tyr Met
            20                  25                  30
```

```
His Trp Tyr Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys
            100                 105

<210> SEQ ID NO 36
<211> LENGTH: 118
<212> TYPE: PRT
<213> ORGANISM: Mus sp.

<400> SEQUENCE: 36

Glu Val Lys Leu Glu Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
             20                  25                  30

Trp Met Asp Trp Val Arg Gln Ser Pro Glu Lys Gly Leu Glu Trp Val
         35                  40                  45

Ala Glu Ile Arg Ser Lys Ala Ser Asn His Ala Thr Tyr Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Ile Tyr
                 85                  90                  95

Tyr Cys Thr Arg Trp Arg Arg Phe Phe Asp Ser Trp Gly Gln Gly Thr
            100                 105                 110

Thr Leu Thr Val Ser Ser
        115

<210> SEQ ID NO 37
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atggacatga gggtccccgc tcagctcctg gggctcctgc tgctctggct cccaggtgcc      60
aagtgtgaca ttgtgctgac ccaatctcca gcttctttgg ctgtgtctct agggcagagg     120
gccaccatat cctgcagagc cagtgaaagt gttgatagtt atggcaatag ttttatgcac     180
tggtatcagc agaaaccagg acagccaccc aaactcctca tctatcgtgc atccaaccta     240
gaatctggga tccctgccag gttcagtggc agtgggtcta ggacagactt caccctcacc     300
attaatcctg tggaggctga tgatgttgca acctattact gtcagcaaag taatgaggat     360
ctgacgttcg gccaagggac caaggtggaa atcaaacgta cggtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
```
agcagcaccc tgacgctgag caaagcagac tacgagaaac acaaagtcta cgcctgcgaa    660
gtcacccatc agggcctgag ctcgcccgtc acaaagagct tcaacagggg agagtgt       717

<210> SEQ ID NO 38
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Asp Met Arg Val Pro Ala Gln Leu Leu Gly Leu Leu Leu Leu Trp
1               5                   10                  15

Leu Pro Gly Ala Lys Cys Asp Ile Val Leu Thr Gln Ser Pro Ala Ser
            20                  25                  30

Leu Ala Val Ser Leu Gly Gln Arg Ala Thr Ile Ser Cys Arg Ala Ser
        35                  40                  45

Glu Ser Val Asp Ser Tyr Gly Asn Ser Phe Met His Trp Tyr Gln Gln
    50                  55                  60

Lys Pro Gly Gln Pro Pro Lys Leu Leu Ile Tyr Arg Ala Ser Asn Leu
65                  70                  75                  80

Glu Ser Gly Ile Pro Ala Arg Phe Ser Gly Ser Gly Ser Arg Thr Asp
                85                  90                  95

Phe Thr Leu Thr Ile Asn Pro Val Glu Ala Asp Asp Val Ala Thr Tyr
            100                 105                 110

Tyr Cys Gln Gln Ser Asn Glu Asp Leu Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 39
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atggccacaa ccatggagtt tgggctgagc tggcttttc ttgtggctat tttaaaaggt    60
gtccagtgtc agatccagtt ggtgcagtct ggacctgagc tgaagaagcc tggagagaca    120
gtcaagatct cctgcaaggc ttctgggtat accttcacaa actatggaat gaactgggtg    180
aagcaggctc aggaaagggg tttaaagtgg atgggctgga taaacaccta cactggagag    240

```
ccaacatatg ctgatgactt caagggacgg tttgccttct ctttggaaac ctctgccagc    300
actgcctatt tgcagatcaa caacctcaaa aatgaggaca cggctacata tttctgtaca    360
acgtacgcta ctagctggta ctggggccag ggaacgctgg tcaccgtcag ctcagcctcc    420
accaagggcc catcggtctt ccccctggca cctcctcca agagcacctc tgggggcaca     480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc      660 tgcaacgtga atcacaagcc cagcaacacc aaggtggaca gaaagttga cccaaatct       720 tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg     960
taccgtgtgg tcagcgtcct caccgtcctg caccaggact ggctgaatgg caaggagtac   1020
aagtgcaagg tcagcaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaa                                            1404

<210> SEQ ID NO 40
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ala Thr Thr Met Glu Phe Gly Leu Ser Trp Leu Phe Leu Val Ala
1               5                   10                  15

Ile Leu Lys Gly Val Gln Cys Gln Ile Gln Leu Val Gln Ser Gly Pro
            20                  25                  30

Glu Leu Lys Lys Pro Gly Glu Thr Val Lys Ile Ser Cys Lys Ala Ser
        35                  40                  45

Gly Tyr Thr Phe Thr Asn Tyr Gly Met Asn Trp Val Lys Gln Ala Pro
    50                  55                  60

Gly Lys Gly Leu Lys Trp Met Gly Trp Ile Asn Thr Tyr Thr Gly Glu
65                  70                  75                  80

Pro Thr Tyr Ala Asp Asp Phe Lys Gly Arg Phe Ala Phe Ser Leu Glu
                85                  90                  95

Thr Ser Ala Ser Thr Ala Tyr Leu Gln Ile Asn Asn Leu Lys Asn Glu
            100                 105                 110

Asp Thr Ala Thr Tyr Phe Cys Thr Thr Tyr Ala Thr Ser Trp Tyr Trp
        115                 120                 125
```

```
Gly Gln Gly Thr Leu Val Thr Val Ser Ser Ala Ser Thr Lys Gly Pro
    130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Gln Thr Tyr Ile Cys Asn Val Asn
    210                 215                 220
His Lys Pro Ser Asn Thr Lys Val Asp Lys Lys Val Glu Pro Lys Ser
225                 230                 235                 240
Cys Asp Lys Thr His Thr Cys Pro Pro Cys Pro Ala Pro Glu Leu Leu
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 41
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(117)
```

-continued

```
<400> SEQUENCE: 41 ggt tct ggc tac aca ttc act gat tat gct atg cac gga gtt att agt        48
Gly Ser Gly Tyr Thr Phe Thr Asp Tyr Ala Met His Gly Val Ile Ser
1               5                   10                  15 tct tac tat ggt gat gct agc tac tac tgt gca aga tat agg ggg ctc        96
Ser Tyr Tyr Gly Asp Ala Ser Tyr Tyr Cys Ala Arg Tyr Arg Gly Leu
                20                  25                  30 tgg tac ttc gat gtc tgg ggc                                           117
Trp Tyr Phe Asp Val Trp Gly
        35

<210> SEQ ID NO 42
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Ser Gly Tyr Thr Phe Thr Asp Tyr Ala Met His Gly Val Ile Ser
1               5                   10                  15

Ser Tyr Tyr Gly Asp Ala Ser Tyr Tyr Cys Ala Arg Tyr Arg Gly Leu
                20                  25                  30

Trp Tyr Phe Asp Val Trp Gly
        35

<210> SEQ ID NO 43
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(108)

<400> SEQUENCE: 43 gct tct ggg tat acc ttc aca aac tat gga atg aac ggc tgg ata aac        48
Ala Ser Gly Tyr Thr Phe Thr Asn Tyr Gly Met Asn Gly Trp Ile Asn
1               5                   10                  15 acc tac act gga gag cca aca tat ttc tgt aca acg tac gct act agc        96
Thr Tyr Thr Gly Glu Pro Thr Tyr Phe Cys Thr Thr Tyr Ala Thr Ser
                20                  25                  30 tgg tac tgg ggc                                                       108
Trp Tyr Trp Gly
        35

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Ser Gly Tyr Thr Phe Thr Asn Tyr Gly Met Asn Gly Trp Ile Asn
1               5                   10                  15

Thr Tyr Thr Gly Glu Pro Thr Tyr Phe Cys Thr Thr Tyr Ala Thr Ser
                20                  25                  30

Trp Tyr Trp Gly
        35
```

<210> SEQ ID NO 45
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(111)

<400> SEQUENCE: 45

```
gtc act ggc tac tca atc acc agt gat tat gcc tgg aac ggc tac ata      48
Val Thr Gly Tyr Ser Ile Thr Ser Asp Tyr Ala Trp Asn Gly Tyr Ile
1               5                   10                  15 agc tac agt agt atc act aac tac tac tgt gct ggt ctt tac tat gtt      96
Ser Tyr Ser Ser Ile Thr Asn Tyr Tyr Cys Ala Gly Leu Tyr Tyr Val
            20                  25                  30 atg gac cac tgg ggt                                                 111
Met Asp His Trp Gly
        35
```

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Val Thr Gly Tyr Ser Ile Thr Ser Asp Tyr Ala Trp Asn Gly Tyr Ile
1               5                   10                  15

Ser Tyr Ser Ser Ile Thr Asn Tyr Tyr Cys Ala Gly Leu Tyr Tyr Val
            20                  25                  30

Met Asp His Trp Gly
        35

<210> SEQ ID NO 47
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(105)

<400> SEQUENCE: 47

```
tct agt aag agt ctc ctg cat agt aat ggc aac act tac ttg tat gta      48
Ser Ser Lys Ser Leu Leu His Ser Asn Gly Asn Thr Tyr Leu Tyr Val
1               5                   10                  15 tat cgg atg tcc aac ctt tat tgt atg caa cat cta gaa tat cct ttc      96
Tyr Arg Met Ser Asn Leu Tyr Cys Met Gln His Leu Glu Tyr Pro Phe
            20                  25                  30 acg ttc ggt                                                         105
Thr Phe Gly
        35
```

<210> SEQ ID NO 48
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Ser Lys Ser Leu Leu His Ser Asn Gly Asn Thr Tyr Leu Tyr Val
1               5                   10                  15

Tyr Arg Met Ser Asn Leu Tyr Cys Met Gln His Leu Glu Tyr Pro Phe
                20                  25                  30

Thr Phe Gly
        35

<210> SEQ ID NO 49
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(99)

<400> SEQUENCE: 49 gcc agt gaa agt gtt gat agt tat ggc aat agt ttt atg cac atc tat    48
Ala Ser Glu Ser Val Asp Ser Tyr Gly Asn Ser Phe Met His Ile Tyr
1               5                   10                  15 cgt gca tcc aac cta tac tgt cag caa agt aat gag gat ctg acg ttc    96
Arg Ala Ser Asn Leu Tyr Cys Gln Gln Ser Asn Glu Asp Leu Thr Phe
                20                  25                  30 ggt                                                                 99
Gly

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Ser Glu Ser Val Asp Ser Tyr Gly Asn Ser Phe Met His Ile Tyr
1               5                   10                  15

Arg Ala Ser Asn Leu Tyr Cys Gln Gln Ser Asn Glu Asp Leu Thr Phe
                20                  25                  30

Gly

<210> SEQ ID NO 51
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(87)

<400> SEQUENCE: 51 gcc agc tca agt gta agt tac atg tac att tat ctc aca tcc aac ctg    48
Ala Ser Ser Ser Val Ser Tyr Met Tyr Ile Tyr Leu Thr Ser Asn Leu
1               5                   10                  15 tac tgc cag cag tgg agt agt gac cct ttc acg ttc ggc                87
Tyr Cys Gln Gln Trp Ser Ser Asp Pro Phe Thr Phe Gly
                20                  25

<210> SEQ ID NO 52
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Ala Ser Ser Ser Val Ser Tyr Met Tyr Ile Tyr Leu Thr Ser Asn Leu
1               5                   10                  15

Tyr Cys Gln Gln Trp Ser Ser Asp Pro Phe Thr Phe Gly
            20                  25

<210> SEQ ID NO 53
<211> LENGTH: 345
<212> TYPE: DNA
<213> ORGANISM: Mus sp.

<400> SEQUENCE: 53
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacacct acactggaga gccaacatat     180
gctgatgact tcaagggacg gtttgccttc tctttggaaa cctctgccag cactgcctat     240
ttgcagatca acaacctcaa aaatgaggac acggctacat atttctgtac aacgtacgct     300
actagctggt actggggcca aggcaccact ctcacagtct cctca                    345

<210> SEQ ID NO 54
<211> LENGTH: 331
<212> TYPE: DNA
<213> ORGANISM: Mus sp.

<400> SEQUENCE: 54
gacattgtgc tgacccaatc tccagcttct ttggctgtgt ctctagggca gagggccacc      60
atatcctgca gagccagtga aagtgttgat agttatggca atagttttat gcactggtat     120
cagcagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgatgt tgcaacctat tactgtcagc aaagtaatga ggatctgacg     300
ttcggtggag gcaccaagct ggaaatcaaa c                                   331

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
ggctacacat tcactgatta tgct                                            24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
gggtatacct tcacaaacta tgga                                    24

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggctactcaa tcaccagtga ttatgcc                                 27

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
attagttctt actatggtga tgct                                    24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ataaacacct acactggaga gcca                                    24

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ataagctaca gtagtatcac t                                       21

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gcaagatata gggggctctg gtacttcgat gtc                          33

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
acaacgtacg ctactagctg gtac                                          24

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gctggtcttt actatgttat ggaccac                                       27

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aagagtctcc tgcatagtaa tggcaacact tac                                33

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gaaagtgttg atagttatgg caatagtttt                                    30

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcaagtgtaa gttac                                                    15

<210> SEQ ID NO 67
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67 cggatgtcc                                                            9

<210> SEQ ID NO 68
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 68 cgtgcatcc                                                          9

<210> SEQ ID NO 69
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69 ctcacatcc                                                          9

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
atgcaacatc tagaatatcc tttcacg                                     27

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cagcaaagta atgaggatct gacg                                        24

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cagcagtgga gtagtgaccc tttcacg                                     27
```